US010945755B2

(12) United States Patent
Brady et al.

(10) Patent No.: US 10,945,755 B2
(45) Date of Patent: Mar. 16, 2021

(54) MECHANICAL LOCKOUT FOR ULTRASONIC SURGICAL INSTRUMENT

(71) Applicant: ETHICON LLC, Guaynabo, PR (US)

(72) Inventors: John E. Brady, Liberty Township, OH (US); Alexander R. Cuti, Cincinnati, OH (US); Kevin M. Fiebig, Cincinnati, OH (US); Ellen Burkart, Cincinnati, OH (US); Demetrius N. Harris, Cincinnati, OH (US); Andrew Kolpitcke, Centerville, OH (US); Amy M. Krumm, Cincinnati, OH (US); Matthew T. Kuhn, Houston, TX (US); Jason R. Lesko, Cincinnati, OH (US); Stephen M. Leuck, Cincinnati, OH (US); Guion Y. Lucas, Cincinnati, OH (US); Cameron D. McLain, Cincinnati, OH (US); Andrew S. Meyers, Cincinnati, OH (US); Candice Otrembiak, Loveland, OH (US); Grace E. Waters, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 202 days.

(21) Appl. No.: 15/951,773

(22) Filed: Apr. 12, 2018

(65) Prior Publication Data
US 2019/0314055 A1 Oct. 17, 2019

(51) Int. Cl.
*A61B 17/32* (2006.01)
*A61B 18/14* (2006.01)
(Continued)

(52) U.S. Cl.
CPC ......... *A61B 17/320092* (2013.01); *A61B 17/320068* (2013.01); *A61B 18/1445* (2013.01);
(Continued)

(58) Field of Classification Search
CPC .......... A61B 2018/00577; A61B 2018/00589; A61B 2018/00595; A61B 2018/00601;
(Continued)

(56) References Cited

U.S. PATENT DOCUMENTS

| 5,322,055 A | 6/1994 | Davison et al. |
| 5,873,873 A | 2/1999 | Smith et al. |

(Continued)

FOREIGN PATENT DOCUMENTS

| EP | 1 199 040 A2 | 4/2002 |
| EP | 2 870 938 A1 | 5/2015 |

(Continued)

OTHER PUBLICATIONS

U.S. Appl. No. 61/410,603, entitled "Energy-Based Surgical Instruments," filed Nov. 5, 2010.

(Continued)

*Primary Examiner* — George J Ulsh
*Assistant Examiner* — Andrew P. Restaino
(74) *Attorney, Agent, or Firm* — Frost Brown Todd LLC

(57) ABSTRACT

An ultrasonic surgical instrument includes a first modular assembly including at least one operator input feature an ultrasonic transducer supported by the first modular assembly, and a second modular assembly configured to be removably coupled with the first modular assembly. The second modular assembly includes at least a portion of an end effector extending distally from a distal end portion of the second modular assembly. The instrument includes a mechanical lockout assembly configured to switch between at least an unlocked configuration and a locked configuration. In the locked configuration, the first modular assembly and the second modular assembly are partially coupled together such that the operator is physically prevented from activating the instrument using the operator input feature. In (Continued)

the unlocked configuration, the first modular assembly and the second modular assembly are completely coupled together and the operator is able to activate the instrument using the operator input feature.

20 Claims, 38 Drawing Sheets

(51) Int. Cl.
    *A61B 17/00*      (2006.01)
    *A61B 18/00*      (2006.01)

(52) U.S. Cl.
    CPC ............... *A61B 2017/00402* (2013.01); *A61B 2017/00424* (2013.01); *A61B 2017/00473* (2013.01); *A61B 2017/00477* (2013.01); *A61B 2017/320074* (2017.08); *A61B 2017/320088* (2013.01); *A61B 2017/320095* (2017.08); *A61B 2018/0063* (2013.01); *A61B 2018/00589* (2013.01); *A61B 2018/00994* (2013.01)

(58) Field of Classification Search
    CPC .. A61B 2018/00607; A61B 2018/0063; A61B 17/295; A61B 17/2841; A61B 17/2909; A61B 17/320068; A61B 2017/0046; A61B 17/320092; A61B 2018/00994; A61B 2017/00477; A61B 2017/00473; A61B 2017/00424; A61B 2017/00402; A61B 18/1445; A61B 2017/320095; A61B 2017/320074; A61B 2090/0808; A61B 2017/320094; A61B 17/2804
    See application file for complete search history.

(56) References Cited

U.S. PATENT DOCUMENTS

| | | | |
|---|---|---|---|
| 5,980,510 | A | 11/1999 | Tsonton et al. |
| 6,325,811 | B1 | 12/2001 | Messerly |
| 6,773,444 | B2 | 8/2004 | Messerly |
| 6,783,524 | B2 | 8/2004 | Anderson et al. |
| 8,663,220 | B2 | 3/2014 | Wiener et al. |
| 9,681,884 | B2 | 6/2017 | Clem et al. |
| 10,368,892 | B2 | 8/2019 | Stulen et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2009/0105750 | A1 | 4/2009 | Price et al. |
| 2010/0069940 | A1 | 3/2010 | Miller et al. |
| 2011/0015660 | A1 | 1/2011 | Wiener et al. |
| 2011/0087212 | A1 | 4/2011 | Aldridge et al. |
| 2012/0029546 | A1 | 2/2012 | Robertson |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0114334 | A1 | 4/2014 | Olson et al. |
| 2014/0330298 | A1 | 11/2014 | Arshonsky et al. |
| 2015/0080924 | A1 | 3/2015 | Stulen et al. |
| 2015/0080925 | A1 | 3/2015 | Schulte et al. |
| 2015/0141981 | A1 | 5/2015 | Price et al. |
| 2015/0148830 | A1* | 5/2015 | Stulen ............ A61B 17/320068 606/169 |
| 2017/0000541 | A1 | 1/2017 | Yates et al. |
| 2017/0105754 | A1 | 4/2017 | Boudreaux et al. |
| 2017/0105755 | A1 | 4/2017 | Boudreaux et al. |
| 2017/0105788 | A1* | 4/2017 | Boudreaux ........ A61B 17/2816 |
| 2018/0132926 | A1* | 5/2018 | Asher ................ A61B 17/2804 |

FOREIGN PATENT DOCUMENTS

| | | |
|---|---|---|
| EP | 3 225 176 A1 | 10/2017 |
| WO | WO 2017/100412 A1 | 6/2017 |

OTHER PUBLICATIONS

U.S. Appl. No. 62/363,411, entitled "Surgical Instrument with Dual Mode End Effector," filed Jul. 18, 2016.
U.S. Appl. No. 15/644,930, entitled "Acoustic Drivetrain with External Collar at Nodal Position," filed Jul. 10, 2017.
U.S. Appl. No. 15/644,944, entitled "Features to Couple Acoustic Drivetrain Components in Ultrasonic Surgical Instrument," filed Jul. 10, 2017.
U.S. Appl. No. 15/951,747, entitled "Electrical Lockout for Ultrasonic Surgical Instrument," filed Apr. 12, 2018.
U.S. Appl. No. 15/951,788, entitled "Mechanical Lockout for Ultrasonic Surgical Instrument," filed Apr. 12, 2018.
U.S. Appl. No. 15/951,811, entitled "Mechanical Lockout for Ultrasonic Surgical Instrument," filed Apr. 12, 2018.
European Search Report, Extended, and Written Opinion dated Jul. 17, 2019 for Application No. 19168695.5, 8 pgs.
European Search Report, Extended, and Written Opinion dated Jul. 5, 2019 for Application No. EP 19168712.8, 8 pgs.
European Search Report, Extended, and Written Opinion dated Jul. 3, 2019 for Application No. EP 19168735.9, 8 pgs.
European Search Report, Extended, and Written Opinion dated Jul. 11, 2019 for Applicafion No. EP 19168796.1, 8 pgs.
International Search Report and Written Opinion dated Jul. 3, 2019 for Application No. PCT/IB2019/053002, 15 pgs.
International Search Report and Written Opinion dated Jul. 11, 2019 for Application No. PCT/IB2019/053004, 12 pgs.
International Search Report and Written Opinion dated Jul. 11, 2019 for Application No. PCT/IB2019/053008, 12 pgs.
International Search Report and Written Opinion dated Jul. 17, 2019 for Application No. PCT/IB2019/053009, 11 pgs.

* cited by examiner

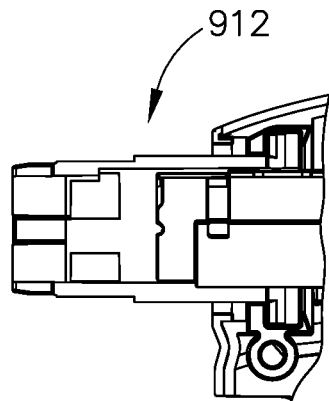 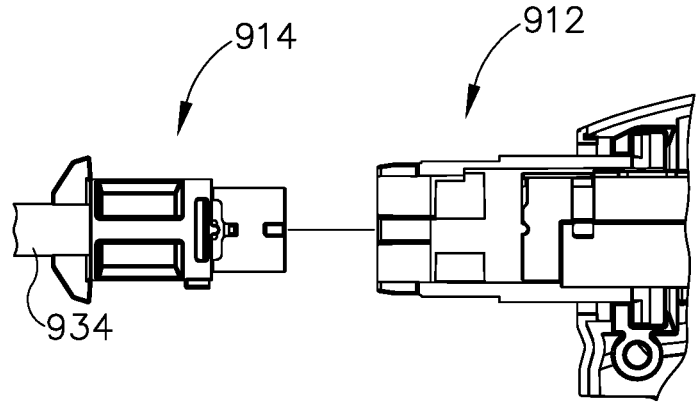
Fig.28A  Fig.28B
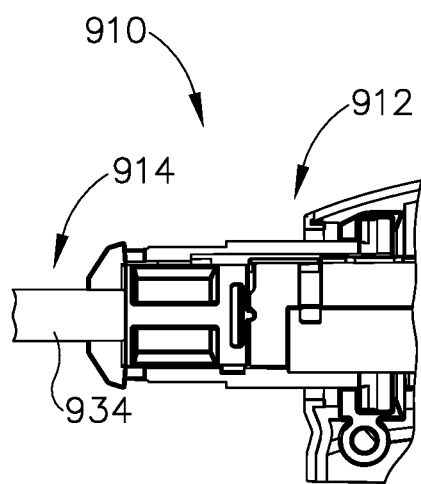 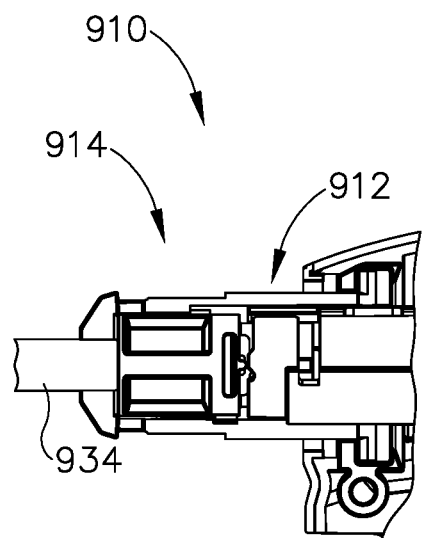
Fig.28C  Fig.28D

MECHANICAL LOCKOUT FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, the disclosure of which is incorporated by reference herein; U.S. Pub. No. 2010/0069940, entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011, the disclosure of which is incorporated by reference herein; and U.S. Pub. No. 2012/0029546, entitled "Ultrasonic Surgical Instrument Blades," published Feb. 2, 2012, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, the disclosure of which is incorporated by reference herein; and U.S. Pub. No. 2014/0114334, entitled "Flexible Harmonic Waveguides/Blades for Surgical Instruments," published Apr. 24, 2014 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 28A depicts a schematic side sectional view of an enlarged portion of the instrument similar to FIG. 27A in the unlocked configuration of FIG. 27A;

FIG. 28B depicts the schematic side sectional view of the enlarged portion of the instrument similar to FIG. 28A in the locked configuration of FIG. 27B as the shaft assembly is introduced;

FIG. 28C depicts the schematic side sectional view of the enlarged portion of the instrument similar to FIG. 28B, but in the locked configuration of FIG. 27C as the shaft assembly is inserted;

FIG. 28D depicts the schematic side sectional view of the enlarged portion of the instrument similar to FIG. 28C, but in the unlocked configuration of FIG. 27D;

Figure 1A:
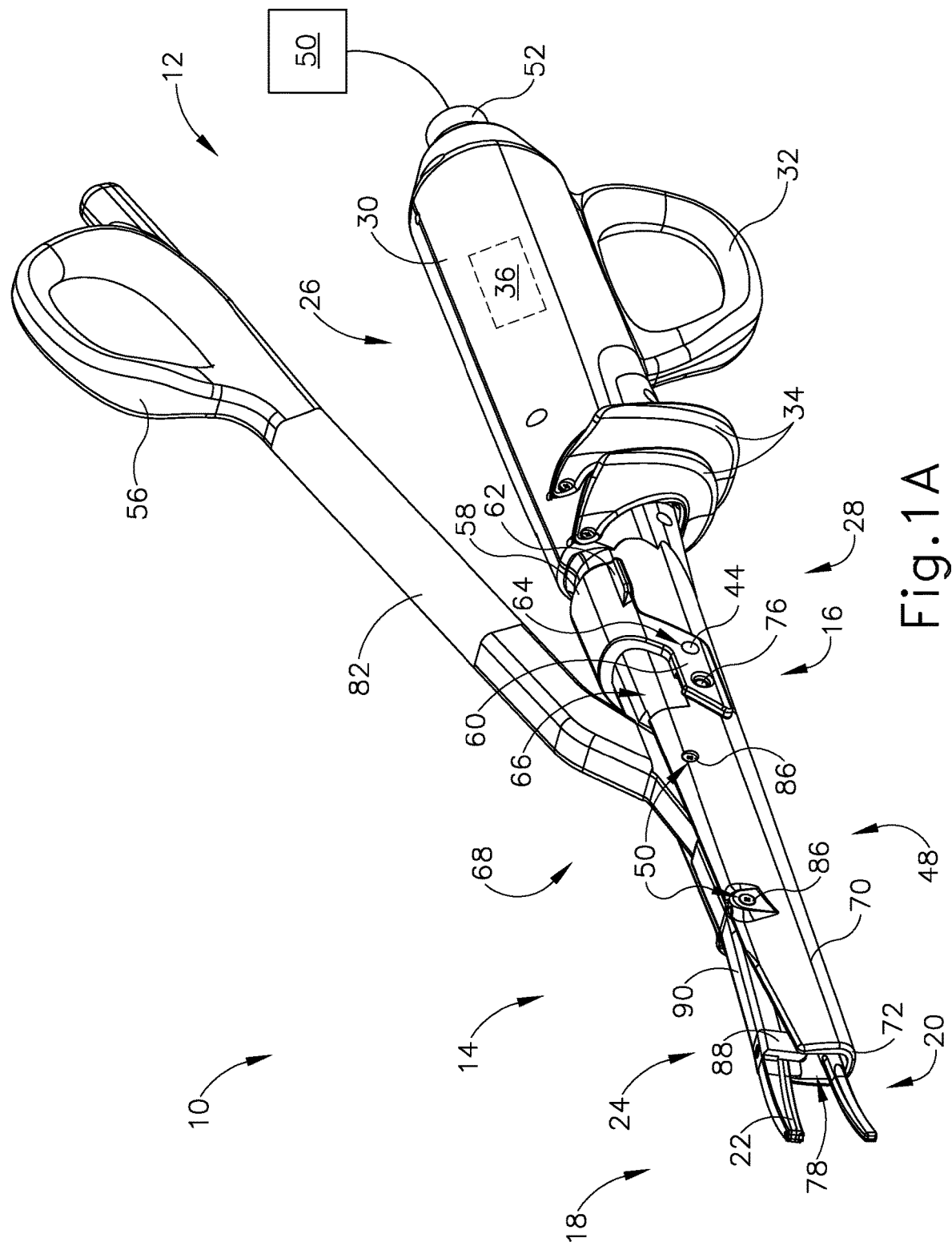
FIG. 1A depicts a perspective view of a first exemplary surgical instrument, with an end effector of the instrument in an open configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. First Exemplary Ultrasonic Surgical Instrument for Surgical Procedures

Figure 1B:
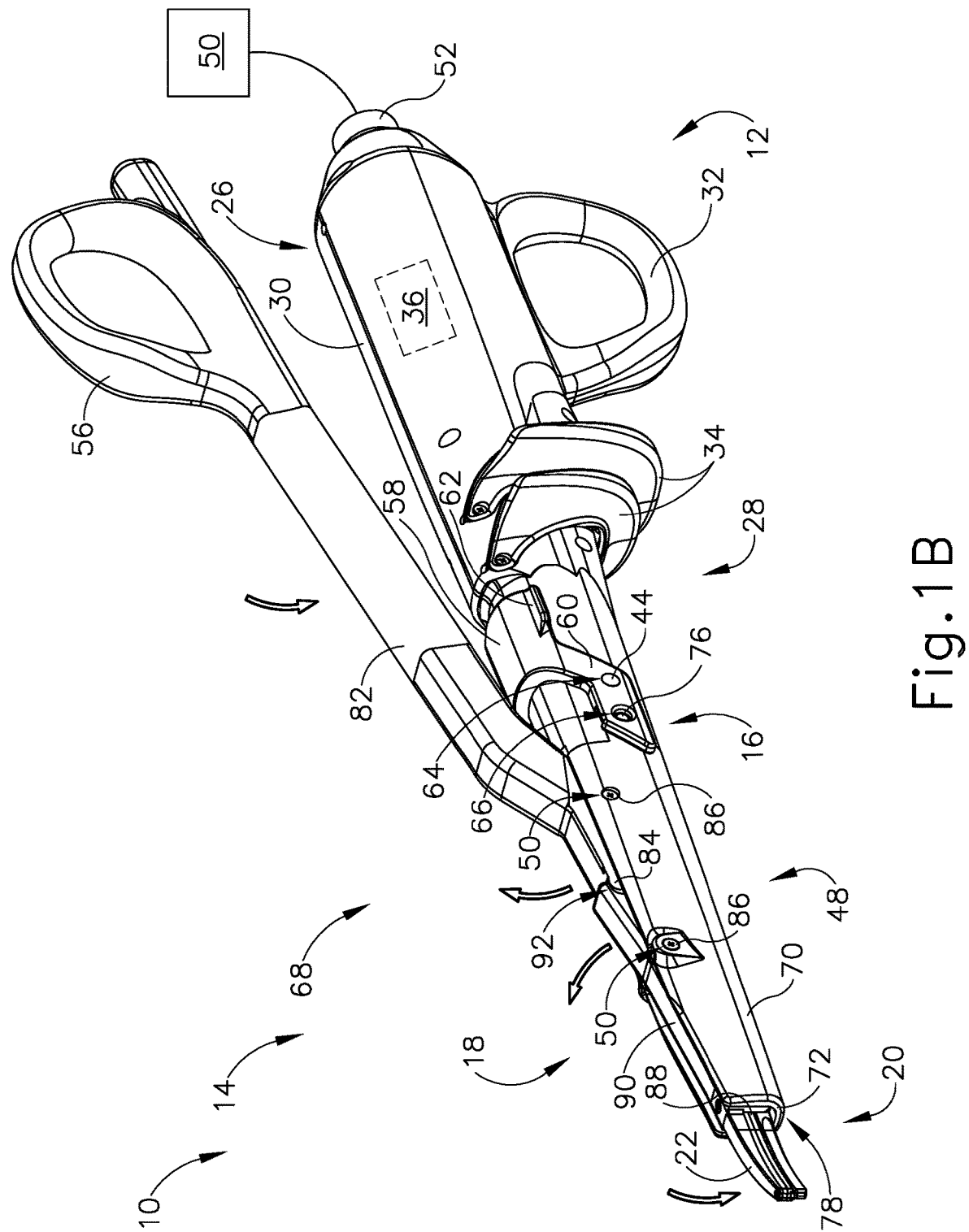
FIG. 1B depicts a perspective view of the instrument of FIG. 1A, with the end effector in a closed configuration.
Figure 2:
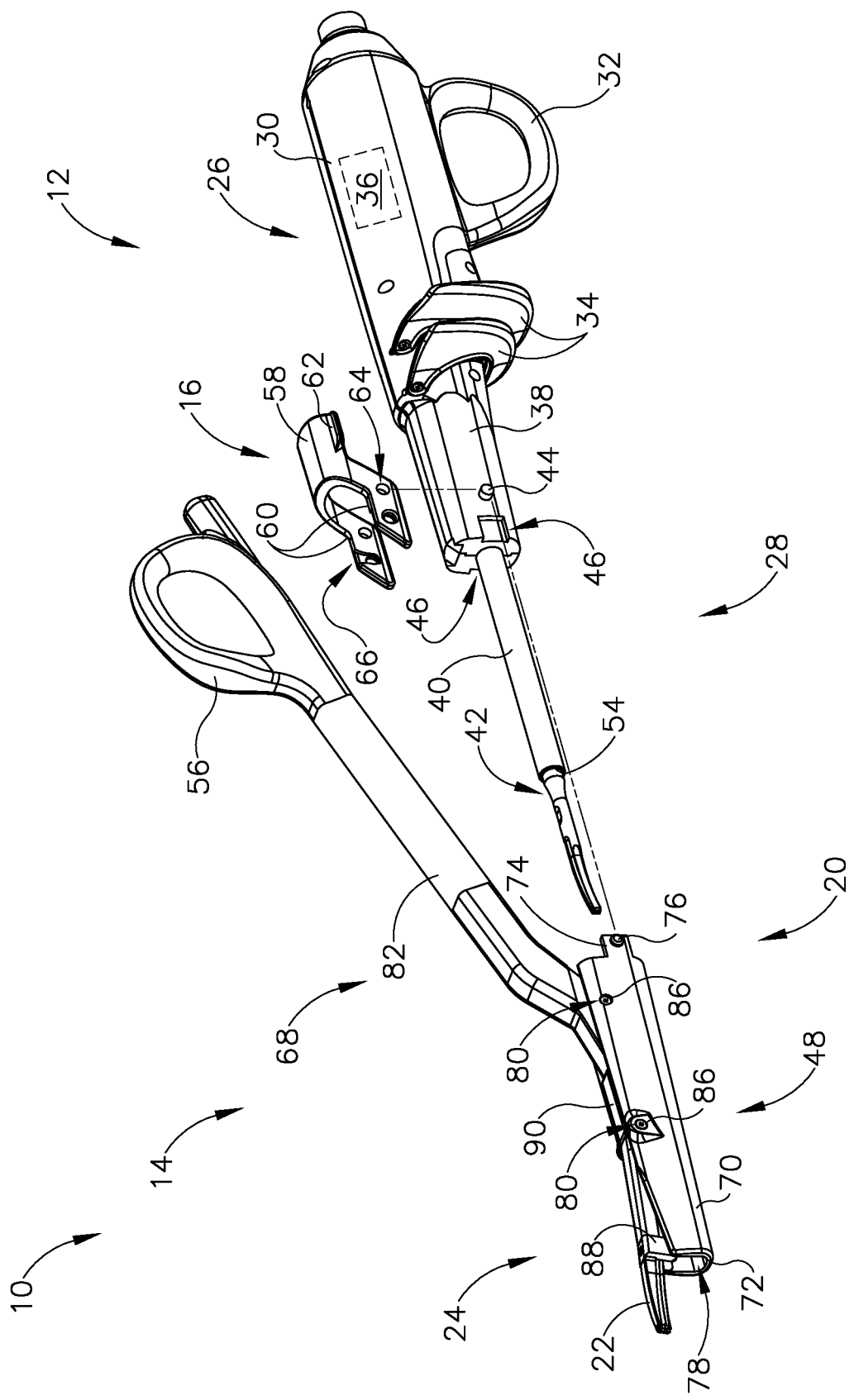
FIG. 2 depicts an exploded perspective view of the instrument of FIG. 1A.

FIGS. 1A-2 illustrate a first exemplary ultrasonic surgical instrument (10). At least part of instrument (10) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750; U.S. Pub. No. 2010/0069940; U.S. Pub. No. 2011/0015660; U.S. Pub. No. 2012/0112687; U.S. Pub. No. 2012/0116265; U.S. Pub. No. 2014/0005701; U.S. Pub. No. 2014/0114334; U.S. Pat. App. No. 61/410,603; and/or U.S. patent application Ser. No. 14/028,717. The disclosures of each of the foregoing patents, publications, and applications are incorporated by reference herein. In addition, or in the alternative, at least part of instrument (10) may be constructed and operable in accordance with at least some of the teachings of U.S. patent application Ser. No. 15/284,837, entitled "Surgical Instrument with Dual Mode End Effector and Compound Lever with Detents," filed Oct. 4, 2016, the disclosure of which is incorporated by reference herein; and/or U.S. Pat. App. No. 62/363,411, entitled "Surgical Instrument with Dual Mode End Effector," filed Jul. 18, 2016, the disclosure of which is incorporated by reference herein.

As described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

Instrument (10) in the present example includes a first modular assembly (12), a second modular assembly (14), and a coupling member (16). As will be described in greater detail below, coupling member (16) may selectively attach first modular assembly (12) with second modular assembly (14) in order to form instrument (10) with an end effector (18). As best seen in FIGS. 1A-1B, end effector (18) comprises an ultrasonic blade (20) and a clamp pad (22) of a clamp pad assembly (24).

Additionally, as will be described in greater detail below, selected portions of second modular assembly (14) may actuate relative to first modular assembly (12), when properly attached with each other, in order to actuate end effector (18) from an open configuration (FIG. 1A), to a closed configuration (FIG. 1B). The ability to selectively attach and detach second modular assembly (14) with first modular assembly (12) may provide additional benefits of reusability of either modular assembly (12, 14). For instance, different kinds of first modular assemblies (12) may be used with second modular assembly (14) to provide different kinds of surgical instruments. Similarly, different kinds of second modular assemblies (14) may be used with first modular assembly (12) to provide different kinds of surgical instruments. Additionally, moving components of second modular assembly (14) may be housed within static components of second modular assembly (14), which may provide additional advantages, some of which are described below while others will be apparent to one having ordinary skill in the art in view of the teachings herein.

First modular assembly (12) includes a handle assembly (26), a shaft assembly (28) extending distally from handle assembly (26), and ultrasonic blade (20) extending distally from shaft assembly (28). Handle assembly (26) includes a body (30), a finger grip ring (32), a pair of buttons (34) distal to finger grip ring (32), and an ultrasonic transducer assembly (36) housed within body (30).

Shaft assembly (28) includes a proximal outer sheath (38) extending distally from body (30), a tube (40) extending distally from proximal outer sheath (38), and a waveguide (42) extending within and through both proximal outer sheath (38) and tube (40). Proximal outer sheath (38) includes a pair of protrusions (44). Additionally, proximal outer sheath (38) defines a pair of recesses (46). As will be described in greater detail below, recesses (46) are dimensioned to mate with a portion of distal outer sheath (48) while protrusions (44) are configured to pivotally couple proximal outer sheath (38) with coupling member (16). Both protrusions (44) and recesses (46) may help couple first modular assembly (12) with second modular assembly (14).

Proximal outer sheath (38) may be fixed relative to body (30), while tube (40) may be fixed relative to proximal outer sheath (38). As will be described in greater detail below, waveguide (42) may attach to transducer assembly (36) and be supported by portions of proximal outer sheath (38) and tube (40). Ultrasonic blade (20) may be unitarily connected to waveguide (42), and also extend distally from waveguide (42). As will be described in greater detail below, waveguide (42) is operable to connect to ultrasonic transducer assembly (36) in order to provide acoustic communication between ultrasonic blade (20) and transducer assembly (36).

Transducer assembly (36) is housed within body (30) of handle assembly (26). As seen in FIGS. 1A-1B, transducer assembly (36) is coupled with a generator (50) via a plug (52). Transducer assembly (36) receives electrical power from generator (50) and converts that power into ultrasonic vibrations through piezoelectric principles. Generator (50) may include a power source and control module that is configured to provide a power profile to transducer assembly (36) that is particularly suited for the generation of ultrasonic vibrations through transducer assembly (36). Generator (50) may also be configured to provide a power profile that enables end effector (18) to apply RF electrosurgical energy to tissue.

By way of example only, generator (50) may comprise a GEN 300 sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (50) may be integrated into handle assembly (26), and that handle assembly (26) may even include a battery or other on-board power source such that plug (52) is omitted. Still other suitable forms that generator (50) may take, as well as various features and operabilities that generator (50) may provide, will be apparent to those of ordinary skill in the art in view of the teachings herein.

Ultrasonic vibrations that are generated by transducer assembly (36) are communicated along acoustic waveguide (42) when properly coupled. Waveguide (42) is mechanically and acoustically coupled with transducer assembly (36). Waveguide (42) extends through shaft assembly (28) to reach ultrasonic blade (20). Waveguide (42) may be secured to proximal outer sheath (38) and/or body (30) via a pin (not shown) extending through waveguide (42) and proximal outer sheath (38). Pin may help ensure waveguide (42) remains longitudinally and rotationally fixed relative to the rest of shaft assembly (28) when waveguide (42) is in a deactivated state (i.e. not vibrating ultrasonically).

Additionally, waveguide (42) may be supported by tube (40) via seals (54) located between an interior of tube (40) and an exterior of waveguide (42). Seals (54) may also prevent unwanted matter and fluid from entering portions of tube (40) housing waveguide (42). Pin (not shown) and seals (54) are located at positions along the length of waveguide (42) corresponding to nodes associated with resonant ultrasonic vibrations communicated through waveguide (42). Therefore, contact between waveguide (42) and pin (not shown), as well as contact between waveguide (42) and seals (54) may not affect ultrasonic vibrations communicated through waveguide (42).

When ultrasonic blade (20) is in an activated state (i.e., vibrating ultrasonically), ultrasonic blade (20) is operable to effectively cut through and seal tissue, particularly when the tissue is being clamped between clamp pad (22) and ultrasonic blade (20). It should be understood that waveguide (42) may be configured to amplify mechanical vibrations transmitted through waveguide (42). Furthermore, waveguide (42) may include features operable to control the gain of the longitudinal vibrations along waveguide (42) and/or features to tune waveguide (42) to the resonant frequency of the system.

In the present example, the distal end of ultrasonic blade (20) is located at a position corresponding to an anti-node associated with resonant ultrasonic vibrations communicated through waveguide (42), in order to tune the acoustic assembly to a preferred resonant frequency $f_o$ when the acoustic assembly is not loaded by tissue. When transducer assembly (36) is energized, the distal end of ultrasonic blade (20) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (36) of the present example is activated, these mechanical oscillations are transmitted through the waveguide (42) reach ultrasonic blade (20), thereby providing oscillation of ultrasonic blade (20) at the resonant ultrasonic frequency. Thus, when tissue is secured between ultrasonic blade (20) and clamp pad (22), the ultrasonic oscillation of ultrasonic blade (20) may simultaneously sever the tissue and denature the proteins in adjacent tissue cells, thereby providing a coagulative effect with relatively little thermal spread.

In some versions, an electrical current may also be provided through ultrasonic blade (20) and/or clamp pad (22) to also seal the tissue. It should therefore be understood that instrument (10) may also be configured to provide radiofrequency (RF) energy to a surgical site via end effector (18). By way of example only, an operator may rely mainly on the use of ultrasonic energy from blade (20) to sever tissue that is captured between ultrasonic blade (20) and clamp pad (22). The operator may further rely on the use of RF energy from end effector (18) to seal the severed tissue. Of course, it will be understood that the ultrasonic energy from blade (20) may seal tissue to some degree, such that the RF energy from end effector (18) may supplement the sealing that would already be provided from the ultrasonic energy. It will also be understood that there may be instances where the operator may wish to simply use end effector (18) to only apply RF energy to tissue, without also applying ultrasonic energy to tissue. As will be appreciated from the description herein, some versions of instrument (10) are capable of providing all of the above noted kinds of functionality. Various ways in which instrument (10) may be configured and operable to provide both ultrasonic and RF electrosurgical modes of operation are described in various references cited herein; while other ways in which instrument (10) may be configured and operable to provide both ultrasonic and RF electrosurgical modes of operation will be apparent to those of ordinary skill in the art in view of the teachings herein.

An operator may activate buttons (34) to selectively activate transducer assembly (36) to thereby activate ultrasonic blade (20). In the present example, two buttons (34) are provided. In some versions, one button (34) is provided for activating ultrasonic blade (20) at a first power profile (e.g., a first frequency and/or first amplitude) and another button (34) is provided for activating ultrasonic blade (20) at a second power profile (e.g., a second frequency and/or second amplitude). In some other versions, one button (34) is provided for activating ultrasonic blade (20) with ultrasonic energy, and the other button (34) is provided for activating end effector (18) with RF energy. In some other versions, one button (34) is operable to activate ultrasonic blade (20) with ultrasonic energy while simultaneously activating end effector (18) with RF energy; while the other button (34) is only operable to activate ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while still activating ultrasonic blade (20) with ultrasonic energy. In some other versions, at least one button (34) is operable to initially activate ultrasonic blade (20) with ultrasonic energy, then based on one or more other conditions (e.g., time, measured impedance, etc.) while button (34) remains activated, eventually activating end effector (18) with RF energy while ceasing activation of ultrasonic blade (20) with ultrasonic energy. In some other versions, at least one button (34) is operable to initially activate end effector (18) with RF energy, then based on one or more other conditions (e.g., time, measured impedance, etc.) while button (34) remains activated, eventually activating ultrasonic blade (20) with ultrasonic energy while ceasing activation of end effector (18) with RF energy.

It should be understood that any other suitable number of buttons and/or otherwise selectable power levels and/or power modalities may be provided. For instance, a foot pedal may be provided to selectively activate transducer assembly (36).

Buttons (34) of the present example are positioned such that an operator may readily fully operate instrument (10) with a single hand. For instance, when first and second modular assemblies (12, 14) are coupled, the operator may position their thumb in thumb grip ring (56), position their ring finger in finger grip ring (32), position their middle finger about body (30), and manipulate buttons (34) using their index finger. Of course, any other suitable techniques may be used to grip and operate instrument (10), and buttons (34) may be located at any other suitable position.

As mentioned above, and as will be described below, coupling member (16) is configured to selectively couple first modular assembly (12) with second modular assembly (14). As best seen in FIG. 2, coupling member (16) comprises a body (58), a pair of resilient arms (60), and a pair of grips (62) extending from body (58). Resilient arms (60) each define a respective pivot bore (64) and a locking assembly (66). Resilient arms (60) are spaced apart from each other in order to receive proximal outer sheath (38) and to snap-fit pivot bores (64) with respective protrusions (44). Coupling member (16) is configured to pivotally connect with proximal outer sheath (38) via pivot bores (64) and protrusions (44). While in the current example, coupling member (16) and proximal outer sheath (38) are pivotally coupled via snap-fitting, any other type of suitable connection may be used as would be apparent to one having ordinary skill in the art in view of the teachings herein. For example, protrusions (44) may be extendable relative to proximal outer sheath (38) in order to pivotally couple with pivot bore (64) of coupling member (16). Grips (62) may be positioned on body (58) such that an operator may easily rotate coupling member (16) relative to proximal outer sheath (38) via grips (62). As will be described in greater detail below, locking assembly (66) is configured to rotate about pivot bore (64) and protrusions (44) in order to selectively couple with portions of first modular assembly (14).

While coupling member (16) in the current example is used to connect first modular assembly (12) with second modular assembly (14), it should be understood that coupling member (16) may be incorporated into any suitable type of modular assembly that would be apparent to one having ordinary skill in the art in view of the teachings herein. For example, coupling member (16) may be modified to couple different modular clamp arm assemblies with first modular assembly (12) where the different modular clamp arm assemblies include clamp arm assemblies such as those taught in U.S. patent application Ser. No. 15/284,855, entitled "Surgical Instrument with Dual Mode End Effector and Modular Clamp Arm Assembly," filed Oct. 4, 2016, the disclosure of which is incorporated by reference herein. Thus, one modular clamp arm assembly that may be coupled with first modular assembly (12) may provide pivotal motion of a clamp arm at one side of ultrasonic blade (20) while the other modular clamp arm assembly that may be coupled with first modular assembly (12) may provide pivotal motion of a clamp arm at the other side of ultrasonic blade (20). Other suitable kinds of clamp arm assemblies that may be used to provide different kinds of second modular assemblies (14) will be apparent to those of ordinary skill in the art in view of the teachings herein.

Second modular assembly (14) includes a clamp arm assembly (68), clamp pad assembly (24), and a distal outer sheath (48). As will be described in greater detail below, distal outer sheath (48) is configured to couple with both coupling member (16) and proximal outer sheath (38) in order to selectively couple first modular assembly (12) with second modular assembly (14). It other words, when properly coupled, proximal outer sheath (38) and distal outer sheath (48) may be fixed relative to one another. As will also be described in greater detail below, clamp arm assembly (68) and clamp pad assembly (24) are both pivotally coupled with distal outer sheath (48). Additionally, clamp arm assembly (68) and clamp pad assembly (24) are dimensioned to mesh with each other such that rotation of one assembly (24, 68) relative to distal outer sheath (48) causes rotation of the other assembly (24, 68) relative to distal outer sheath (48). In other words, clamp pad assembly (24) and clamp arm assembly (68) are capable of rotating each other relative to distal outer sheath (48).

Distal outer sheath (48) includes a U-shaped body (70) extending from a distal face (72) and terminating in a pair of proximally presented projections (74). Proximally presented projections (74) each include a lateral protrusion (76) extending away from U-shaped body (70). U-shaped body (70) defines a longitudinal pathway (78) and a plurality of bores (80). U-shaped body (70) and longitudinal pathway (78) are dimensioned to receive tube (40) and to rotationally house a portion of clamp arm assembly (68) and clamp pad assembly (24). In particular, U-shaped body (70) may be inserted over ultrasonic blade (20) and tube (40) such that tube (40) will rest under clamp arm assembly (68) and clamp pad assembly (24). Tube (40) may protect waveguide (42) such that clamp arm assembly (68) and clamp pad assembly (24) do not contact adjacent portions of waveguide (42).

As shown in FIG. 2, proximally presented projections (74) are configured to be inserted into recesses (46) defined by proximal outer sheath (38). When proximally presented projections (74) are inserted into recesses (46), distal outer sheath (48) may not rotate relative to proximal outer sheath (38) about a longitudinal axis defined by tube (40). Therefore, proximally presented projections (74) may mate with recesses (46) in order to rotationally fix distal outer sheath (48) relative to proximal outer sheath (38).

Once distal outer sheath (48) is rotationally fixed relative to proximal outer sheath (38), an operator may rotate coupling member (16) such that locking assembly (66) snap-fits with lateral protrusions (76). In particular, an operator may rotate coupling member (16) about protrusions (44) such that lateral protrusions (76) cam against resilient arms (60). As a result, resilient arms (60) are flexed outwardly away from proximally presented projections (74). An operator may further rotate coupling member (16) about protrusions (44). The resilient nature of resilient arms (60) allows resilient arms (60) to return to a relaxed position such that lateral protrusions (76) rest within locking assembly (66). With locking assembly (66) of coupling member (16) fully attached, distal outer sheath (48) is longitudinally fixed relative to proximal outer sheath (38), thereby coupling first modular assembly (12) with second modular assembly (14).

If an operator wishes to decouple first modular assembly (12) with second modular assembly (14), an operator may grasp grips (62) to rotate coupling member (16) in the opposite direction about protrusions (44) in order to flex resilient arms (60) to pop out lateral protrusions (76).

As mentioned above, clamp arm assembly (68) and clamp pad assembly (24) are both pivotally coupled with distal outer sheath (48) such that rotation of one assembly (24, 68) relative to distal outer sheath (48) causes rotation of the other assembly (24, 68) relative to distal outer sheath (48).

Clamp arm assembly (68) includes an elongated arm (82), thumb grip ring (56), a camming protrusion (84) seen in FIG. 1B. Thumb grip ring (56) and elongated arm (82) together provide a scissor grip type configuration in combination with body (30) and finger grip ring (32). Pivot coupling pivotally couples clamp arm assembly (68) with distal outer sheath (48) via pins (86). As will be described in greater detail below, camming protrusion (84) interacts with clamp pad assembly (24) in order to rotate clamp pad assembly (24) in response to rotation of clamp arm assembly (68).

Clamp pad assembly (24) includes clamp pad (24) facing ultrasonic blade (20), a pair of tissue stops (88) located adjacent to ultrasonic blade (20) and proximal to clamp pad (22), an arm (90) defining a camming recess (92) as seen in FIG. 1B. In some versions, clamp pad assembly (24) further includes one or more electrodes that is/are operable to apply RF electrosurgical energy to tissue. Various references herein provide examples of how a clamp pad assembly may incorporate one or more electrodes that is/are operable to apply RF electrosurgical energy to tissue, while other examples of how clamp pad assembly (24) may incorporate one or more electrodes that is/are operable to apply RF electrosurgical energy to tissue will be apparent to those of ordinary skill in the art in view of the teachings herein.

In the current example, tissue stops (88) longitudinally align with distal face (72) when end effector (18) is in the closed position. Tissue stops (88) and distal face (72) may cooperate to consistently and simply prevent tissue from inadvertently reaching a proximal position within end effector (18) where ultrasonic energy from blade (20) may not adequately sever or seal the tissue. In providing such prevention, tissue stop (88) may eliminate the need for an operator to visualize proximal region of end effector (18) in order to determine whether the tissue has reached an undesirably proximal position within end effector (18).

Camming protrusion (84) is dimensioned to rotate within camming recess (92) while also contacting camming recess (92). Camming protrusion (84) and camming recess (92) are positioned within distal outer sheath (48). Therefore, as shown between FIGS. 1A-1B, when an operator rotates elongated arm (82) toward distal outer sheath (48), camming protrusion (84) rotates away from distal outer sheath (48). Because camming protrusion (84) is housed within camming recess (92), upward movement of camming protrusion (84) causes upward movement of camming recess (92). Upward movement of camming recess (92) rotates arm (90) such that clamp pad (22) rotates toward ultrasonic blade (20). Therefore, closure of elongated arm (82) of clamp arm assembly (68) toward handle assembly (26) leads to closure of clamp pad (22) toward ultrasonic blade (20). It should therefore be understood that when first modular assembly (12) and second modular assembly (14) are connected, an operator may squeeze thumb grip ring (56) toward body (30) to thereby clamp tissue between clamp pad assembly (24) and ultrasonic blade (20) to compress tissue against ultrasonic blade (20). When ultrasonic blade (20) is activated during such compression, clamp pad assembly (24) and ultrasonic blade (20) cooperate to transect and/or seal the compressed tissue.

In some versions, one or more resilient members are used to bias clamp pad assembly (24) toward the open position shown in FIG. 1A. Of course, any other suitable kind of resilient member may be used as would be apparent to one having ordinary skill in the art in view of the teachings herein, such as a torsion spring. Alternatively, clamp pad assembly (24) need not necessarily be biased toward the open position.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940; U.S. Pub. No. 2011/0015660; U.S. Pub. No. 2012/0112687; U.S. Pub. No. 2012/0116265; U.S. Pub. No. 2014/0005701; U.S. Pub. No. 2014/0114334; and/or U.S. Pub. No. 2015/0080925, entitled "Alignment Features for Ultrasonic Surgical Instrument," published Mar. 19, 2015, the disclosure of which is incorporated by reference herein.

II. Second Exemplary Ultrasonic Surgical Instrument for Surgical Procedures

Figure 3:
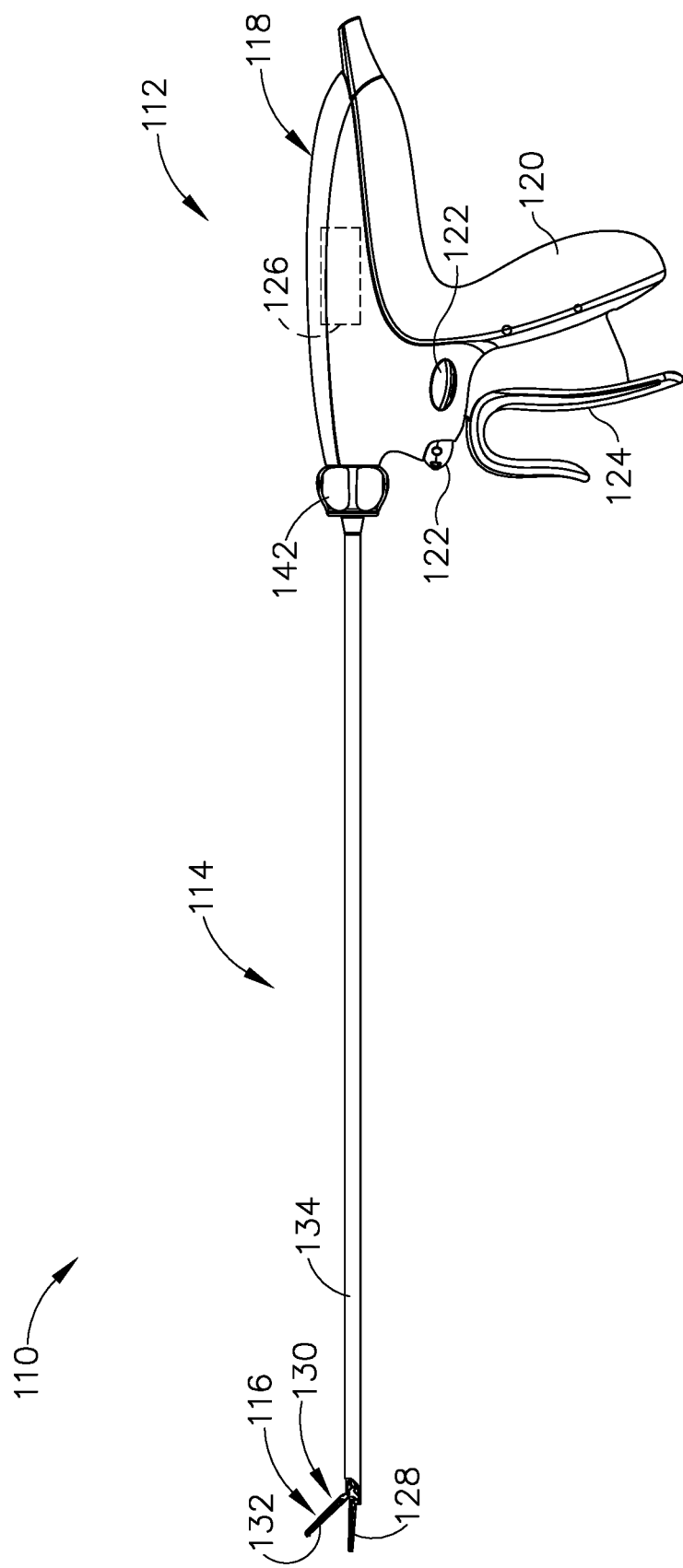
FIG. 3 depicts a side view of a second exemplary ultrasonic surgical instrument having a handle assembly and a shaft assembly with an end effector.
Figure 4A:
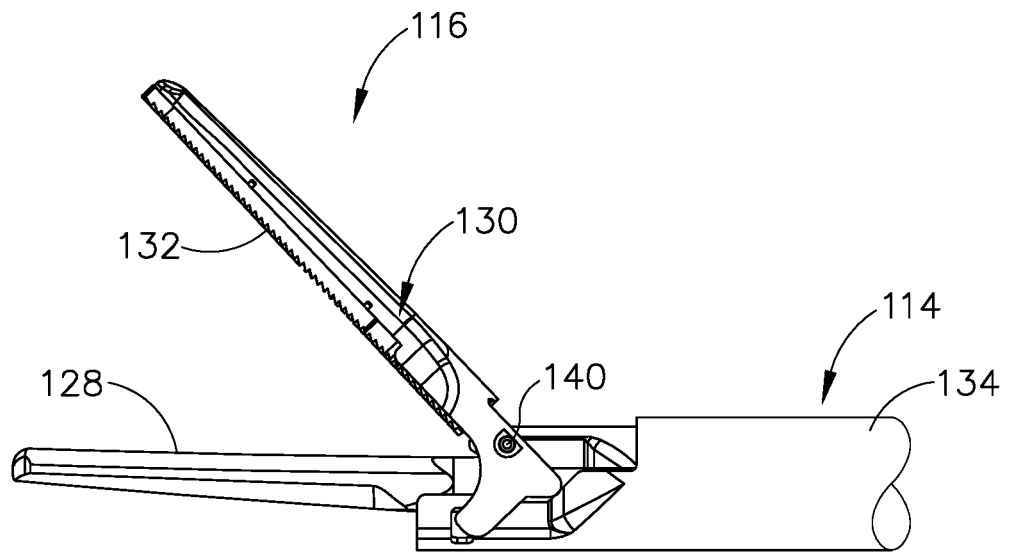
FIG. 4A depicts an enlarged side view of the end effector of FIG. 3 in an open configuration.
Figure 4B:
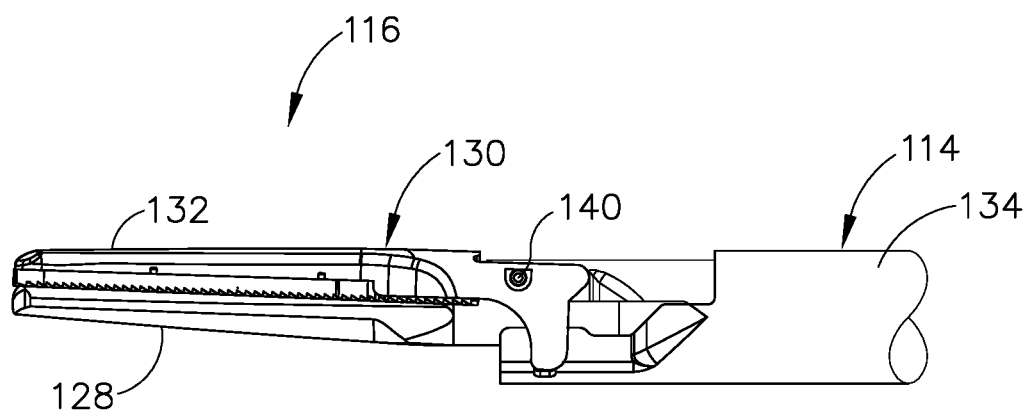
FIG. 4B depicts the enlarged side view of the end effector similar to FIG. 4A, but with the end effector in a closed configuration.

FIGS. 3-4B show an exemplary ultrasonic surgical instrument (110) that includes a first modular assembly shown as a handle assembly (112), a second modular assembly shown as a shaft assembly (114) extending distally from handle assembly (112), and an end effector (116) arranged at a distal end of shaft assembly (114). Handle assembly (112) comprises a body (118) including a pistol grip (120) and energy control buttons (122) configured to be manipulated by a surgeon to control various aspects of tissue treatment energy delivered by surgical instrument (110). A trigger (124) is coupled to a lower portion of body (118) and is pivotable toward and away from pistol grip (120) to selectively actuate end effector (116). In other suitable variations of surgical instrument (110), handle assembly (112) may comprise a scissor grip configuration, for example. Body (118) houses an ultrasonic transducer (126), shown schematically in FIG. 3, configured to deliver ultrasonic energy to end effector (116), as described in greater detail below. Body (118) may also be referred to herein as a housing (118) and may include one component or an assembly of components. The terms "body" and "housing" are thus not intended to unnecessarily limit the invention described herein to any number of discrete components.

As shown best in FIGS. 4A-4B, end effector (116) includes an ultrasonic blade (128) and a clamp arm (130) configured to selectively pivot toward and away from ultrasonic blade (128) for clamping tissue therebetween. Clamp arm (130) includes a clamp pad (132) arranged on a clamping side thereof and is moveable from an open position shown in FIG. 4A to a closed position shown in FIG. 4B. With respect to FIG. 3, ultrasonic blade (128) is acoustically coupled with ultrasonic transducer (126), which is configured to drive (i.e., vibrate) ultrasonic blade (128) at ultrasonic frequencies for cutting and/or sealing tissue positioned in contact with ultrasonic blade (128). Clamp arm (130) is operatively coupled with trigger (124) such that clamp arm (130) is configured to pivot toward ultrasonic blade (128), to the closed position, in response to pivoting of trigger (124) toward pistol grip (120). Further, clamp arm (130) is configured to pivot away from ultrasonic blade (128), to the open position in response to pivoting of trigger (124) away from pistol grip (120). Various suitable ways in which clamp arm (130) may be coupled with trigger (124) will be apparent to those of ordinary skill in the art in view of the teachings provided herein. In some versions, one or more resilient members may be incorporated to bias clamp arm (130) and/or trigger (124) toward the open position.

Shaft assembly (114) of the present example extends along a longitudinal axis and includes an outer tube (134), an inner tube (136) received within outer tube (134), and an ultrasonic waveguide (138) supported within and extending longitudinally through inner tube (136). Ultrasonic blade (128) is formed integrally with and extends distally from waveguide (138). A proximal end of clamp arm (130) is pivotally coupled to distal ends of outer and inner tubes (134, 136), enabling clamp arm (130) to pivot relative to shaft assembly (114) about a pivot axis defined by a pivot pin (140) (see FIGS. 4A-4B) extending transversely through the distal end of inner tube (136).

In the present example, inner tube (136) is longitudinally fixed relative to handle assembly (118), and outer tube (134) is configured to translate relative to inner tube (136) and handle assembly (118), along the longitudinal axis of shaft assembly (114). As outer tube (134) translates distally, clamp arm (130) pivots about its pivot axis toward its open position. As outer tube (134) translates proximally, clamp arm (130) pivots about its pivot axis in an opposite direction toward its closed position. Though not shown, a proximal end of outer tube (134) is operatively coupled with trigger (124) such that actuation of trigger (124) causes translation of outer tube (134) relative to inner tube (136), thereby opening or closing clamp arm (130) as discussed above. In other suitable configurations not shown herein, outer tube (134) may be longitudinally fixed and inner tube (136) may be configured to translate for moving clamp arm (130) between the open and closed positions. Various other suitable mechanisms for actuating clamp arm (130) between the open and closed positions will be apparent to those of ordinary skill in the art.

Figure 5:
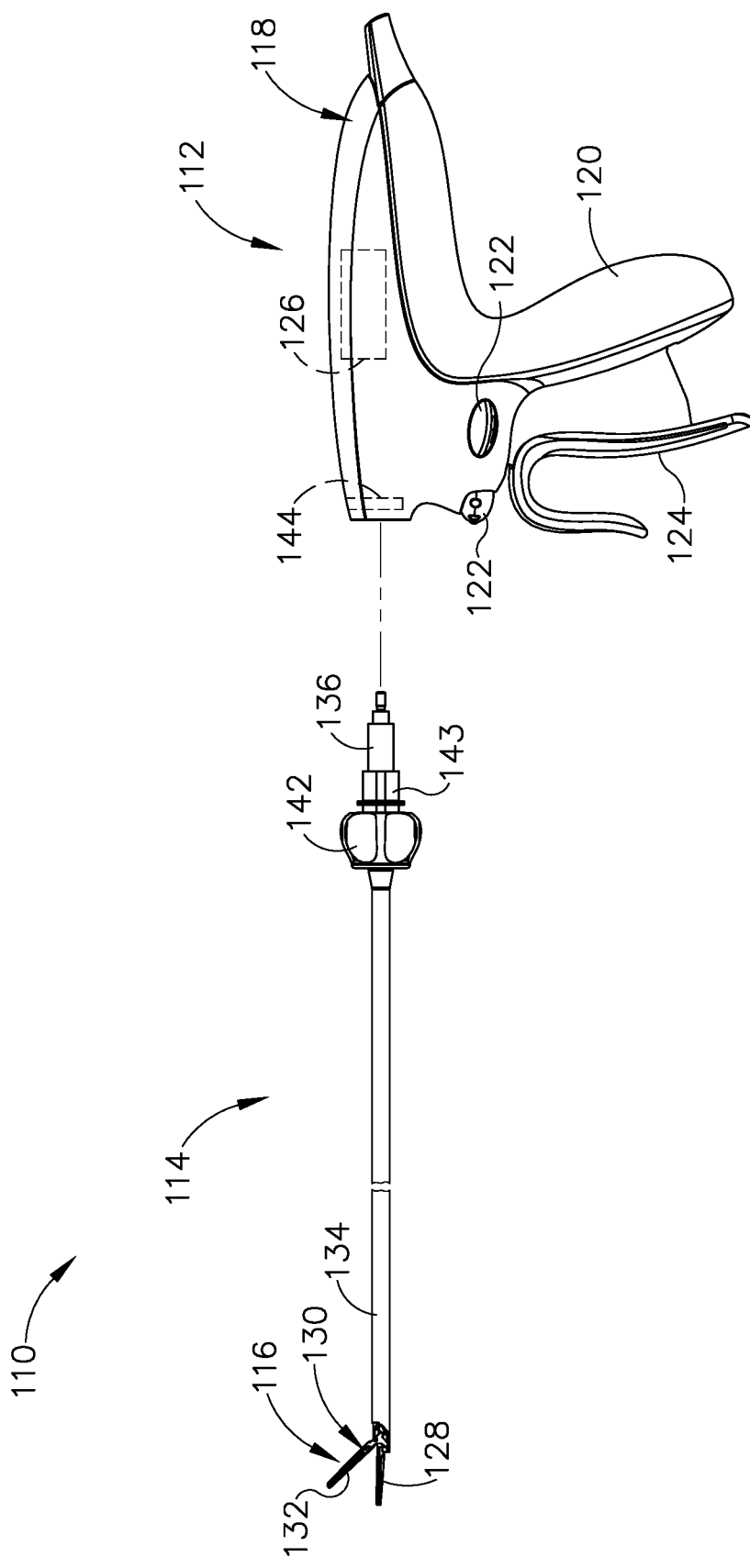
FIG. 5 depicts a partially exploded side view of the ultrasonic surgical instrument of FIG. 3.
Figure 6:
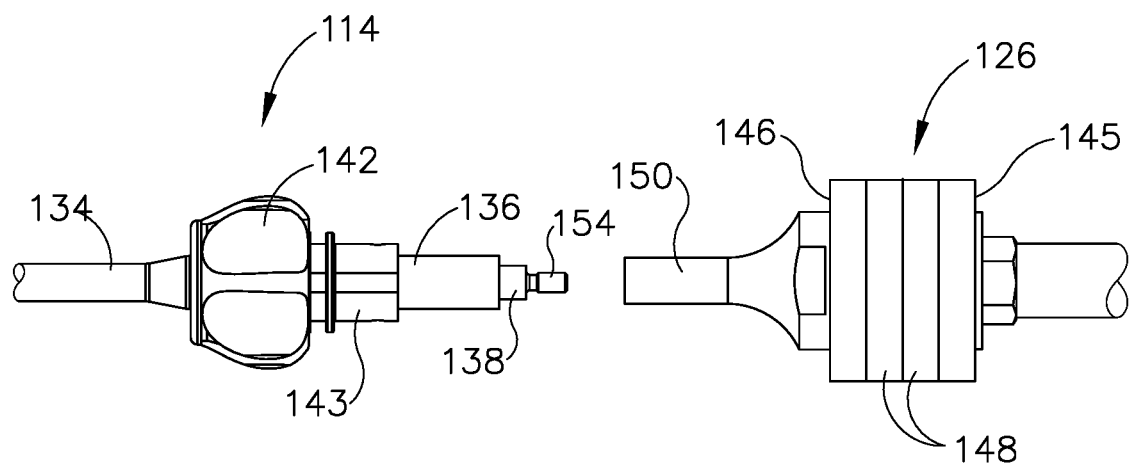
FIG. 6 depicts a partially schematic enlarged side view of an ultrasonic transducer, a waveguide, and a rotation knob of the ultrasonic surgical instrument of FIG. 3, showing attachment of the waveguide to the ultrasonic transducer.

Shaft assembly (114) and end effector (116) are configured to rotate together relative to body (118) about the longitudinal axis defined by shaft assembly (114). As shown in FIGS. 5-6, shaft assembly (114) further includes a rotation knob (142) arranged at a proximal end thereof as well as a shaft coupler (143) configured to mechanically connect to body coupler (144) of handle assembly (112). Rotation knob (142) is rotatably coupled to body (118) of handle assembly (112) and is rotationally fixed to outer tube (134), inner tube (136), and waveguide (138) by a coupling pin (not shown) extending transversely therethrough. Coupling pin (not shown) is arranged at a longitudinal location corresponding to an acoustic node of waveguide (138). In other examples, rotation knob (142) may be rotationally fixed to the remaining components of shaft assembly (114) in various other manners. Rotation knob (142) is configured to be gripped by an operator to selectively manipulate the rotational orientation of shaft assembly (114) and end effector (116) relative to handle assembly (112). Various examples of acoustic and mechanical connections between shaft assembly (114) and handle assembly (112) are described in greater detail in U.S. patent application Ser. No. 15/644,930, entitled "Acoustic Drivetrain with External Collar at Nodal Position," filed on Jul. 10, 2017 and U.S. patent application Ser. No. 15/644,944, entitled "Features to Couple Acoustic Drivetrain Components in Ultrasonic Surgical Instrument," filed on Jul. 10, 2017, the disclosures of which are each incorporated by reference herein.

FIGS. 3-5 show additional details of ultrasonic transducer (126) and waveguide (138). In particular, ultrasonic transducer (126) and waveguide (138) are configured to threadedly couple together. Accordingly, waveguide (138) is configured to acoustically couple ultrasonic transducer (126) with ultrasonic blade (128), and thereby communicate ultrasonic mechanical vibrations from ultrasonic transducer (126) to blade (128). In this manner, ultrasonic transducer (126), waveguide (138), and ultrasonic blade (128) together define an acoustic assembly of ultrasonic surgical instrument (110). Ultrasonic transducer (126) is rotatably supported within body (118) of handle assembly (112) and is configured to rotate with shaft assembly (114), including waveguide (138), and end effector (116) about the longitudinal axis of shaft assembly (114).

Ultrasonic transducer (126) is electrically coupled with a generator (not shown), which may be provided externally of ultrasonic surgical instrument (110) or integrated within surgical instrument (110). During use, generator (not shown) powers ultrasonic transducer (126) to produce ultrasonic mechanical vibrations, which are communicated distally through waveguide (138) to ultrasonic blade (128). Ultrasonic blade (128) is caused to oscillate longitudinally in the range of approximately 10 to 500 microns peak-to-peak, for example, and in some instances in the range of approximately 20 to 200 microns, at a predetermined vibratory frequency $f_o$ of approximately 50 kHz, for example. Vibrating ultrasonic blade (128) may be positioned in direct contact with tissue, with or without assistive clamping force provided by clamp arm (130), to impart ultrasonic vibrational energy to the tissue and thereby cut and/or seal the tissue. For example, blade (128) may cut through tissue clamped between clamp arm (130) and a clamping side of blade (128), or blade (128) may cut through tissue positioned in contact with an oppositely disposed non-clamping side of blade (128) having an edge, for example during a "back-cutting" movement. In some versions, waveguide (138) may be configured to amplify the ultrasonic vibrations delivered to blade (128). Waveguide (138) may include various features operable to control the gain of the vibrations, and/or features suitable to tune waveguide (138) to a selected resonant frequency.

Figure 7:
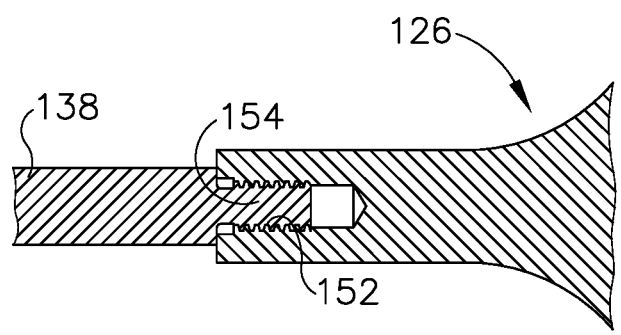
FIG. 7 depicts a partially schematic enlarged cross-sectional side view of a threaded coupling between the ultrasonic transducer and the waveguide of FIG. 6.

In the present example, ultrasonic transducer (26) includes a first resonator (or "end-bell") (145), a conically shaped second resonator (or "fore-bell") (146), and a transduction portion arranged between end-bell (145) and fore-bell (146) that includes a plurality of piezoelectric elements (148). A compression bolt (not shown) extends distally, coaxially through end-bell (145) and piezoelectric elements (148) and is threadedly received within a proximal end of fore-bell (146). A velocity transformer (or "horn") (150) extends distally from fore-bell (146) and includes an internally threaded bore (152) configured to receive and threadedly couple with an externally threaded proximal tip (154) of waveguide (38) as shown in FIGS. 6-7.

While the teachings herein are disclosed in connection with ultrasonic surgical instruments, it will be appreciated that they may also be employed in connection with surgical instruments configured to provide a combination of ultrasonic and radio frequency (RF) energies. Examples of such instruments and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

III. Alternative Exemplary Ultrasonic Surgical Instruments and Various Mechanical Lockout Assemblies Given that various portions of ultrasonic surgical instrument (10, 110) removably connect together, it may be desirable in various examples to reuse some portions of ultrasonic surgical instrument (10, 110) while replacing others upon reconnection for further use by the surgeon. For example, the first modular assembly (12, 112) in the present example is reusable whereas second modular assembly (14, 114) may be disconnected and replaced with an unused, replacement second modular assembly (14, 114). Since first modular assembly (12, 112) is separable from second modular assembly (14, 114), it is beneficial to ensure that first modular assembly (12, 112) and second modular assembly (14, 114) are correctly and completed assembled prior to use to prevent a malfunction or inadvertent separation of first modular assembly (12, 112) from second modular assembly (14, 114). For at least this reason, it may be desirable to incorporate a lockout assembly that prevents use of instrument (10, 110) when the first modular assembly (12, 112) and second modular assembly (14, 114) are not correctly and completed assembled together.

While the following mechanical lockout assemblies (216, 316, 416, 416', 544, 544', 644, 744, 844, 944, 1044, 1144, 1244) are shown in distinct positions between reusable and replaceable features for removable connection, any of the following mechanical lockout assemblies (216, 316, 416, 416', 544, 544', 644, 744, 844, 944, 1044, 1144, 1244), it will be appreciated that mechanical lockout assemblies (216, 316, 416, 416', 544, 544', 644, 744, 844, 944, 1044, 1144, 1244) may be incorporated into any surgical instrument described herein, exchanged, or moved so as to make one or more portions of a surgical instrument removable from a remainder of the surgical instrument. Two general forms of mechanical lockout varieties are shown and described below. First, a mechanical lockout assembly that that effectively locks the clamp arm, thereby preventing the operator from clamping on tissue with the end effector. Second, a mechanical lockout assembly that effectively locks the energy control buttons, thereby preventing the operator from activating the ultrasonic blade. As such, mechanical lockout assemblies (216, 316, 416, 416', 544, 544', 644, 744, 844, 944, 1044, 1144, 1244) are intended to cover both energy control button lockouts preventing activation of ultrasonic blade and trigger lockouts preventing closure of clamp arm assembly toward ultrasonic blade. It is also appreciated that one or more of these mechanical lockout assemblies (216, 316, 416, 416', 544, 544', 644, 744, 844, 944, 1044, 1144, 1244) may be used in combination with another mechanical lockout assemblies (216, 316, 416, 416', 544, 544', 644, 744, 844, 944, 1044, 1144, 1244).

The following description provides various examples of mechanical lockout assemblies. Such mechanical lockout assemblies (216, 316, 416, 416', 544, 544', 644, 744, 844, 944, 1044, 1144, 1244) described below may be used with any ultrasonic surgical instrument described above and below and in any of the various procedures described in the various patent references cited herein. To this end, like numbers below indicate like features described above. Except as otherwise described below, ultrasonic surgical instruments (210, 310, 410, 510, 610, 710, 810, 910, 1010, 1110, 1210) described below may be constructed and operable like instruments (10, 110) described above. Certain details of ultrasonic surgical instruments (210, 310, 410, 510, 610, 710, 810, 910, 1010, 1110, 1210) will therefore be omitted from the following description, it being understood that such details are already provided above in the description of instruments (10, 110). Other suitable ways in which various ultrasonic surgical instruments may be used will be apparent to those of ordinary skill in the art in view of the teachings herein.

Similarly, various electrical lockouts may be incorporated into any surgical instrument in conjunction with the following mechanical lockouts (216, 316, 416, 416', 544, 544', 644, 744, 844, 944, 1044, 1144, 1244). Such electrical lockouts are disclosed in U.S. App. No. 15/951,747, entitled "Electrical Lockout for Ultrasonic Surgical Instrument," filed on Apr. 12, 2018, published as U.S. Pub. No. 2019/0314054 on Oct. 17, 2019 the disclosure of which is incorporated by reference herein. Other suitable ways in which various ultrasonic surgical instruments may be used will be apparent to those of ordinary skill in the art in view of the teachings herein.

Figure 8:
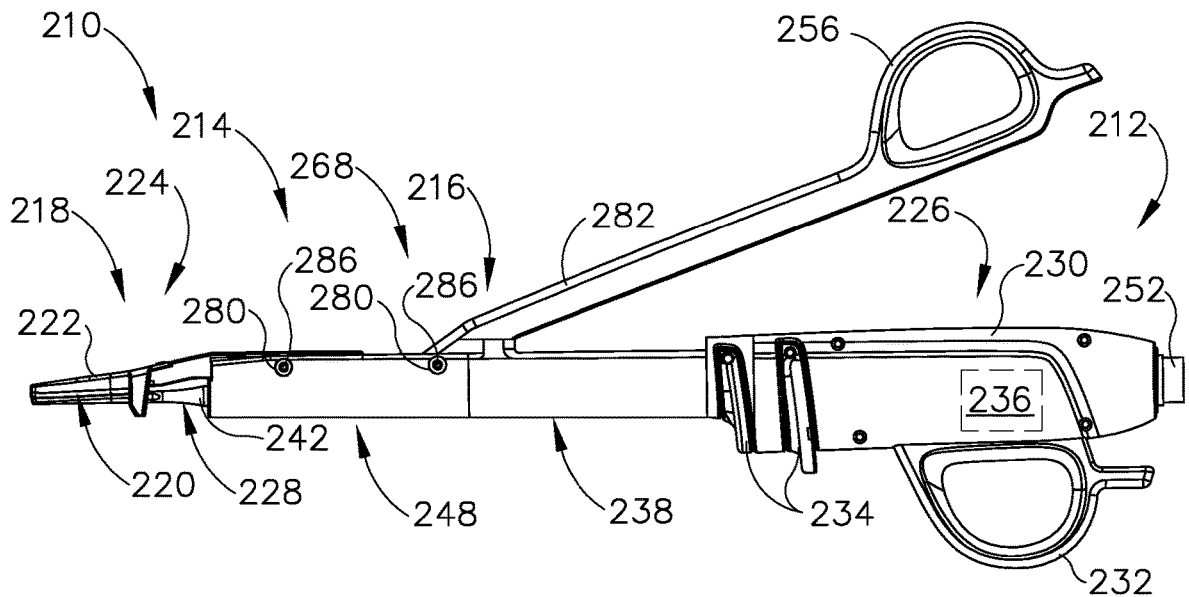
FIG. 8 depicts a schematic side view of a third exemplary ultrasonic surgical instrument.
Figure 9:
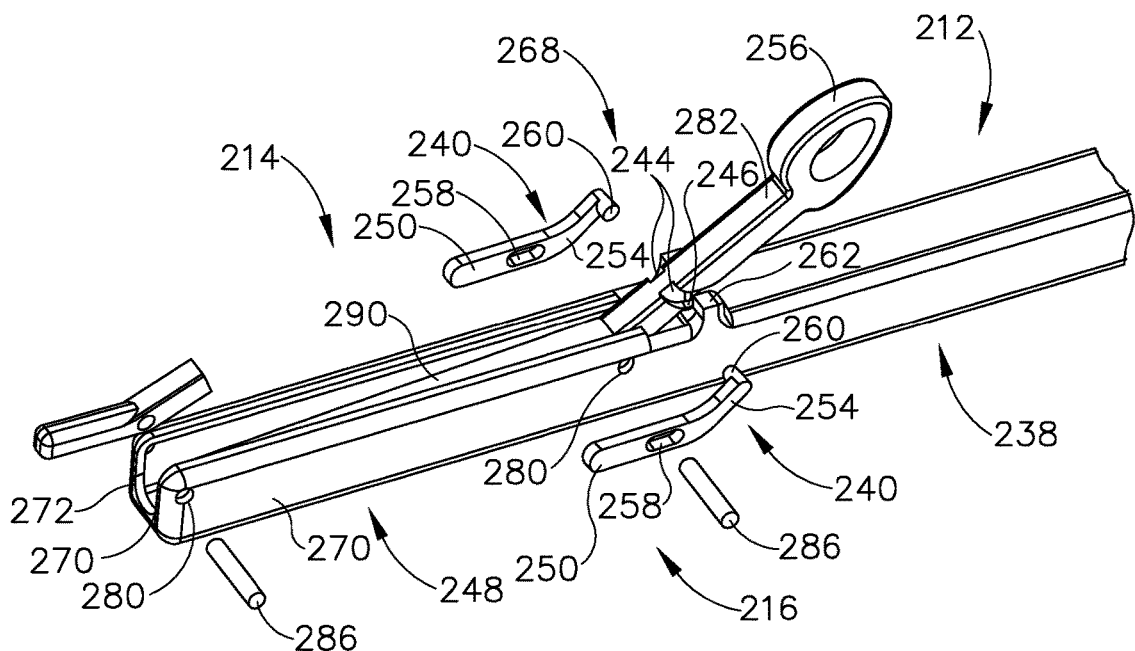
FIG. 9 depicts a schematic partially exploded perspective view of a portion of the instrument of FIG. 8 including a first exemplary mechanical lockout assembly.

A. Third Exemplary Ultrasonic Surgical Instrument Having a First Example of a Mechanical Lockout Assembly FIGS. 8-12 show a third exemplary ultrasonic surgical instrument (210) including a first mechanical lockout assembly (216). As shown in FIGS. 8-9, instrument (210) of the present example comprises a first modular assembly (212), a second modular assembly (214), an end effector (218), an ultrasonic blade (220), a clamp pad (222), a clamp pad assembly (224), a handle assembly (226), a shaft assembly (228), a body (230), a finger grip ring (232), a pair of buttons (234), an ultrasonic transducer (236), a proximal outer sheath (238), a waveguide (242), a distal outer sheath (248), a plug (252), a thumb grip ring (256), a clamp arm assembly (268), a U-shaped body (270), a distal face (272), a longitudinal pathway (278), a plurality of bores (280), an elongated arm (282), a plurality of pins (286), and an arm (290).

With reference to FIG. 8, first modular assembly (212) is configured to be removably coupled with second modular assembly (214). As shown, first modular assembly (212) includes handle assembly (226), ultrasonic transducer (236), energy control buttons (234), and proximal outer sheath (238), with ultrasonic transducer (236) being supported by first modular assembly (212). Waveguide (242) is acoustically coupled with ultrasonic transducer (236). Second modular assembly (214) includes waveguide (242), clamp arm assembly (268), distal outer sheath (248), and at least a portion of end effector (218), where end effector (218) extends distally from a distal end portion of second modular assembly (214).

FIG. 9 shows ultrasonic surgical instrument (210) also including at least one mechanical lockout assembly (216). Mechanical lockout assembly (216) is configured to enable switching between at least a locked configuration and an unlocked configuration. While FIG. 9 shows mechanical lockout assembly (216) including two distinct and separate lockout members (240), more or fewer lockout members (240) are also envisioned, including using only a single lockout member (240).

Figure 10A:
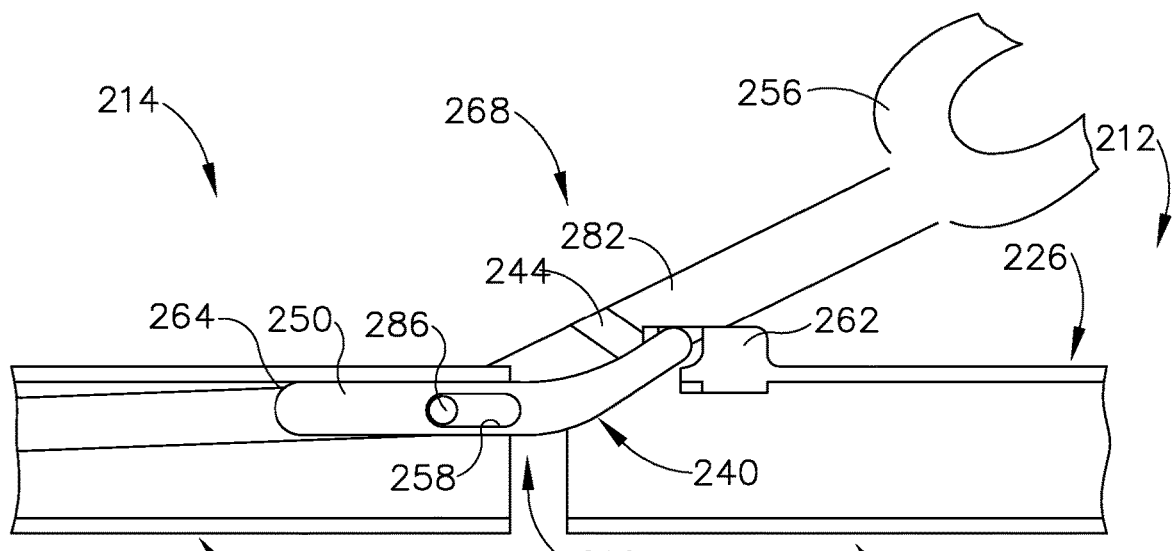
FIG. 10A depicts a schematic sectional view of the instrument similar to FIG. 9 in a locked configuration.
Figure 10B:
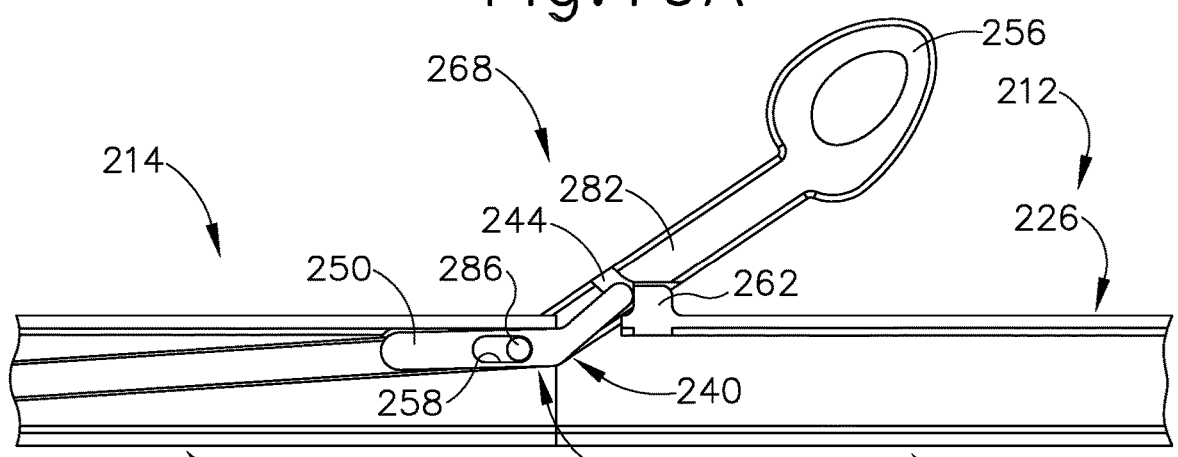
FIG. 10B depicts the schematic sectional view of the instrument similar to FIG. 9, but moving from the locked configuration to an unlocked configuration.
Figure 10C:
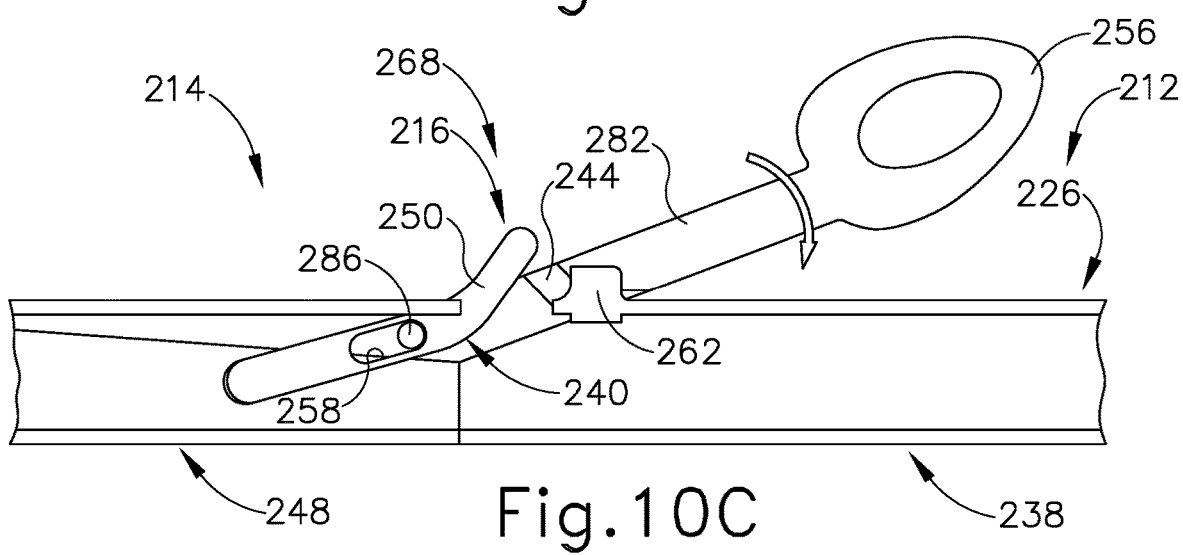
FIG. 10C depicts the schematic sectional view of the instrument similar to FIG. 9, but in the unlocked configuration.
Figure 11:
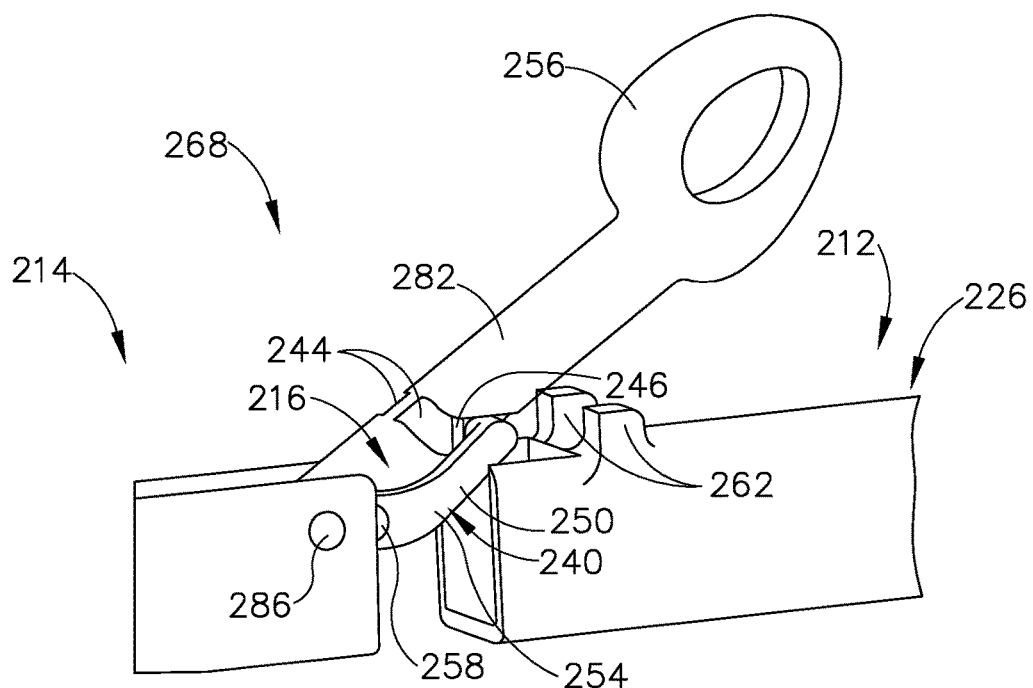
FIG. 11 depicts a schematic perspective view of the instrument similar to FIG. 10A in the locked configuration.
Figure 12:
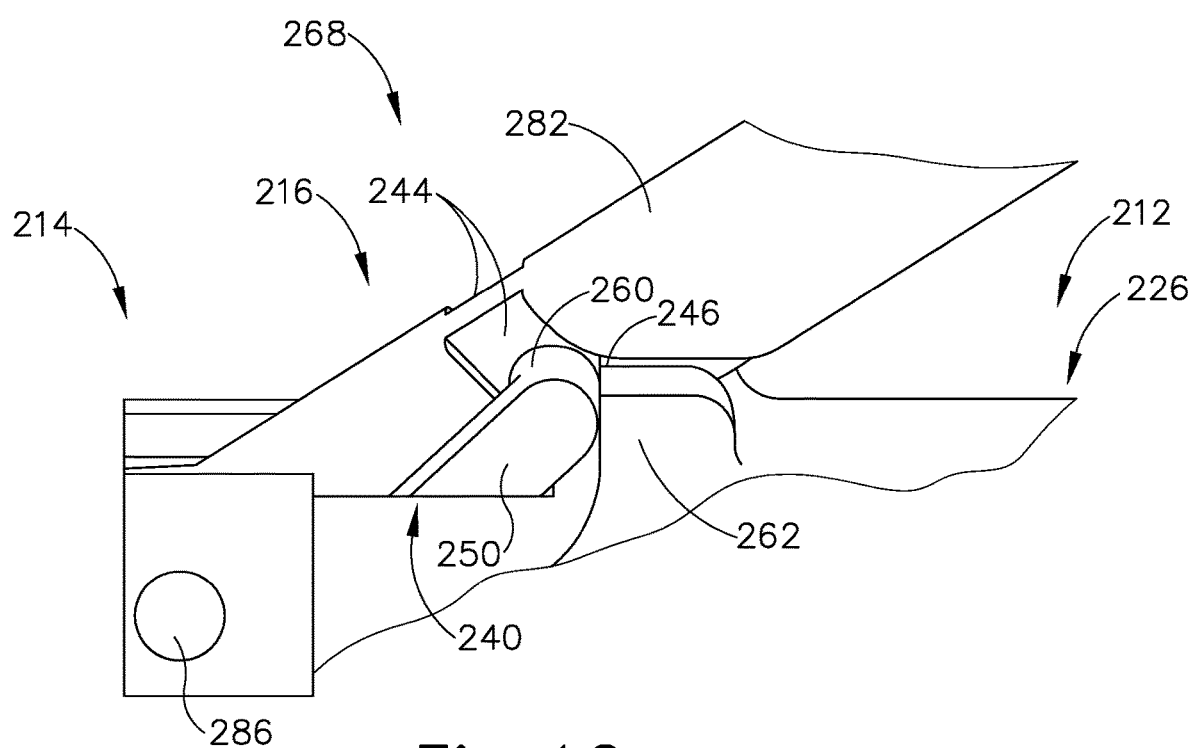
FIG. 12 depicts a schematic perspective view of the instrument similar to FIG. 10B still in the locked configuration, but moving to the unlocked configuration.

As best seen in FIGS. 9-12, clamp arm assembly (268) includes an elongate arm (282) and a thumb grip ring (256). As shown, clamp arm assembly (268) includes at least one cutout portion (244). Lockout member (240) is configured to move from the locked configuration to the unlocked configuration, while being at least partially contained within cutout portions (244). As shown in FIGS. 9, 11 and 12, cutout portions (244) may each include a protrusion (246) to inhibit translation of lockout member (240) while in the locked configuration. As will be described in greater detail below, while in the unlocked configuration, lockout member (240) is not contained within cutout portion (244).

FIG. 9 shows lockout member (240) as including a body (250) with a lockout feature having at least one of a curve (254), a change in angle, a slot (258), or a proximal projection (260) from body (250). Pin (286) pivotably couples distal outer sheath (248) with both clamp arm assembly (268) and lockout member (240). Proximal outer sheath (238) includes a projection (262) that displaces lockout member (240) distally when coupling proximal outer sheath (238) with distal outer sheath (248). As shown, lockout member (240) uses the same rotation point as clamp arm assembly (268).

FIG. 10A shows the locked configuration, where first modular assembly (212) and second modular assembly (214) are partially coupled together such that an operator is physically prevented from actuating clamp arm assembly (268). Mechanical lockout assembly (216) prevents the operator from clamping tissue with end effector (218). In the locked configuration, lockout member (240) prevents actuation of clamp arm assembly (268) due to interference with both elongated arm (282) of clamp arm assembly (268) and distal outer sheath (248). As shown, when the operator attempts to depress clamp arm assembly (268), lockout member (240) hits a top surface of projection (262) adjacent the top of distal outer sheath (248). This prevents clamping of end effector (218) on tissue when instrument (210) is not properly assembled. The operator cannot depress elongated arm (290) while lockout member (240) of mechanical lockout assembly (216) is in place.

FIG. 10B and FIG. 12 show an exemplary unlocking of instrument (210). As proximal outer sheath (238) is coupling with distal outer sheath (248), projection (262) on proximal outer sheath (238) translates lockout member (240) forward, past protrusion (246) on elongated arm (282). This effectively unlocks clamp arm assembly (268). Slot (258) in lockout member (240) allows for proximal displacement of pin (286), such that pin (286) slides within slot (258) allowing elongated arm (282) to pivot. Lockout member (240) translates distally away from projection (262) when moving from the locked configuration to the unlocked configuration.

FIG. 10C shows the unlocked configuration, where proximal outer sheath (238) is completely coupled with distal outer sheath (230), such that the operator is able to activate instrument (210). In the unlocked configuration, clamp arm assembly (268) freely rotates relative to locking member (264) and is not contained within cutout portion (244). Elongated arm (282) may be further depressed after unlocking instrument (210). The operator may fully clamp on tissue with end effector (218) after instrument (210) is fully assembled.

Additionally, in the locked configuration, instrument (210) allows for a method of maintaining the position of elongated arm (282) relative to distal outer sheath (248) to improve ease of assembly by the operator. Mechanical lockout assembly (216) holds elongated arm (282) of clamp arm assembly (268) in a position that will not impede assembly providing an additional benefit.

Figure 13:
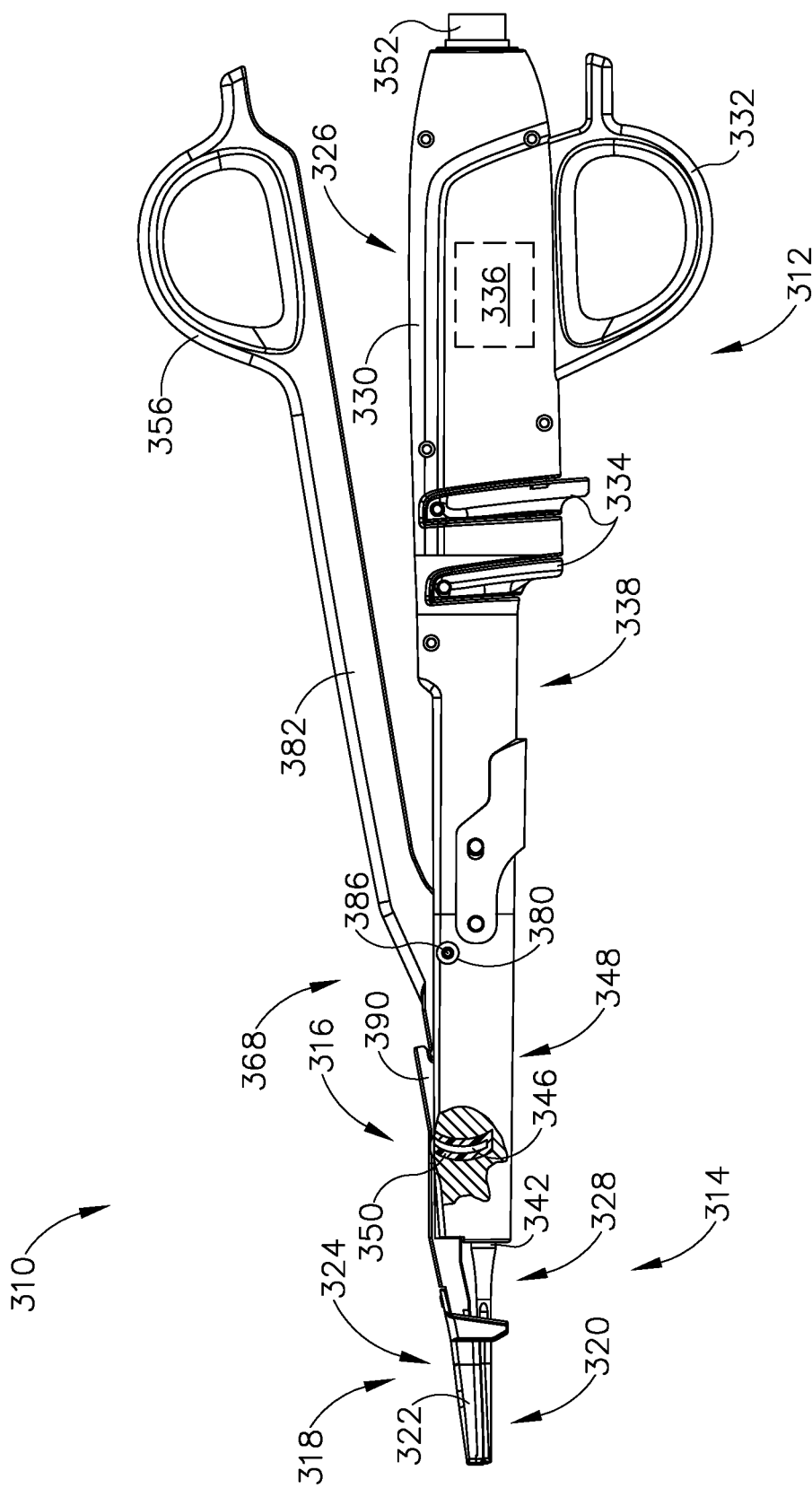
FIG. 13 depicts a schematic side view of a fourth exemplary ultrasonic surgical instrument in an unlocked configuration, with a portion of the outer sheath being shown in a cutaway to depict a second exemplary mechanical lockout assembly.

B. Fourth Exemplary Ultrasonic Surgical Instrument Having a Second Example of a Mechanical Lockout Assembly FIGS. 13-15 show a fourth exemplary ultrasonic surgical instrument (310) including a second mechanical lockout assembly (316). FIG. 13 of the present example shows that instrument (310) comprises a first modular assembly (312), a second modular assembly (314), an end effector (318), an ultrasonic blade (320), a clamp pad (322), a clamp pad assembly (324), a handle assembly (326), a shaft assembly (328), a body (330), a finger grip ring (332), a pair of buttons (334), an ultrasonic transducer (336), a proximal outer sheath (338), a waveguide (342), a distal outer sheath (348), a plug (352), a thumb grip ring (356), a clamp arm assembly (368), a U-shaped body (370), a distal face (372), a longitudinal pathway (378), a plurality of bores (380), an elongated arm (382), a camming protrusion (384), a plurality of pins (386), an arm (390), and a camming recess (392).

FIG. 13 shows first modular assembly (312) configured to be removably coupled with second modular assembly (314). First modular assembly (312) includes handle assembly (326), ultrasonic transducer (336), and proximal outer sheath (338), with ultrasonic transducer (336) being supported by first modular assembly (312). Waveguide (342) is acoustically coupled with ultrasonic transducer (336). Second modular assembly (314) includes waveguide (342), clamp arm assembly (368), distal outer sheath (348), and at least a portion of end effector (318). End effector (318) extends distally from a distal end portion of second modular assembly (214).

With continued reference to FIG. 13, mechanical lockout assembly (316) enables switching between at least an unlocked configuration and a locked configuration. Mechanical lockout assembly (316) includes at least one projection (340) operatively coupled with clamp arm assembly (368). Projection (346), coupled with arm (390), is configured to mate clamp arm assembly (368) with at least one recess (350) in distal outer sheath (348) to ensure proper alignment throughout closing. FIG. 15 shows a top down view of recesses (350) in distal outer sheath (348). While projections (346) and recesses (350) are shown as curvilinear, other shapes are also envisioned.

Figure 14A:
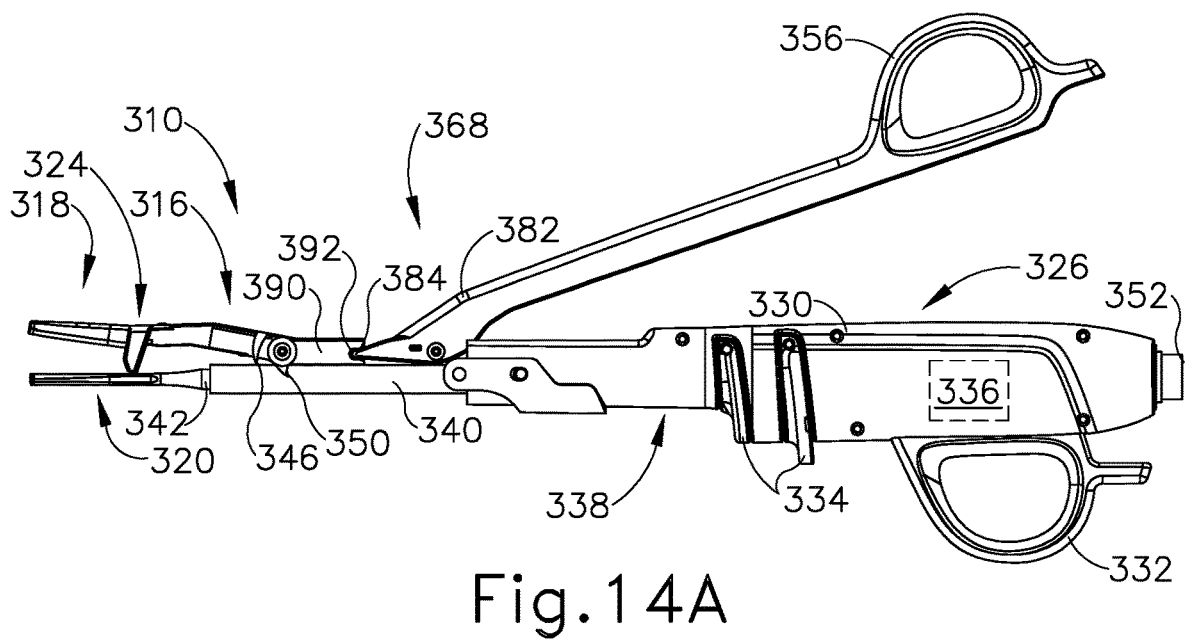
FIG. 14A depicts a schematic side view of the instrument similar to FIG. 13, but in a locked configuration with cutouts in the outer sheath.

FIG. 14A shows instrument (310) in the locked configuration, where first modular assembly (312) and second modular assembly (314) are partially coupled together, such that the operator is physically prevented from activating instrument (310). More specifically, FIG. 14A shows arm (390) pivoted away such that the clamp pad (322) is spaced away from ultrasonic blade (320). Distal outer sheath (348) has been hidden in FIGS. 14A-14B for improved clarity. In the locked configuration, projection (346) is not received by corresponding recess (350) in distal outer sheath (348). As a result, projection (346) prevents the operator from being able to clamp down on tissue with end effector (318). In other words, in the locked configuration, ultrasonic blade (320) and clamp pad (322) are unable to approach each other when projection (346) is not aligned with the recess (350). Unless projection (346) is aligned with recess (350), projection (346) provides a hard stop preventing clamp arm assembly (368) from pivoting toward ultrasonic blade (320). While two recesses (350) are shown to capture two corresponding projections (346), more or fewer projections (346) and corresponding recesses (350) are also envisioned.

Figure 14B:
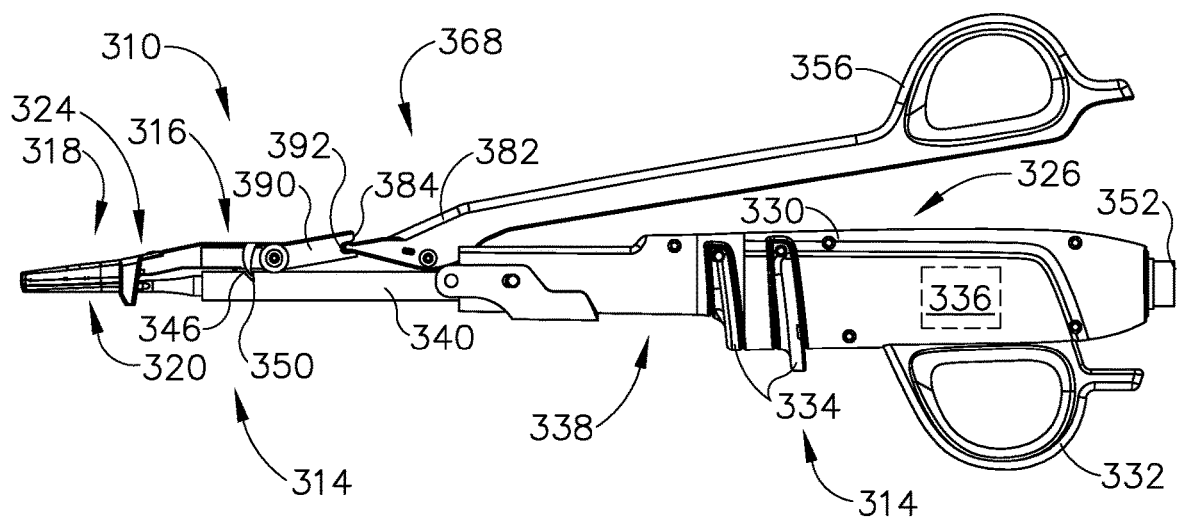
FIG. 14B depicts the schematic side view of the instrument similar to FIG. 14A, but in an unlocked configuration with cutouts in the outer sheath.
Figure 15:
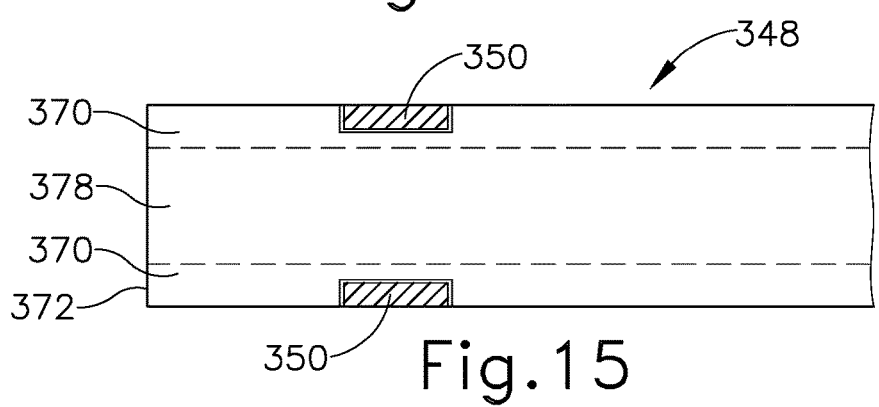
FIG. 15 depicts a schematic top view of the outer sheath and the associated cutouts of FIG. 13.

FIG. 14B shows instrument (310) in the unlocked configuration, where first modular assembly (212) and second modular assembly (314) are completely coupled together and the operator is able to activate instrument (310) using clamp arm assembly (368). In the unlocked configuration, projection (340) is received by corresponding recess (350) in distal outer sheath (348) allowing instrument (10) to be activated. In the unlocked configuration, projection (346) no longer provides a hard stop, thereby allowing clamp arm assembly (368) to pivot towards ultrasonic blade (320). It is beneficial that clamp arm assembly (368) be precisely longitudinally aligned with ultrasonic blade (320).

Figure 16A:
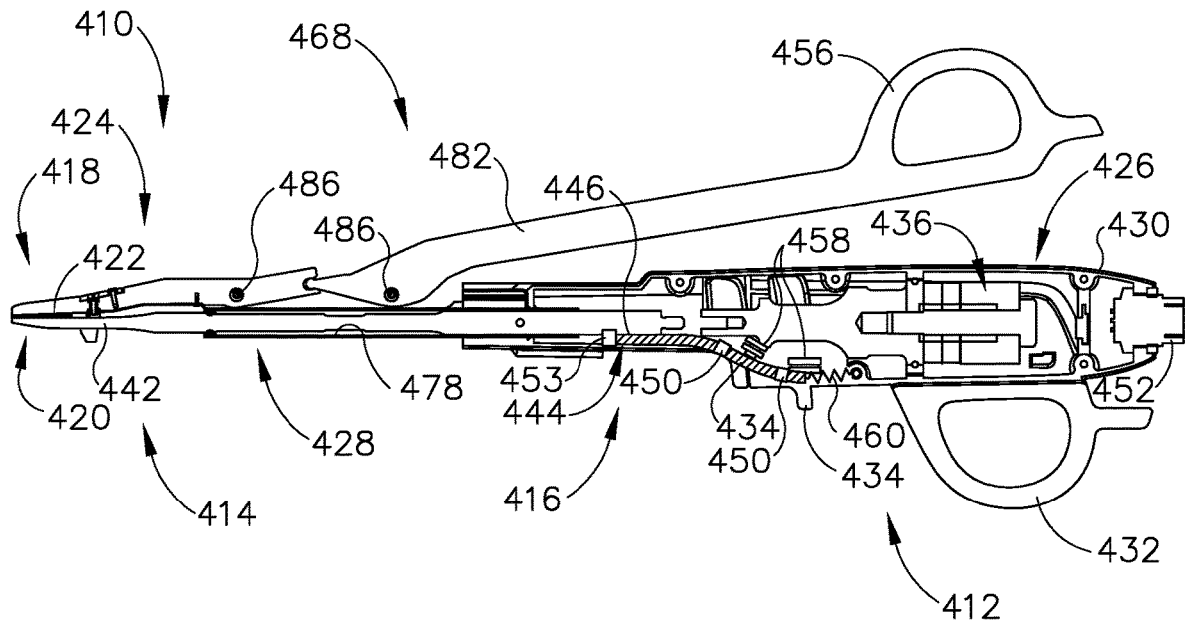
FIG. 16A depicts a schematic side view of a fifth exemplary ultrasonic surgical instrument including a third exemplary mechanical lockout assembly in a locked configuration.
Figure 16B:
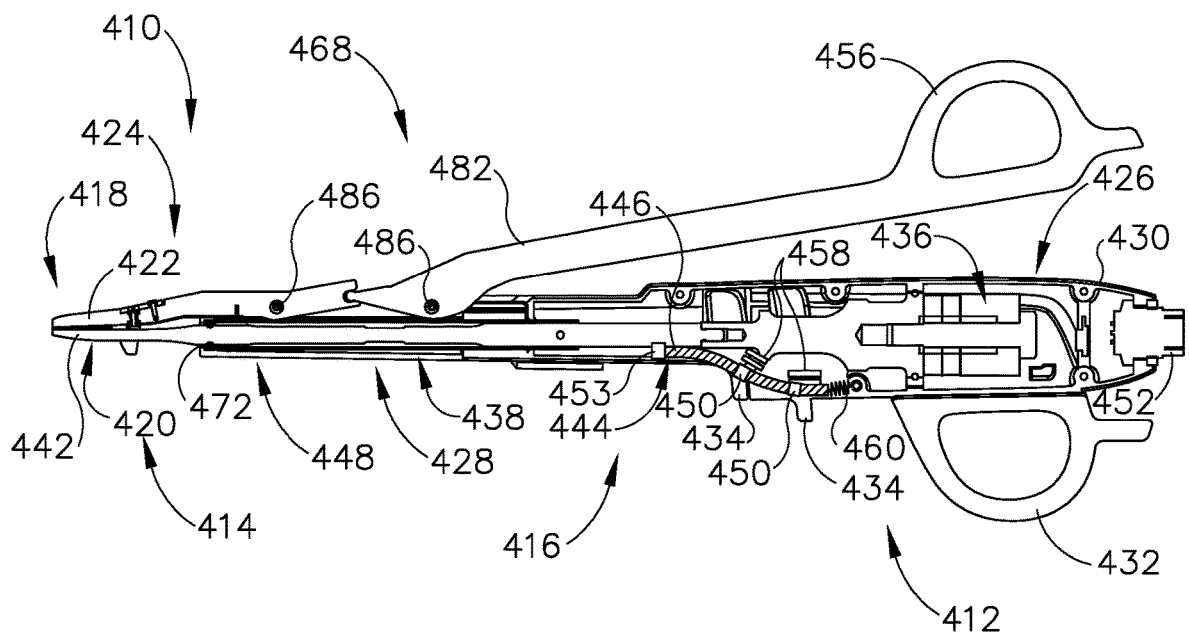
FIG. 16B depicts the schematic side view of the instrument similar to FIG. 16A, but in an unlocked configuration.

C. Fifth Exemplary Ultrasonic Surgical Instrument Having a Third Example of a Mechanical Lockout Assembly FIGS. 16A-16B show a fifth exemplary ultrasonic surgical instrument (410) including a third mechanical lockout assembly (416). FIG. 16A of the present example shows that instrument (410) comprises a first modular assembly (412), a second modular assembly (414), an end effector (418), an ultrasonic blade (420), a clamp pad (422), a clamp pad assembly (424), a handle assembly (426), a shaft assembly (428), a body (430), a finger grip ring (432), one or more energy control buttons (434), an ultrasonic transducer (436), a proximal outer sheath (438), a waveguide (442), a distal outer sheath (448), a plug (452), a thumb grip ring (456), a clamp arm assembly (468), a distal face (472), a longitudinal pathway (478), an elongated arm (482), a plurality of pins (486), and an arm (490).

FIGS. 16A-16B show first modular assembly (412) configured to be removably coupled with second modular assembly (414). As shown, first modular assembly (412) includes handle assembly (426), ultrasonic transducer (436), energy control button (434), and proximal outer sheath (438). Ultrasonic transducer (436) is supported by first modular assembly (412). Waveguide (442) is acoustically coupled with ultrasonic transducer (436). Second modular assembly (414) includes waveguide (442), clamp arm assembly (468), distal outer sheath (448), and at least a portion of end effector (418). End effector (418) extends distally from a distal end portion of second modular assembly (414).

FIGS. 16A-16B show mechanical lockout assembly (416) configured to enable switching between at least an unlocked configuration and a locked configuration. Mechanical lockout assembly (416) locks out instrument (410), so that instrument (410) cannot be activated by energy control buttons (434). Mechanical lockout assembly (416) includes a barrier (444) that includes a body portion (446) and at least one aperture (450). Barrier (444) is operatively coupled to shaft assembly (428) using a coupling mechanism (453), such that barrier (444) translates between the locked configuration and the unlocked configuration. Barrier (444) may be made from any material having lateral flexibility yet also have substantial column strength to be urged longitudinally along instrument (410). Handle assembly (426) includes a passageway (455) extending between energy control button (434) and a switch (458). While two energy control buttons (434) and two switches (458) are shown, more or fewer energy control buttons (434) and switches (458) are envisioned, for example, one or three. While not shown, the number of energy control button (434) and switches (458) may vary.

FIG. 16A shows instrument (410) in the locked configuration, where first modular assembly (412) and second modular assembly (414) are partially coupled together, such that the operator is physically prevented from activating instrument (410) using energy control buttons (434). As shown, mechanical lockout assembly (416) prevents activation of energy control buttons (434) by obstructing completion of the electrical circuit until the shaft assembly (428) is fully seated. Body portion (446) is disposed between energy control button (434) and switch (458), thereby providing a physical obstruction that prevents energy control button (434) from actuating switch (458). Mechanical lockout assembly (416) also includes a resilient element, shown as a spring (460), to return mechanical lockout assembly (416) to the locked configuration, when shaft assembly (428) is subsequently removed. When second modular assembly (412), which may be a disposable portion of instrument (410), in inserted together with first modular assembly (412), which may be a reusable portion of instrument (410), barrier (444) translates proximally. As shown, the entire barrier (444) translates proximally. This translation of barrier (444) allows energy control buttons (434) to mechanically actuate switches (458) to activate instrument (410). At least one of energy control buttons (434) or switches (458) may enter into passageway (455).

FIG. 16B shows the unlocked configuration, where first modular assembly (412) and second modular assembly (414) are completely coupled together and the operator is able to activate instrument (410) using energy control buttons (434). In the unlocked configuration, apertures (450) are disposed between energy control buttons (434) and switches (458), enabling buttons (434) to actuate switches (458).

Figure 17:
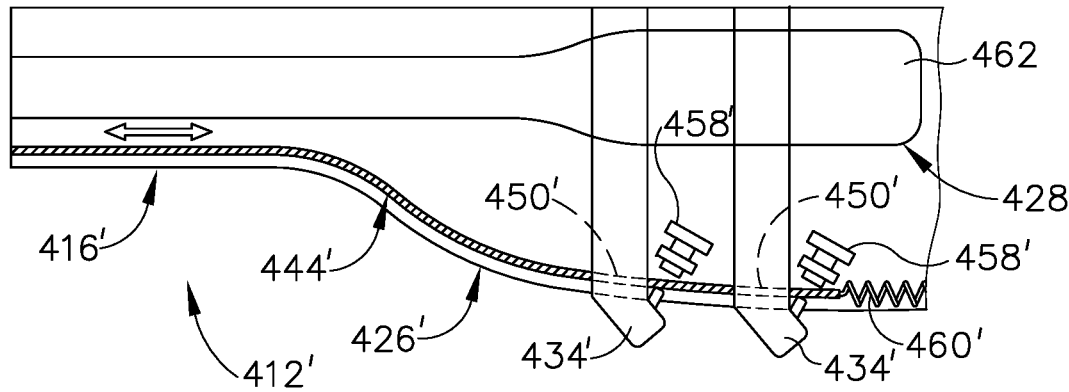
FIG. 17 depicts a schematic side sectional view of a portion of the instrument similar to FIG. 16A, but including a fourth exemplary mechanical lockout assembly in an unlocked configuration.

D. Fifth Exemplary Ultrasonic Surgical Instrument Having a Fourth Example of a Mechanical Lockout Assembly FIGS. 17-18B show various sectional views of another exemplary embodiment of a fourth mechanical lockout assembly (416'). FIG. 17 shows barrier (444') passing below acoustic drivetrain (462) and between energy control buttons (434') and switches (458') in handle assembly (426').

Figure 18A:
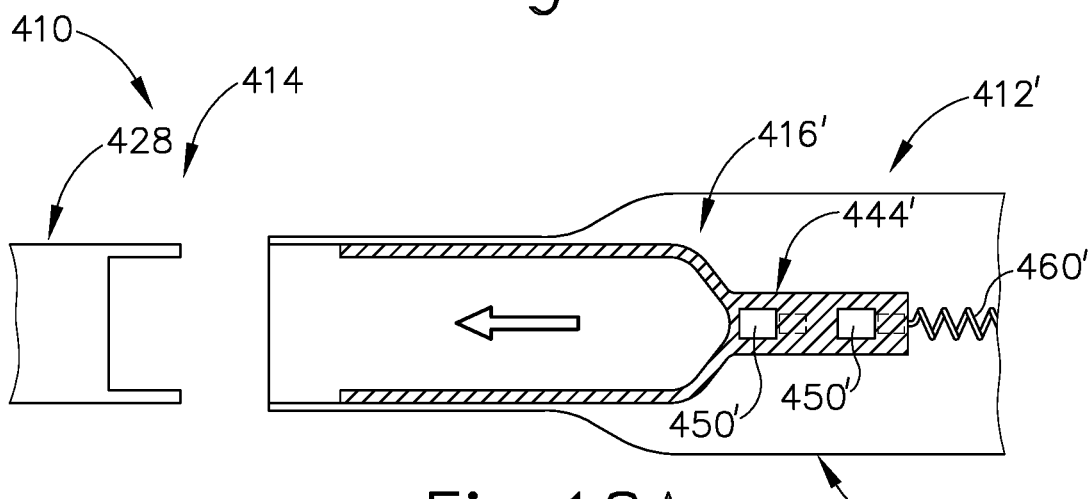
FIG. 18A depicts a schematic top sectional view of a portion of the instrument similar to FIG. 17 in a locked configuration.
Figure 18B:
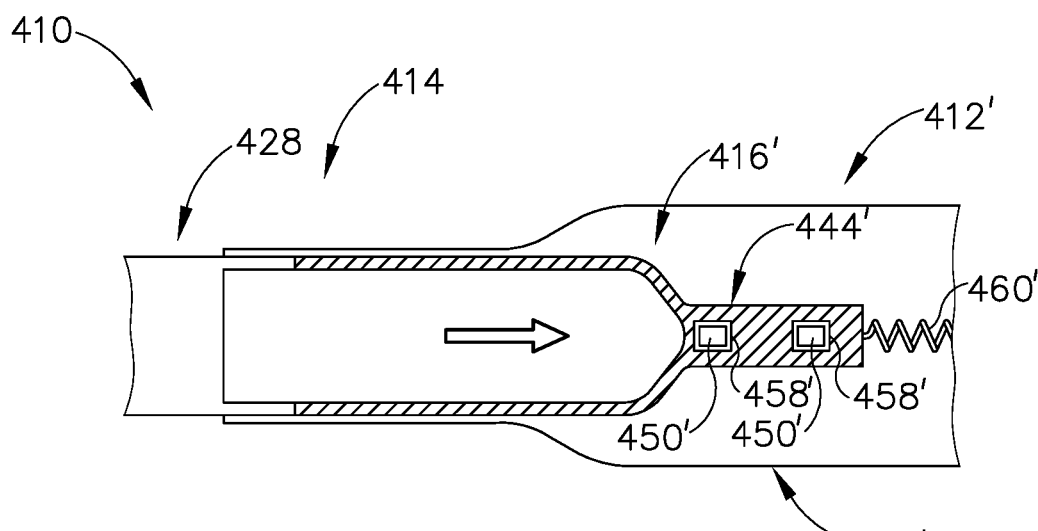
FIG. 18B depicts a schematic top sectional view of the instrument similar to FIG. 17, but in the unlocked configuration.

FIG. 18A shows that first modular assembly (412') may be a reusable portion, second modular assembly (414') may be a disposable portion, and spring (460') pushes barrier (444') forward when in the locked configuration, preventing activation of instrument (410). Switches (458') are blocked from being pressed by energy control buttons (434') by barrier (444').

FIG. 18B shows where mechanical lockout assembly (416') is pressed inward by disposable second modular assembly (414'). Apertures (450'), shown as windows, are now positioned between switches (458') and energy control buttons (434'), enabling energy control buttons (434') to press through barrier (444') into switches (458') to activate instrument (410') in the unlocked configuration.

Figure 19:
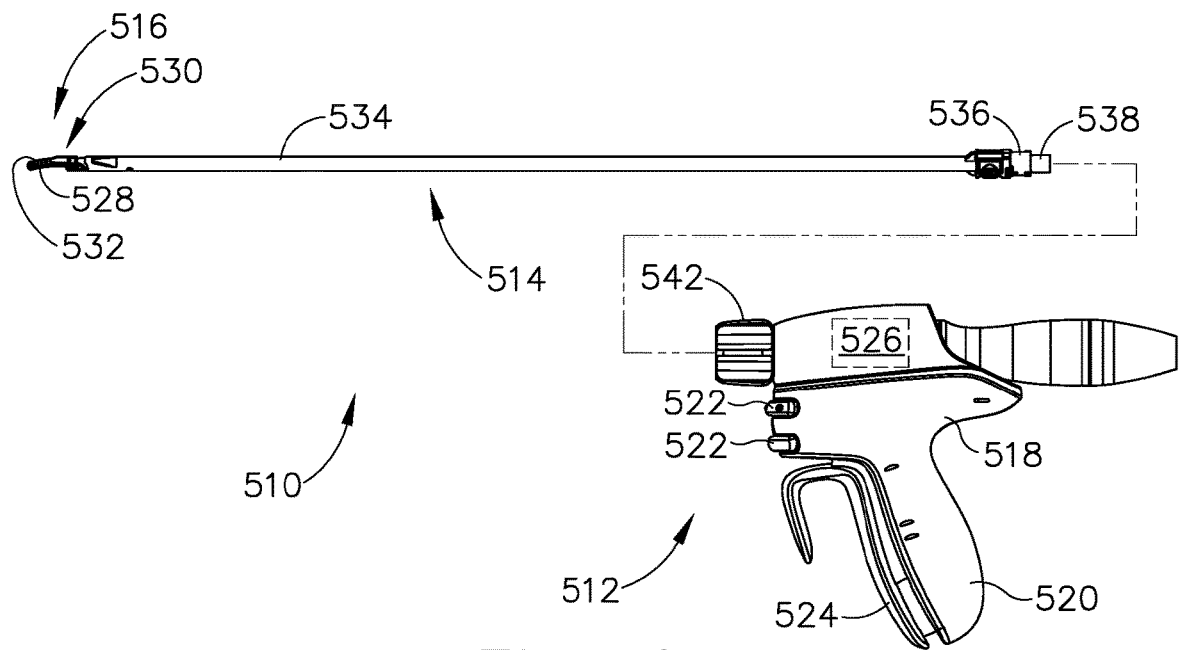
FIG. 19 depicts a schematic side view of a sixth exemplary ultrasonic surgical instrument.
Figures 20A, 20B:
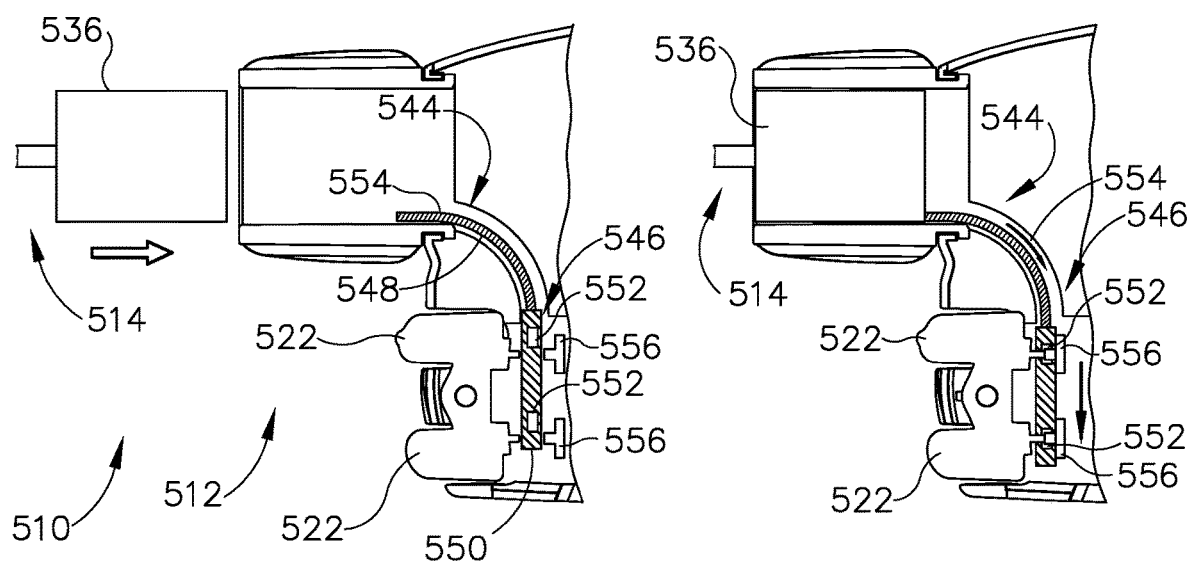
FIG. 20A depicts a schematic side sectional view of the instrument similar to FIG. 19 including a fifth exemplary mechanical lockout assembly in a locked configuration.
FIG. 20B depicts the schematic side sectional view of the instrument similar to FIG. 19, but in an unlocked configuration.

E. Sixth Exemplary Ultrasonic Surgical Instrument Having a Fifth Example of a Mechanical Lockout Assembly FIGS. 19-20B show a sixth exemplary ultrasonic surgical instrument (510) including a fifth mechanical lockout assembly (544). FIG. 19 shows ultrasonic surgical instrument (510) as comprising a first modular assembly shown as a handle assembly (512), a second modular assembly shown as a shaft assembly (514), an end effector (516), a body (518), a pistol grip (520), energy control buttons (522), a trigger (524), an ultrasonic transducer (526), an ultrasonic blade (528), a clamp arm (530), a clamp pad (532), an outer tube (534), an inner tube (536), an ultrasonic waveguide (538), and a rotation knob (542).

FIGS. 20A-20B show instrument (510) as including a mechanical lockout assembly (544). Mechanical lockout assembly (544) includes a barrier (546) that translates between a locked configuration and an unlocked configuration. Barrier (546) includes at least one body portion, with two body portions (548, 550) being shown in FIGS. 20A-20B. Body portion (550) includes at least one aperture (552) disposed within body portion (550), with two apertures (552) being shown in FIGS. 20A-20B. Barrier (546) is shown as a resilient elongated member that is disposed within handle assembly (512), however, barrier (546) may be operatively coupled to shaft assembly (514) and may be a variety of shapes and forms. Barrier (546) is laterally flexible and has sufficient column strength to drive body portion (550) without buckling. Handle assembly (512) includes energy control buttons (522) separated by a passageway (554) from switches (556). As shown in FIG. 20A, it is appreciated that aperture (550) may not extend completely through body portion (550) to enable energy control buttons (522) to mechanically actuate switches (556). As previously described with connection to the previous embodiment, while two energy control buttons (522) and two switches (556) are shown, more or fewer energy control buttons (522) and switches (556) are envisioned, for example, one or three. While not shown, the number of energy control button (534) and switches (556) may not be the same in some variations.

FIG. 20A shows instrument (510) in the locked configuration, where body portion (548) contacts and translates body portion (550) that is disposed between energy control buttons (522) and switches (556), preventing buttons (522) from activating switches (556), thereby preventing switches (556) from activating instrument (510). In moving to the unlocked configuration, barrier (546) is pushed by body portion (548) and translates into passageway (554) that extends between energy control buttons (522) and switches (556). In other words, the proximal portion of the shaft (514) pushes body portion (548), causing barrier (546) to translate into passageway (554) that extends between energy control buttons (522) and switches (556). As shown, engagement of shaft assembly (514) with handle assembly (512) pushes barrier (546) into a position that places apertures (550) in barrier (546) between energy control buttons (522) and switches (556).

FIG. 20B shows instrument (510) in the unlocked configuration, where apertures (552) are disposed between energy control buttons (522) and switches (556), enabling buttons (522) to activate switches (556), thereby enabling switches (556) to activate instrument (510). FIG. 20B shows where at least one of energy control button (522) or switch (556) extends at least partially within aperture (550) and contacts the other of energy control buttons (522) or switches (556) through aperture (550). FIG. 20B shows that the entire barrier (546) translates in passageway (554) towards energy control buttons (522) and switches (556). A spring (not shown), similar to spring (664) shown in FIGS. 22A-22B or spring (764) shown in FIGS. 24A-24B, or another suitable mechanism may be located at the bottom of barrier (546) to return barrier (546) to the locked configuration when shaft assembly (514) is removed from handle assembly (512).

Figure 21A:
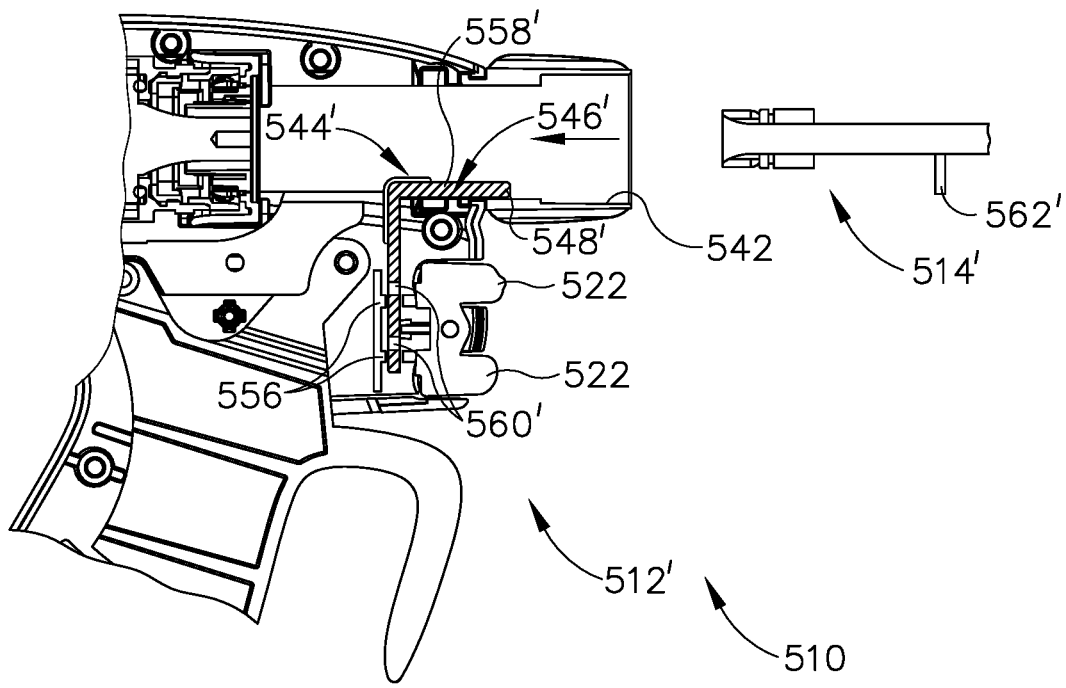
FIG. 21A depicts a schematic side sectional view of the instrument similar to FIG. 20A including a sixth exemplary mechanical lockout assembly in a locked configuration.
Figure 21B:
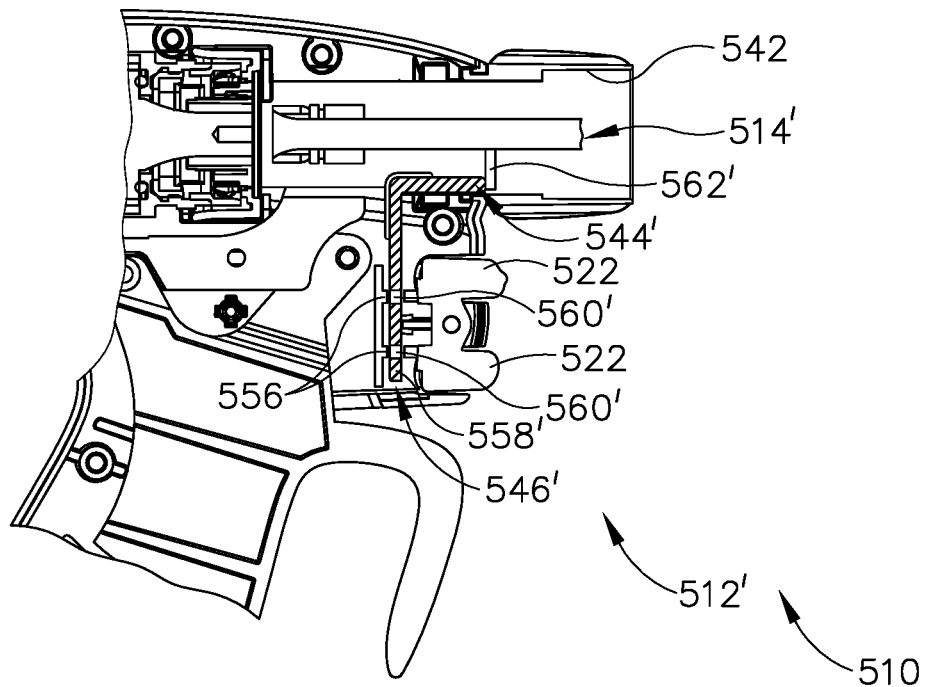
FIG. 21B depicts the schematic side sectional view of the instrument similar to FIG. 20B, but in an unlocked configuration.

F. Sixth Exemplary Ultrasonic Surgical Instrument Having a Sixth Example of a Mechanical Lockout Assembly FIGS. 21A-21B show another exemplary embodiment of a sixth mechanical lockout assembly (544'), where barrier (546') includes a single body portion (558') that includes apertures (560'). Additionally, apertures (560') extend completely through body portion (558') of barrier (546') in a generally perpendicular direction. Shaft assembly (514') includes a projection (562') that contacts barrier (546'), causing barrier (546') to translate, resulting in instrument (510) transitioning to the unlocked configuration, when shaft assembly (514') is fully coupled with handle assembly (512').

Figure 22A:
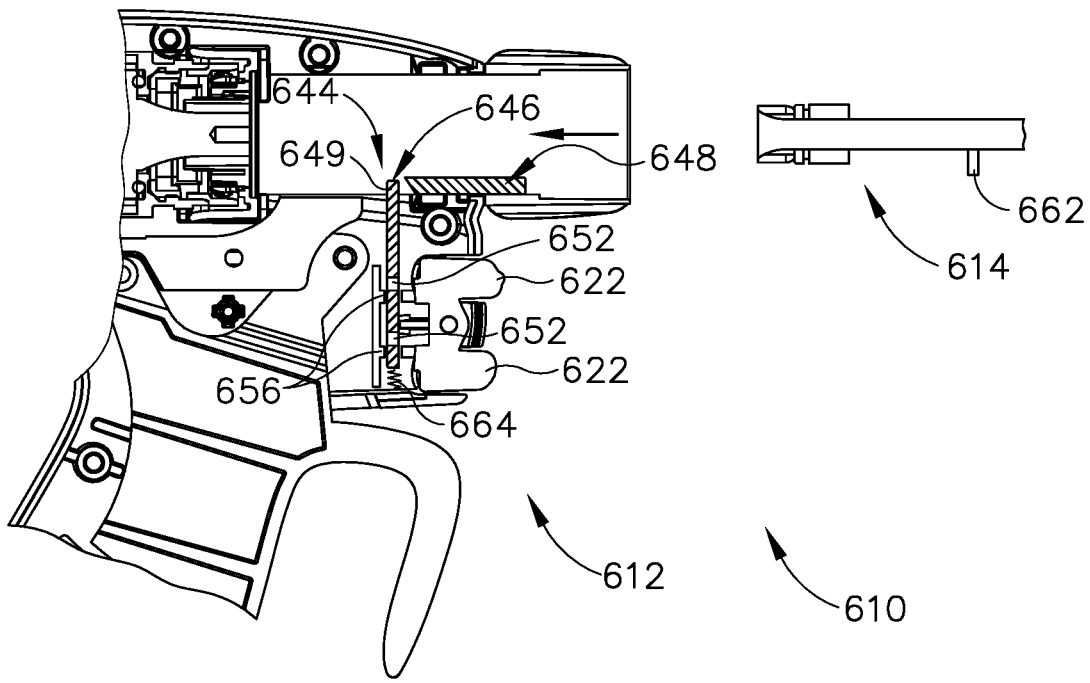
FIG. 22A depicts a schematic side view of a seventh exemplary ultrasonic surgical instrument including a seventh exemplary mechanical lockout assembly in a locked configuration.
Figure 22B:
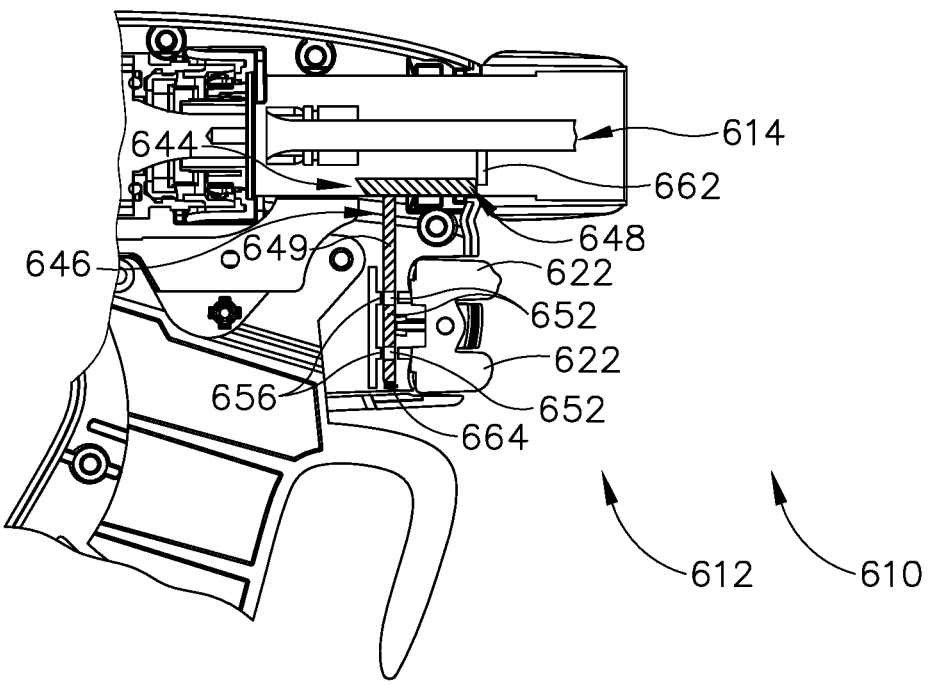
FIG. 22B depicts the schematic side view of the instrument similar to FIG. 22A, but in an unlocked configuration.

G. Seventh Exemplary Ultrasonic Surgical Instrument Having a Seventh Example of a Mechanical Lockout Assembly FIGS. 22A-22B show a seventh exemplary ultrasonic surgical instrument (610) including a seventh mechanical lockout assembly (644). Instrument (610) depicted in FIGS. 22A-22B is similar to instrument (510) depicted in FIGS. 21A-21B, with differences being briefly described below, and similarities being omitted. For example, instrument (610) includes a mechanical lockout assembly (644) that is different than mechanical lockout assembly (544) of instrument (510).

FIG. 22A shows instrument (610) in the locked configuration, where a first modular assembly is shown as a handle assembly (612) and a second modular assembly is shown as a shaft assembly (614) that are not completely coupled together. As a result, the operator is physically prevented from activating instrument (610) using energy control button (622) due to mechanical lockout assembly (644). As shown, mechanical lockout assembly (644) includes a barrier (646) such as a button lockout plate, and an angled slide (648), shaped as a wedge. Barrier (646) includes a body portion (649) and at least one aperture (652), with two apertures (652) being shown in FIG. 22A. In the locked configuration shown in FIG. 22A, barrier (646) is positioned such that apertures (652) are not interposed between buttons (622) and corresponding switches (656). Barrier (646) thus prevents buttons (622) from activating corresponding switches (656), thereby preventing activation of instrument (610).

Angled slide (648) of mechanical lockout assembly (644) is configured to be contacted by a projection (662) of shaft assembly (614) as shaft assembly (614) is coupled with handle assembly (612). As a result of being contacted by projection (662), angled slide (648) translates proximally and subsequently contacts barrier (646). The angled proximal end of slide (648) drives barrier (646) downwardly through a camming action. With barrier (646) in a downward position, apertures (652) are positioned between buttons (622) and corresponding switches (656), thereby providing clearance for buttons (622) to activate corresponding switches (656). Full coupling of shaft assembly (614) with handle assembly (612) thus causes instrument (610) to move from the locked configuration to the unlocked configuration.

FIG. 22B shows instrument (610) in the unlocked configuration, where handle assembly (612) and shaft assembly (614) are completely coupled together and the operator is able to activate instrument (610) using energy control button (622). Upon removal of shaft assembly (614), a resilient member, shown as a compression spring (664), causes barrier (646) to return to the locked configuration, where actuation of energy control buttons (622) is blocked from activating switches (656) by body portion (649) of barrier (646). Switches (656) may include button dome switches and corresponding printed circuit boards ("PCBs"). In the unlocked configuration, compression spring (664) is in a compressed state, whereas in the locked configuration (shown in FIG. 22A), compression spring (664) is in an extended state.

Figure 23:
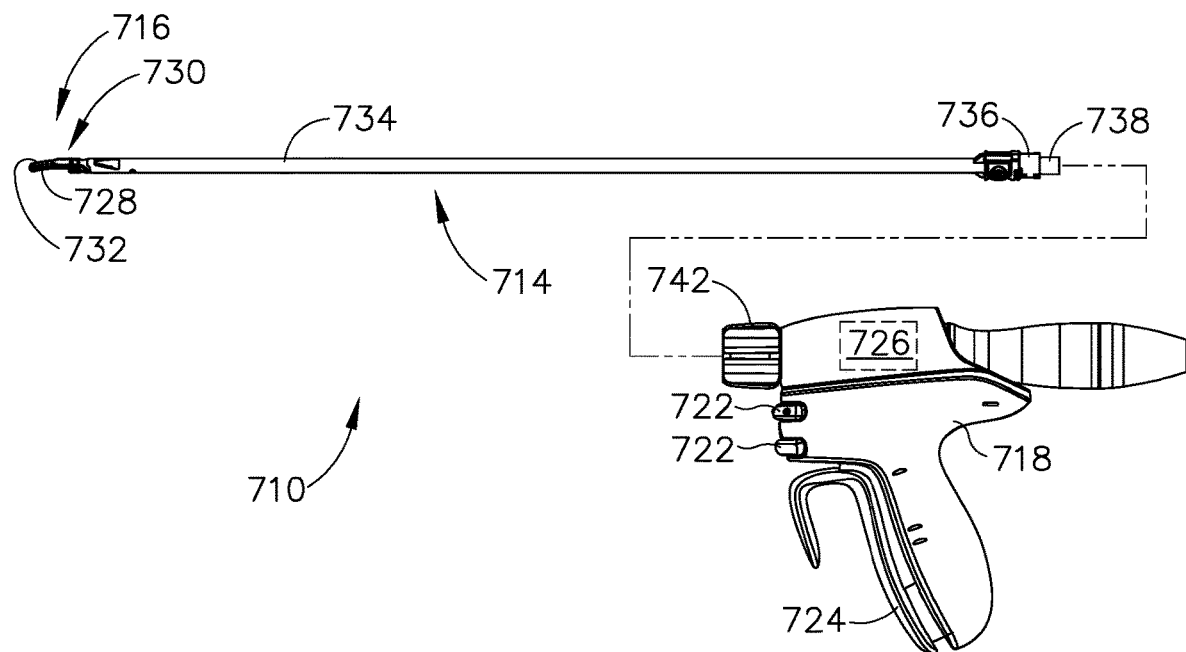
FIG. 23 depicts a schematic side view of an eighth exemplary ultrasonic surgical instrument.
Figure 25:
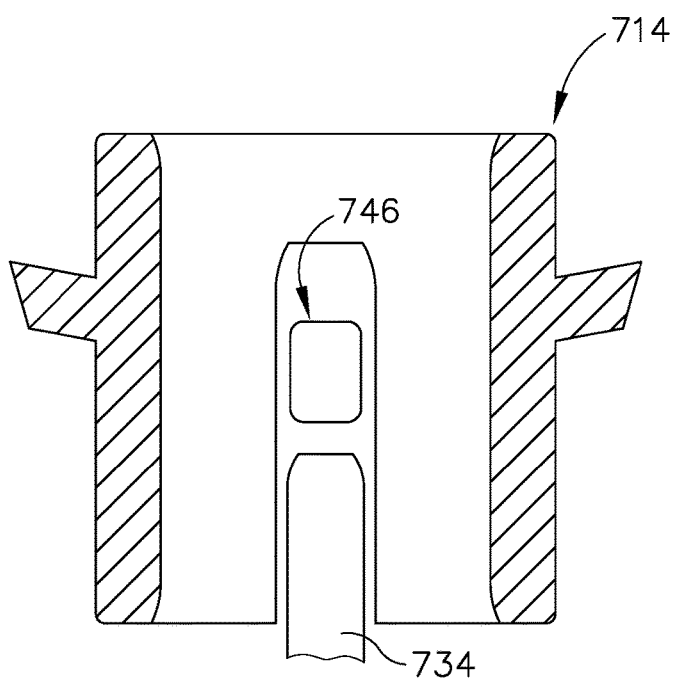
FIG. 25 is a schematic cross-sectional view of FIG. 24A taken along section line 25-25 of FIG. 24A in the locked configuration.

H. Eighth Exemplary Ultrasonic Surgical Instrument Having an Eighth Example of a Mechanical Lockout Assembly FIGS. 23-25 show an eighth exemplary ultrasonic surgical instrument (710) including an eighth mechanical lockout assembly (744). Instrument (710) of the present example comprises a first modular assembly shown as a handle assembly (712), a second modular assembly shown as a shaft assembly (714), an end effector (716), a body (718), a pistol grip (720), energy control buttons (722), a trigger (724), an ultrasonic transducer (726), an ultrasonic blade (728), a clamp arm (730), a clamp pad (732), an outer tube (734), an inner tube (736), an ultrasonic waveguide (738), and a rotation knob (742).

Figure 24A:
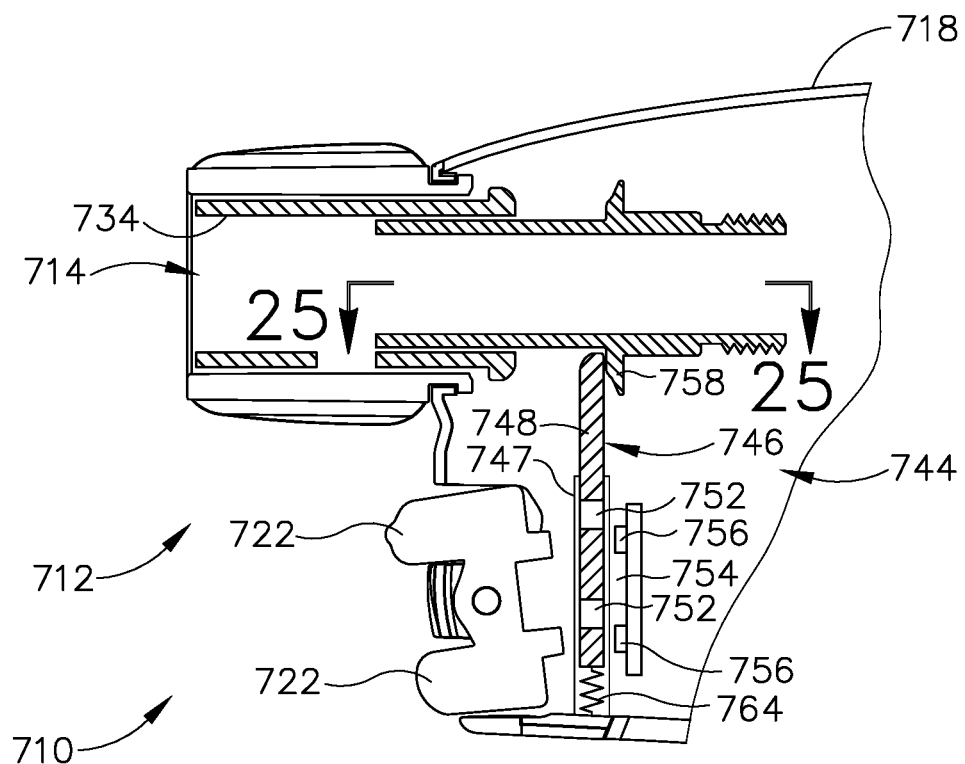
FIG. 24A depicts a schematic side sectional view of the instrument similar to FIG. 23 including an eighth exemplary mechanical lockout assembly in a locked configuration.
Figure 24B:
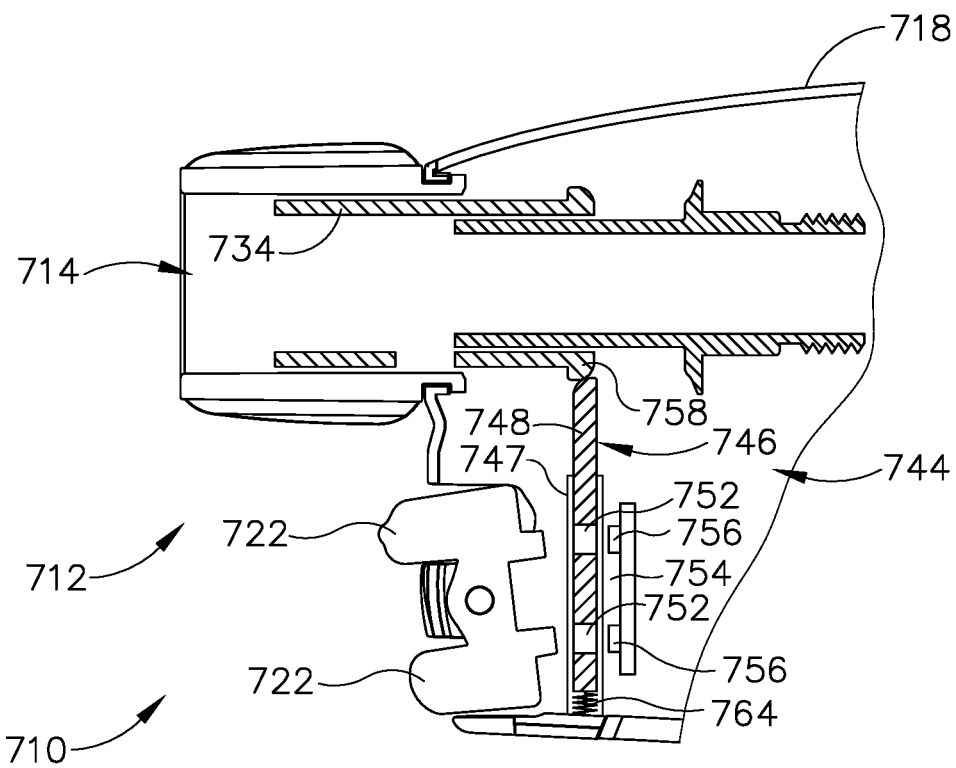
FIG. 24B depicts the schematic side sectional view of the instrument similar to FIG. 24A, but in an unlocked configuration.

FIGS. 24A-24B show instrument (710) as including a mechanical lockout assembly (744). Mechanical lockout assembly (744) includes a barrier (746) that translates between a locked configuration and an unlocked configuration. Barrier (746) may translate within a molded track (747), which may be integrally formed as a unitary piece together with body (718). Barrier (746) includes at least one body portion (748) with at least one aperture (752) being disposed within body portion (748). FIGS. 24A-24B show two apertures (752). Barrier (746) is shown as a lockout slide that is disposed within handle assembly (712). Handle assembly (712) includes energy control buttons (722) separated by a passageway (754) from switches (756).

FIG. 24A shows instrument (710) in the locked configuration, where body portion (748) contacts and translates body portion (750) that is disposed between energy control buttons (722) and switches (756). In other words, when shaft assembly (714), which includes outer tube (734) and clamp arm (730), is not completely coupled with handle assembly (712), barrier (746) prevents the energy control button (722) from being depressed. This prevents switches (756) from activating instrument (710). In the locked configuration, compression spring (764) is in an extended state. In the locked state shown in FIG. 24A, barrier (746) is positioned such that apertures (752) are not interposed between buttons (722) and corresponding switches (756). Barrier (746) thus prevents buttons (722) from activating corresponding switches (756), thereby preventing activation of instrument (710). FIG. 25 depicts a schematic cross-sectional view of FIG. 24A in the locked configuration.

FIG. 24B shows instrument (710) in an unlocked configuration, where apertures (752) are disposed between energy control buttons (722) and switches (756) enabling switches (756) to activate instrument (710). In moving to the unlocked configuration, barrier (746) is pushed downwards into passageway (754) extending between energy control buttons (722) and switches (756). With barrier (746) in a downward position, apertures (752) are positioned between buttons (722) and corresponding switches (756), thereby providing clearance for buttons (722) to activate corresponding switches (756). As shown in FIG. 24B, a tab (758) presses lockout slide down allowing energy control buttons (722) to contact switches (756). Tab (758) may be formed in outer tube (734) or be part of an outer tube overmold. Full coupling of shaft assembly (714) with handle assembly (712) thus causes instrument (710) to move from the locked configuration to the unlocked configuration. In the unlocked configuration, compression spring (764) is in a compressed state. In other words, barrier (746) is spring loaded to return the initial locked configuration, once the shaft assembly (714) is removed.

Figure 26A:
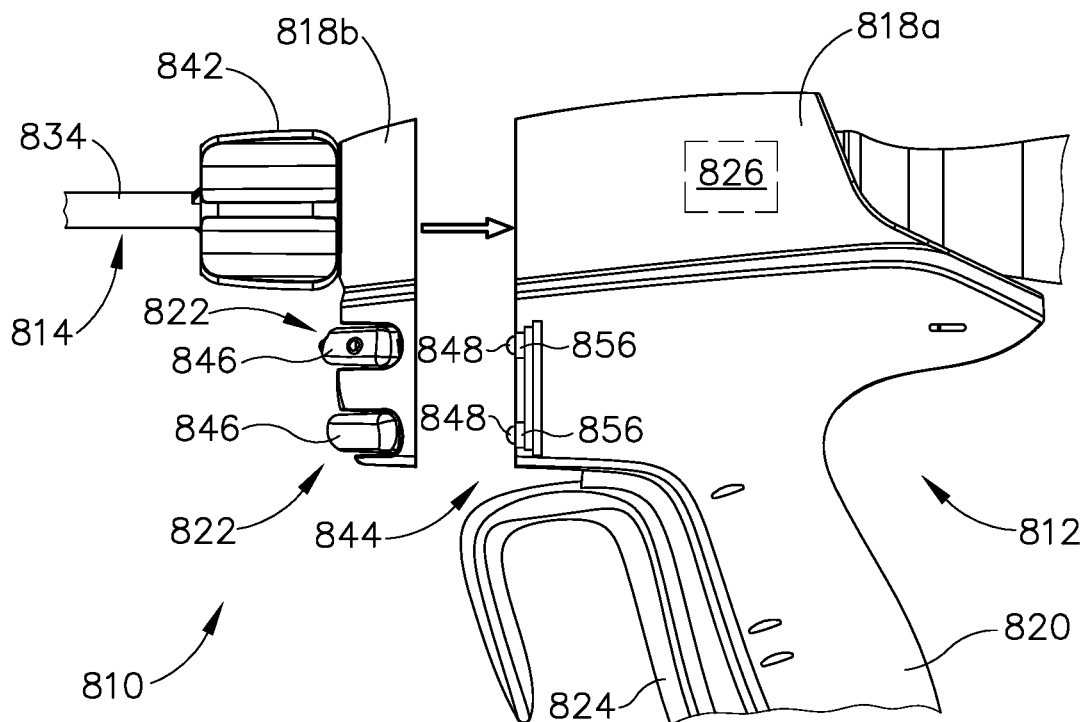
FIG. 26A depicts a schematic side view of a ninth exemplary ultrasonic surgical instrument including a ninth exemplary mechanical lockout assembly in a locked configuration.
Figure 26B:
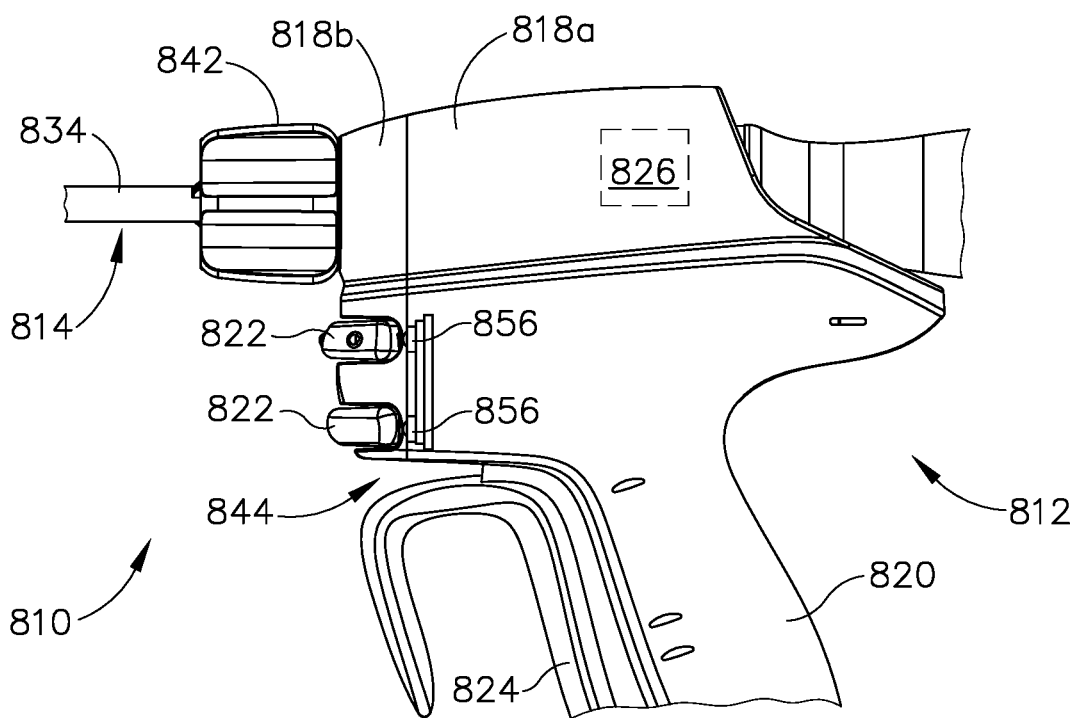
FIG. 26B depicts the schematic side view of the instrument similar to FIG. 26A, but in an unlocked configuration.

I. Ninth Exemplary Ultrasonic Surgical Instrument Having a Ninth Example of a Mechanical Lockout Assembly FIGS. 26A-26B show a ninth exemplary ultrasonic surgical instrument (810) including a ninth mechanical lockout assembly (844). Instrument (810) of the present example comprises a first modular assembly shown as a first portion of handle assembly (812), a second modular assembly shown as a second portion of handle assembly and a shaft assembly (814), a body (818a, 818b), a pistol grip (820), energy control buttons (822), a trigger (824), an ultrasonic transducer (826), an outer tube (834), and a rotation knob (842).

FIG. 26A shows instrument (810) in a locked configuration, where a mechanical lockout assembly (844) prevents activation of instrument (810) if shaft assembly (814) is not completely coupled with handle assembly (812). Handle assembly (812) may include at least a portion of energy control buttons (822). For example, energy control buttons (822) may be split into shaft and handle portions (846, 848), or have energy control buttons (822) entirely with shaft assembly (814). For example, as shown in FIG. 26A, shaft portions (846) of energy control buttons (822) may be coupled with shaft assembly (814) while handle portions (848) of energy control buttons (822) may be coupled with handle assembly (812). Misalignment of shaft and handle portions (846, 848) of energy control buttons (822) prevents switches (856) from activating instrument (810).

FIG. 26B shows instrument (810) in an unlocked configuration, where shaft assembly (814) is completely coupled with handle assembly (812). In the unlocked configuration, mechanical lockout assembly (844) allows energy control button (822) to contact switch (856), allowing an operator to activate instrument (810). Alignment of shaft and handle portions (846, 848) of energy control buttons (822) enable switches (856) to activate instrument (810). Switches (856), which may be dome switches according to an exemplary embodiment, may be in electrical communication with a printed circuit board ("PCB") and may remain within handle assembly (812). Memory, such as EEPROM, may be disposed within handle assembly (812), and cannot activate energy control buttons (822) without shaft assembly (814) completely installed. Switches (856) may be recessed within handle assembly (812) to prevent unintentional actuation.

J. Tenth Exemplary Ultrasonic Surgical Instrument Having a Tenth Example of a Mechanical Lockout Assembly FIGS. 27A-28D show a tenth exemplary ultrasonic surgical instrument (910) including a tenth mechanical lockout assembly (944). Instrument (910) of the present example comprises a first modular assembly shown as a handle assembly (912), a second modular assembly shown as a shaft assembly (914), a body (918), a pistol grip (920), at least one energy control button (922), a trigger (924), an ultrasonic transducer (926), and an outer tube (934).

As shown in FIGS. 27A-27D, handle assembly (912) includes switches (956) that are configured to be actuated by energy control buttons (922). Mechanical lockout assembly (944) includes a closure lever link (946) operatively coupled with trigger (924) in handle assembly (912). Handle assembly (912) includes stop features (948) that may limit motion of closure lever link (946), if desired. Stop features (948) may be integrally formed as a unitary piece with body (918) of handle assembly (912) or may be distinct components coupled with body (918) of handle assembly (912). As shown in FIGS. 27A-27D, closure lever link (946) is coupled at a first end with body (918) at a first rotation point (950). Closure lever link (946) is coupled at a second end with trigger (924) at a second rotation point (952). Additionally, trigger (924) is coupled with body (918) at a third rotation point (954).

Figure 27A:
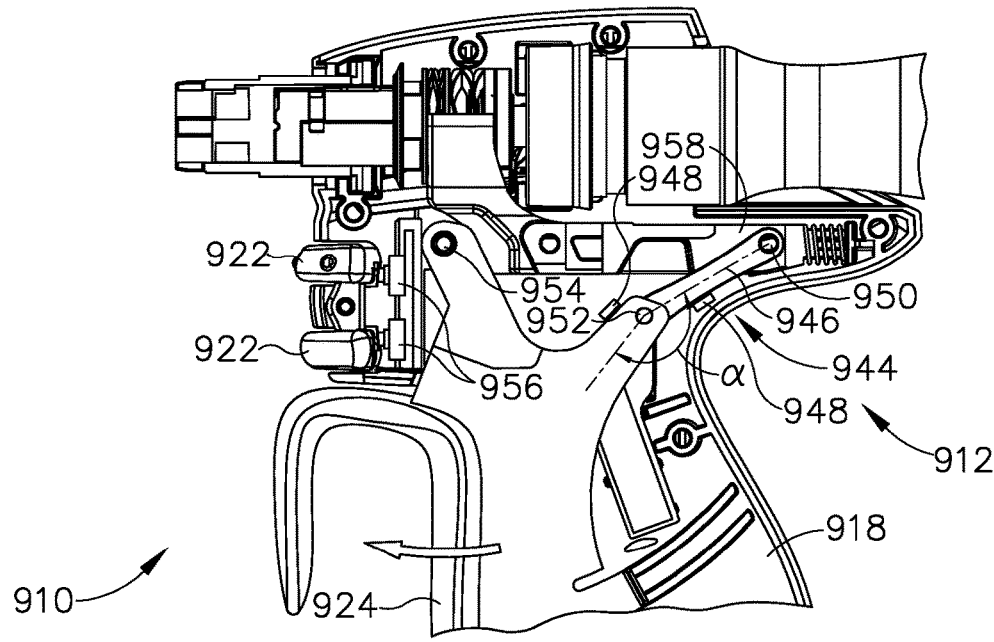
FIG. 27A depicts a schematic side sectional view of a tenth exemplary ultrasonic surgical instrument including a tenth exemplary mechanical lockout assembly in an unlocked configuration.

FIG. 27A shows instrument (910) in an unlocked configuration, with FIG. 28A showing a detailed view of handle assembly (912) where shaft assembly (914) is subsequently inserted therethrough. As shown, in the unlocked configuration, angle alpha (α) between first rotation point (950) and a point of trigger (924) is less than 180 degrees. To switch instrument (910) into a locked configuration, trigger (924) is rotated/translated distally as shown by the arrow. It is also envisioned that instrument (910) may be initially in the locked configuration, as will be described in connection with FIG. 28B.

Figure 27B:
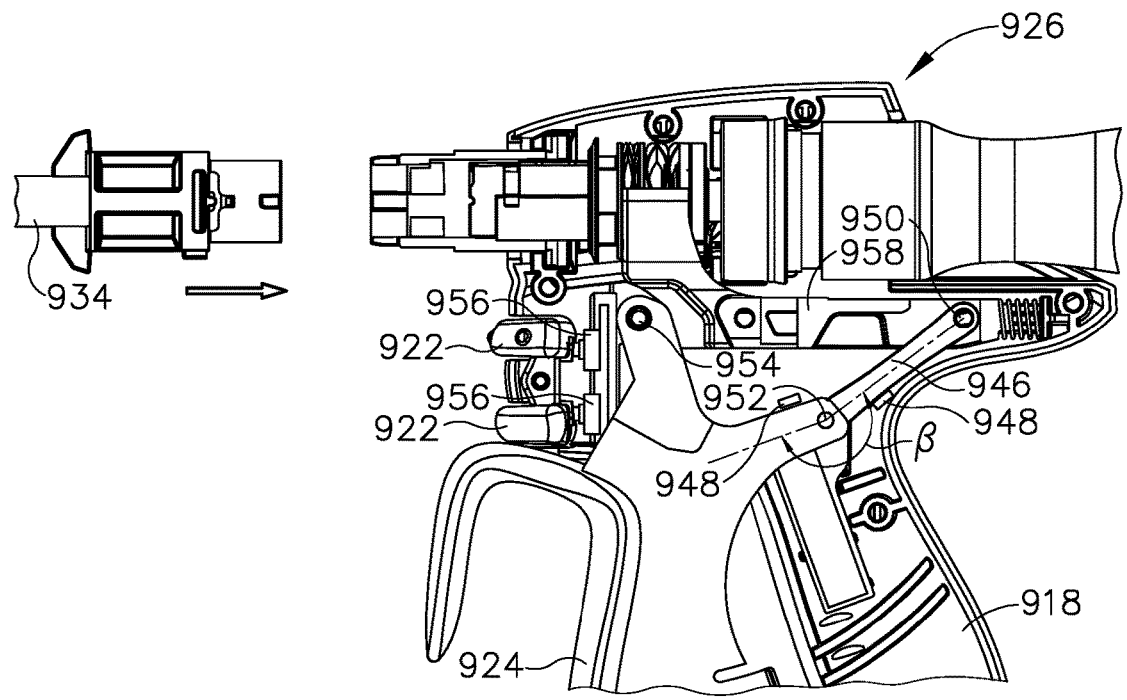
FIG. 27B depicts the schematic side sectional view of the instrument similar to FIG. 27A in a locked configuration.

FIG. 27B shows where the operator pulls closure lever link (946) beyond the unlocked configuration, which functions as the normal operating position, with FIG. 28B showing a detailed view of shaft assembly (914) being actively inserted into handle assembly (912). In the locked configuration when shaft assembly (914) is partially coupled with handle assembly (912), closure lever link (946) is pulled over center in a first direction. Pulling closure lever link (946) over center prevents closure lever link (946) from being rotated closed. As shown in the locked configuration, angle beta (β) between first rotation point (950) and a point of trigger (924) is greater than 180 degrees. When trigger (924) is effectively locked, this prevents the operator from clamping on tissue with an end effector disposed at a distal end of shaft assembly (914) until shaft assembly (914) is fully seated in handle assembly (912).

Figure 27C:
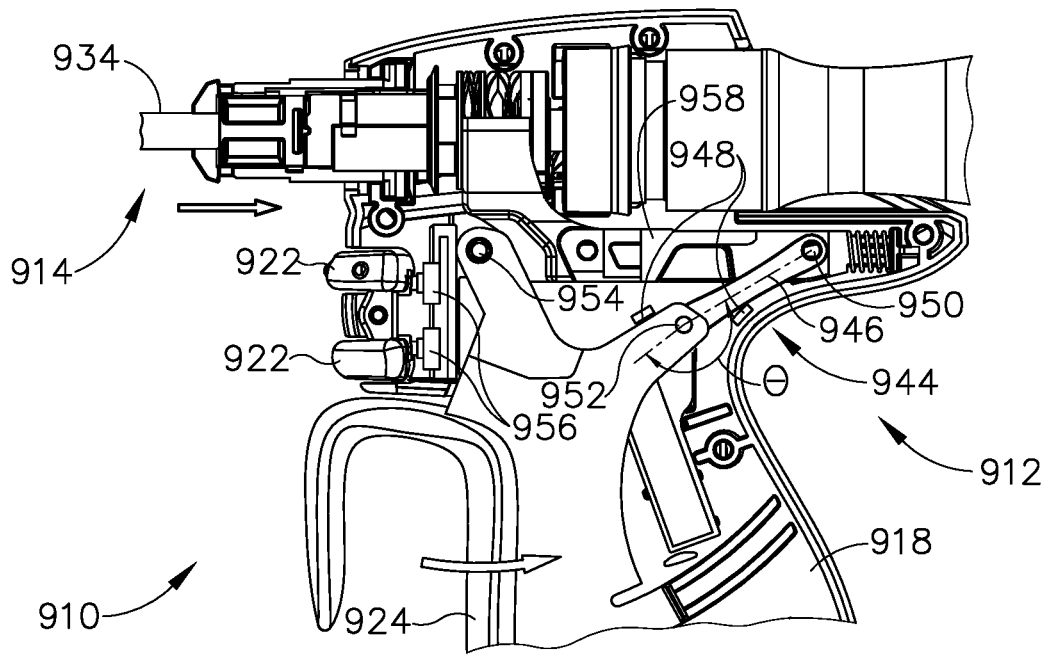
FIG. 27C depicts the schematic side sectional view of the instrument similar to FIG. 27B, but in a second locked configuration.

FIGS. 27C and 28C show a second locked configuration, where shaft assembly (914) is inserted into instrument (910), which pushes yoke (958) proximally, and relieves closure lever link (946) from being over center. Yoke (958) couples trigger assembly of handle with the clamp arm closure driver of shaft assembly (914). As shown in the second locked configuration, angle theta (θ) between first rotation point (950) and a point of trigger (924) is approximately 180 degrees. Mechanical lockout assembly (944) maintains the locked configuration, until shaft assembly (914) is fully seated with handle assembly (912).

Figure 27D:
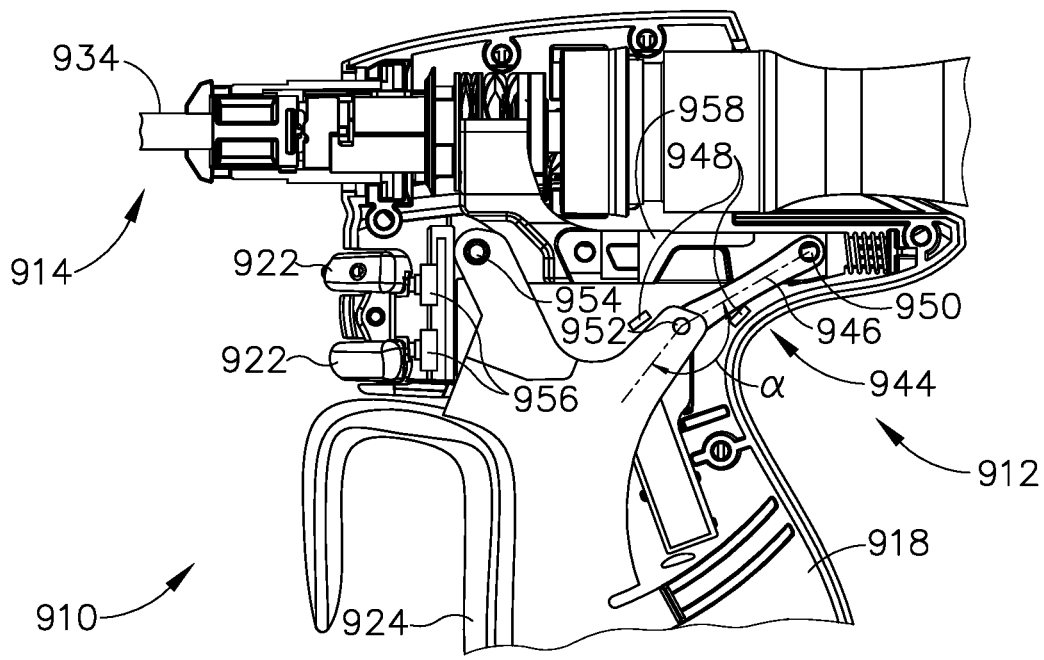
FIG. 27D depicts the schematic side sectional view of the instrument similar to FIG. 27C, but in the unlocked configuration similar to FIG. 27A.
Figure 29:
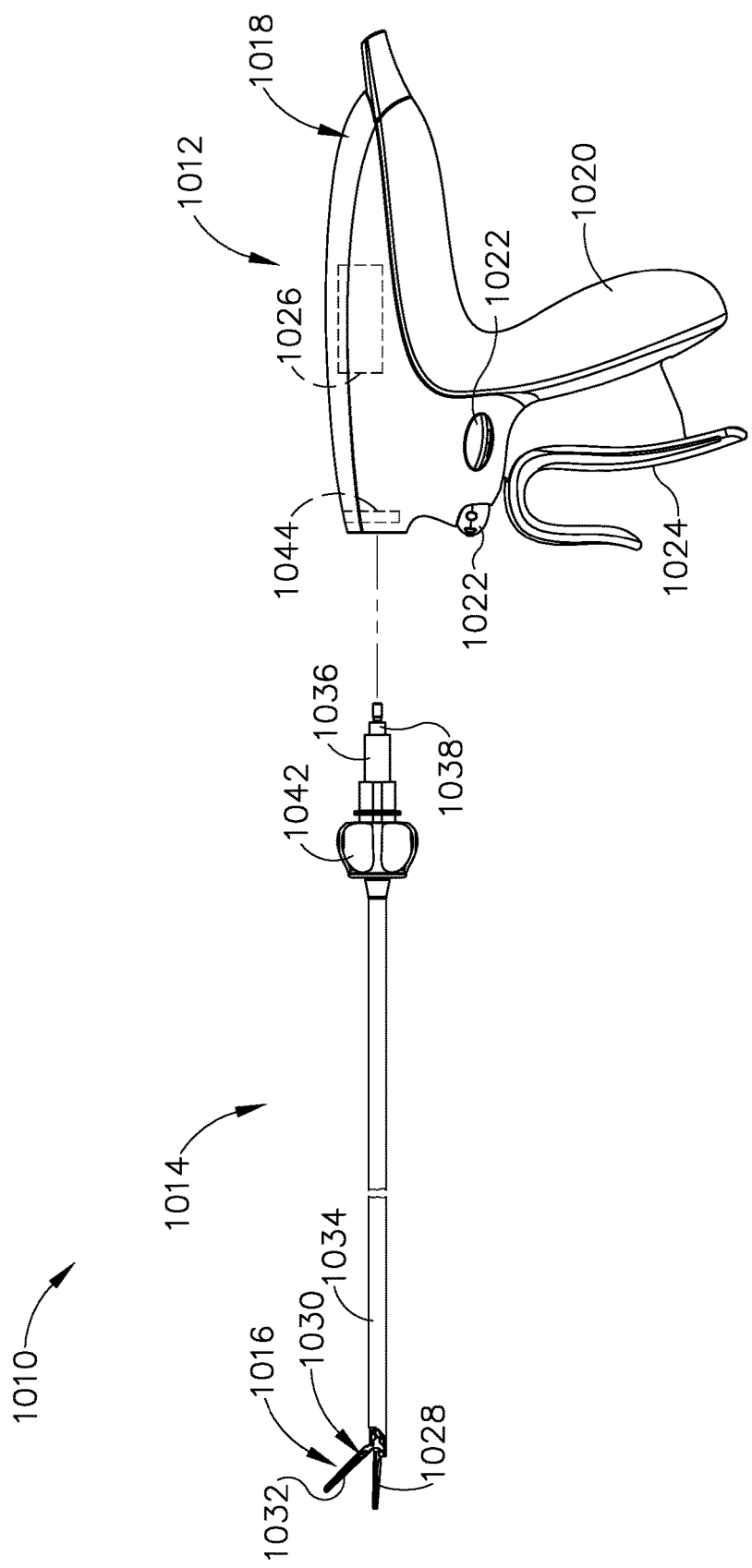
FIG. 29 depicts a schematic partially exploded side view of an eleventh exemplary ultrasonic surgical instrument.

FIGS. 27D and 28D show the unlocked configuration when shaft assembly (914) is completely coupled with handle assembly (912). FIG. 27D shows that activation of trigger (924) causes closure lever link (946) to rotate in second direction that is opposite first direction. Once shaft assembly (914) is fully seated in handle assembly (912), trigger (924) is transitioned to the unlocked configuration. This allows trigger (924) to be actuated to thereby actuate a clamp arm of an end effector. Mechanical lockout assembly (944) effectively locks out use of a clamp arm assembly. In the unlocked configuration, angle alpha ($\alpha$) between first rotation point (950) and a point of trigger (924) is less than 180 degrees.

K. Eleventh Exemplary Ultrasonic Surgical Instrument Having an Eleventh Example of a Mechanical Lockout Assembly FIGS. 29-31C show an eleventh exemplary ultrasonic surgical instrument (1010) including an eleventh mechanical lockout assembly (1044). Instrument (1010) of the present example comprises a first modular assembly shown as a handle assembly (1012), a second modular assembly shown as a shaft assembly (1014), an end effector (1016), a body (1018), a pistol grip (1020), energy control buttons (1022), a trigger (1024), an ultrasonic transducer (1026), an ultrasonic blade (1028), a clamp arm (1030), a clamp pad (1032), an outer tube (1034), an inner tube (1036), an ultrasonic waveguide (1038), and a rotation knob (1042).

Figure 30A:
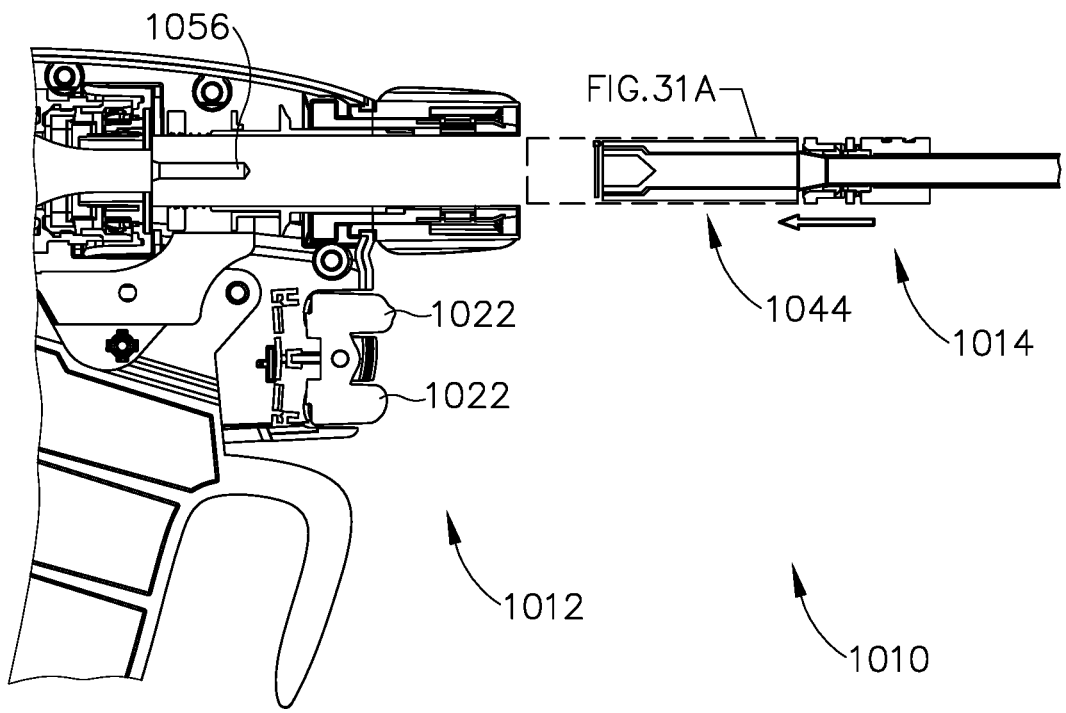
FIG. 30A depicts a schematic sectional view of the instrument similar to FIG. 29 including an eleventh exemplary mechanical lockout assembly in a locked configuration.
Figure 30B:
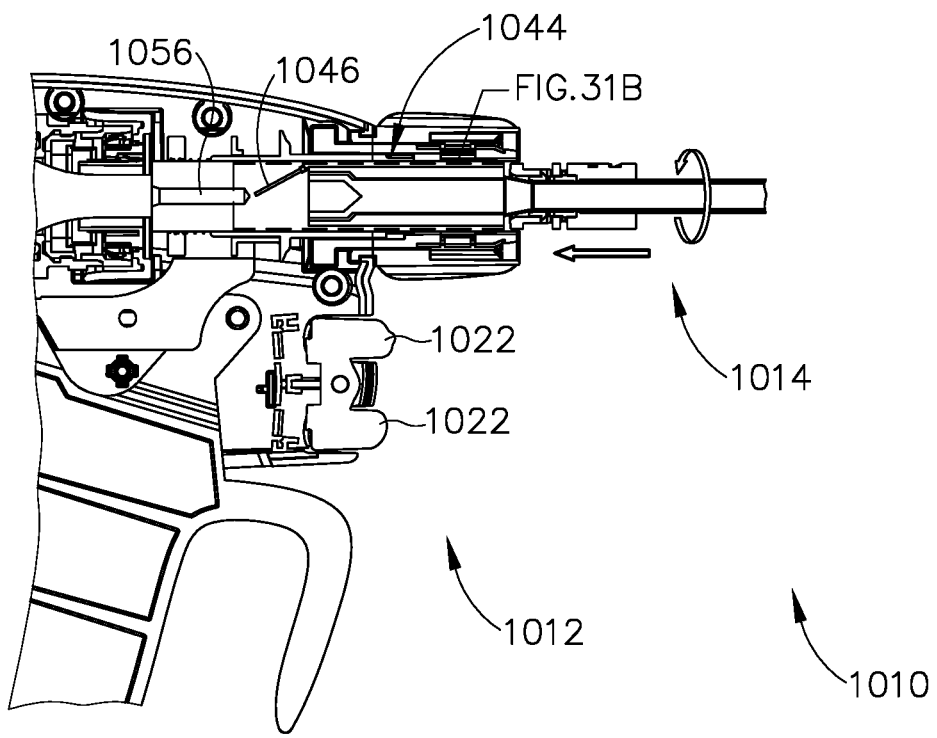
FIG. 30B depicts the schematic sectional view of the instrument similar to FIG. 30A, but moving from a locked configuration to an unlocked configuration.
Figure 30C:
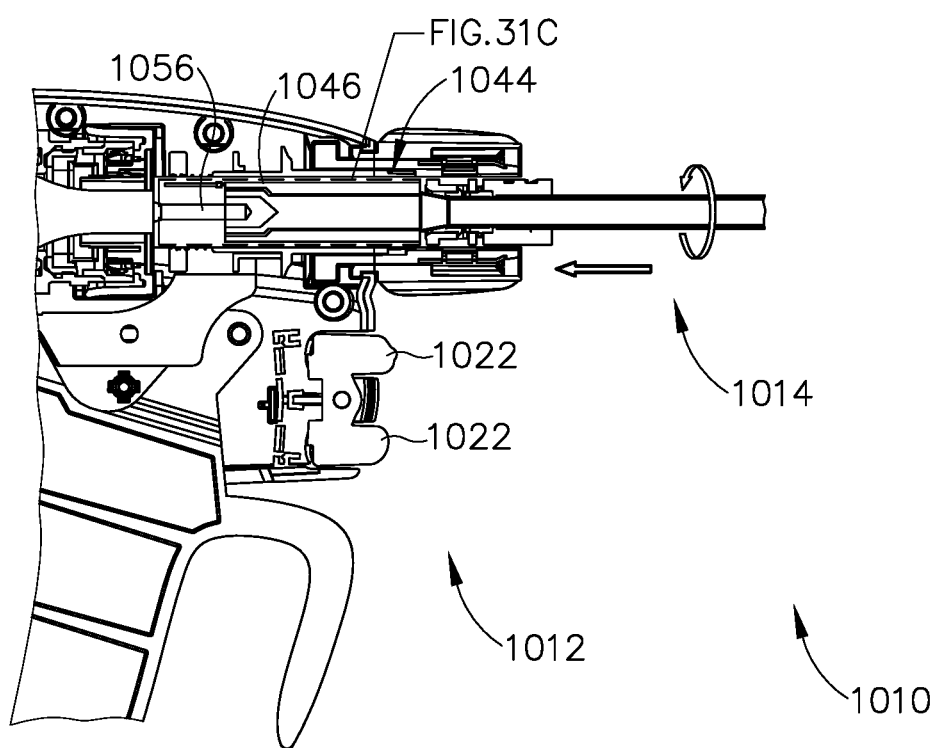
FIG. 30C depicts the schematic sectional view of the instrument similar to FIG. 30B, but in the unlocked configuration.
Figure 31A:
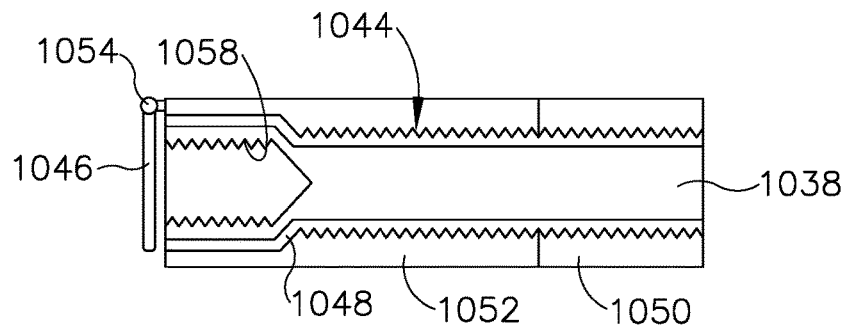
FIG. 31A depicts a schematic enlarged side sectional view of the mechanical lockout assembly similar to FIG. 30A in the locked configuration.

FIGS. 30A-30C show instrument (1010) as including a mechanical lockout assembly (1044). Mechanical lockout assembly (1044) includes a one-way door (1046) that is configured to be opened by coupling handle assembly (1012) with shaft assembly (1014). As shown in FIGS. 30A-30C, mechanical lockout assembly (1044) is coupled with shaft assembly (1014), such that shaft assembly (1014) and mechanical lockout assembly (1044) are coupled together, however, this is not required. FIGS. 30A and 31A show shaft assembly (1014) approaching handle assembly (1012), with one-way door (1046) blocking access to threaded bore (1058) at the proximal end of acoustic waveguide (1038) of shaft assembly (1014).

Figure 31B:
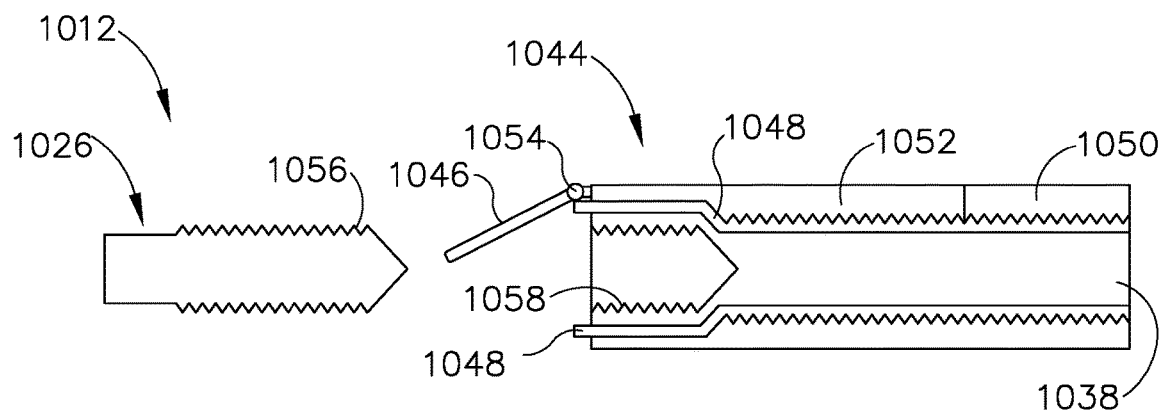
FIG. 31B depicts the schematic enlarged side sectional view of the mechanical lockout assembly similar to FIG. 30B transitioning from the locked configuration to the unlocked configuration.

FIGS. 30B and 31B show shaft assembly (1014) partially coupled with handle assembly (1012), with one-way door (1046) still preventing threaded stud (1056) of ultrasonic transducer (1026) from reaching threaded bore (1058) at the proximal end of acoustic waveguide (1038). In moving between a locked and an unlocked configuration, translatable jacket (1048) translates relative to one-way door (1046) pushing one-way door (1046) to the unlocked configuration (shown in FIGS. 30C and 31C) allowing complete coupling of threaded stud (1056) with threaded bore (1058), thereby completing an acoustic coupling between ultrasonic transducer (1026) and ultrasonic waveguide (1038).

As shown, linear translation of outer tube (1034) of shaft assembly (1014) relative to translatable jacket (1048) opens one-way door (1046). As shown, outer tube (1034) includes a rotary component (1050) and a yoke (1052), however, rotary component (1050) and yoke (1052) may be integrally formed as a unitary piece or fixably coupled together using a variety of known attachment methods. As shown, rotation of rotary component (1050) of outer tube (1034) causes yoke (1052) of outer tube (1034) and translatable jacket (1048) to translate towards handle assembly (1012). Yoke (1052) may be threadably coupled with rotary component (1050), with yoke (1052) being keyed to shaft assembly (1014), such that yoke (1052) translates relative to shaft assembly (1014) without rotating relative to shaft assembly (1014). Rotation of rotary component (1050) drives yoke (1052) proximally, allowing translatable jacket (1048) to translate proximally, which in turn allows one-way door (1046) to rotate open at a hinge point (1054).

Figure 31C:
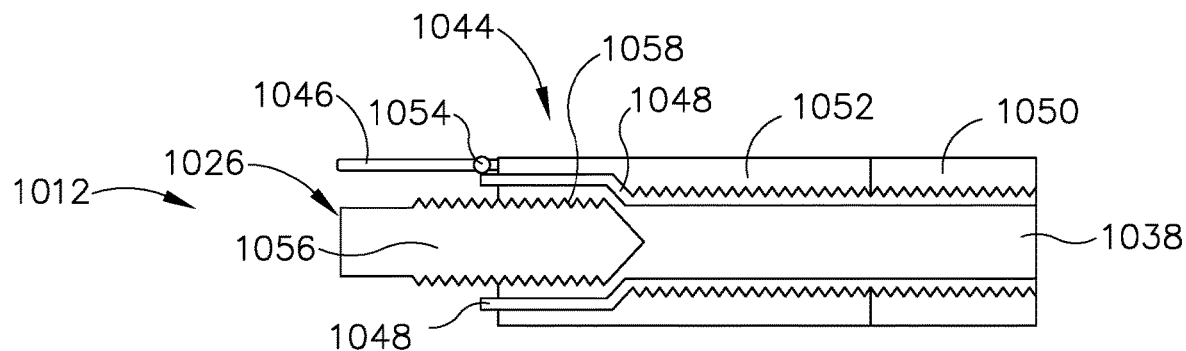
FIG. 31C depicts the schematic enlarged side sectional view of the mechanical lockout assembly similar to FIG. 30C in the unlocked configuration.
Figure 32:
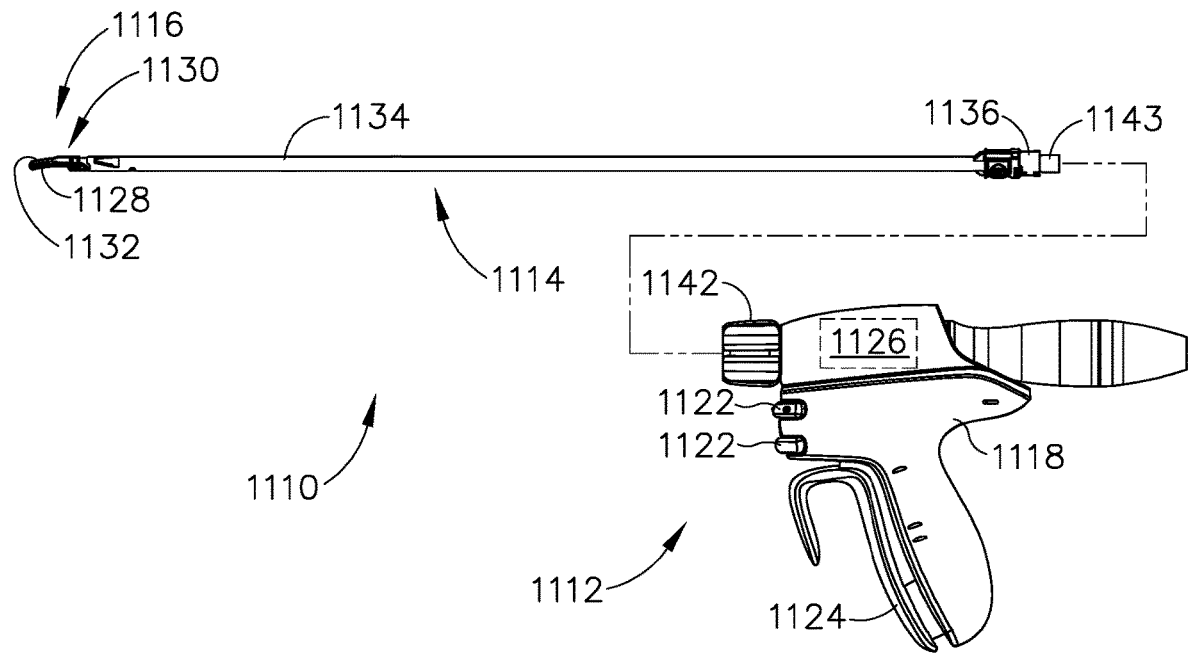
FIG. 32 depicts a schematic side view of a twelfth exemplary ultrasonic surgical instrument.

FIGS. 30C and 31C show the unlocked configuration where shaft assembly (1014) is completely coupled with handle assembly (1012), and with transducer (1026) fully coupled with waveguide (1038), thereby allowing ultrasonic activation of ultrasonic blade (1028). FIGS. 30C and 31C show that once one-way door (1046) is open, externally threaded stud (1056) of ultrasonic transducer (1026) may be threadably coupled with an internally threaded proximal recess (1058) of ultrasonic waveguide (1038). In other words, once one-way door (1046) is open and outer tube (1034) is fully translated, ultrasonic transducer (1026) is able to acoustically couple with ultrasonic waveguide (1038). One-way door (1046) ensures that the acoustic drivetrain may only be assembled when shaft assembly (1014) is completely coupled with handle assembly (1012).

For instrument (1010), which includes clamp arm (1030) that is assembled by the operator to handle assembly (1012), it is beneficial that clamp arm (1030) be precisely aligned with ultrasonic blade (1028). Mechanical lockout assembly (1044) incorporates a means to lock out the acoustic drivetrain, so that ultrasonic blade (1028) cannot be activated by energy control buttons (1022) until shaft assembly (1014) is completely coupled with handle assembly (1012). Additionally, if there is not full rotary engagement, translatable jacket (1048) falls short and cannot open one-way door (1046), and as a result, handle assembly (1012) contacts one-way door (1046) and does not thread ultrasonic waveguide (1038). This prevents use of trigger (1024) that drives the clamp arm (1030) and champ pad (1032) toward the ultrasonic blade (1028), which provides tactile feedback to the operator of the inoperability of instrument (1010) due to being in the locked configuration.

L. Twelfth Exemplary Ultrasonic Surgical Instrument Having a Twelfth Example of a Mechanical Lockout Assembly FIGS. 32-34D show a twelfth exemplary ultrasonic surgical instrument (1110) including a twelfth mechanical lockout assembly (1144). Instrument (1110) of the present example comprises a first modular assembly shown as a handle assembly (1112), a second modular assembly shown as a shaft assembly (1114), an end effector (1116), a body (1118), a pistol grip (1120), energy control buttons (1122), a trigger (1124), an ultrasonic transducer (1126), an ultrasonic blade (1128), a clamp arm (1130), a clamp pad (1132), an outer tube (1134), an inner tube (1136), a rotation knob (1142), and a shaft coupler (1143).

Figure 33:
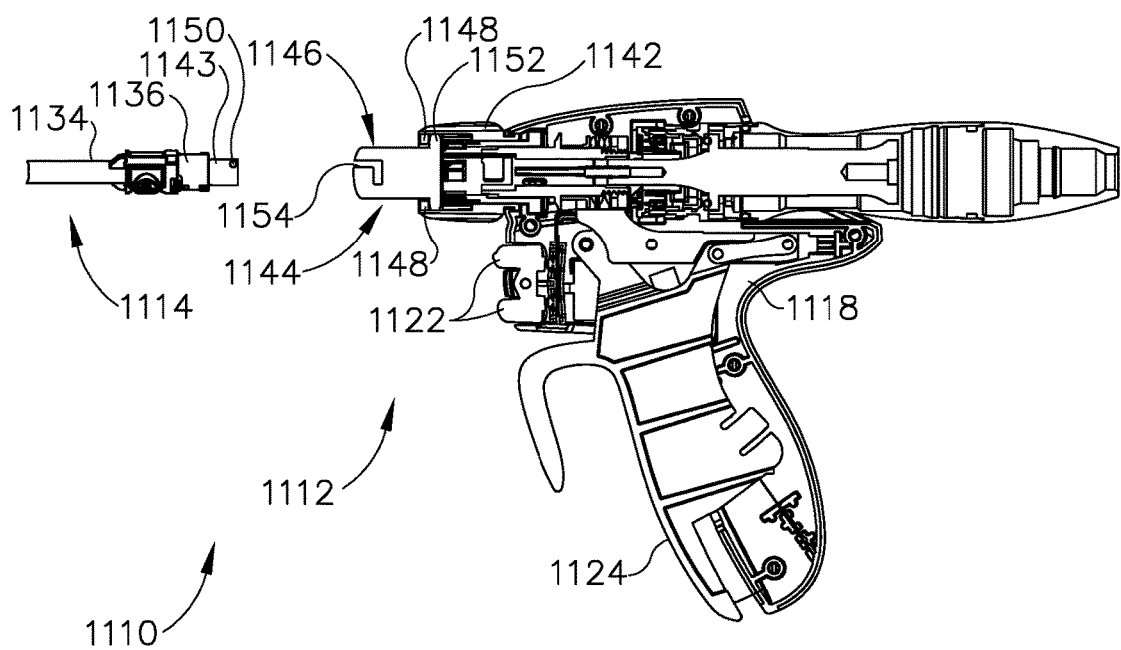
FIG. 33 depicts a schematic side sectional view of the instrument of FIG. 32 including a twelfth exemplary mechanical lockout assembly in a locked configuration.

FIG. 33 shows that instrument (1110) includes a mechanical lockout assembly (1144). Mechanical lockout assembly (1144) includes a coupling device (1146) operatively coupled to handle assembly (1112) using a retention member (1148) that restricts distal translation of a head portion (1152) of coupling device (1146). More specifically, since coupling device (1146) translates longitudinally to communicate a clamp arm closure motion from trigger (1124) to clamp arm actuator of shaft assembly (1114), coupling device (1146) subsequently translates proximally from the position shown in FIG. 33. Subsequently, coupling device (1146) translates distally back to the position shown in FIG. 33. In this manner, retention member (1148) restricts distal translation of coupling device (1146). Clamp arm actuating member translates relative to the remainder of shaft assembly (1114) to drive pivotal movement of clamp arm (1130) toward and away from ultrasonic blade (1128). As shaft assembly (1114) couples with handle assembly (1112), projection (1150) that is shown integral with clamp arm actuating member of shaft assembly (1114), enters track (1154) to suitably couple shaft assembly (1114) with handle assembly (1112).

FIGS. 34A-34D show four exemplary coupling devices (1156, 1158, 1160, 1162), configured to be used with mechanical lockout assembly (1144) of instrument (1110). Coupling devices (1146, 1156, 1158, 1160, 1162) translate longitudinally in response to pivotal movement of trigger (1124). Coupling devices (1146, 1156, 1158, 1160, 1162) also couple trigger (1124) with the clamp arm closure actuator of shaft assembly (1114). Clamp arm closure actuator includes projection (1150). Thus, if projection (1150) of shaft assembly (1114) is fully seated in coupling device (1146, 1156, 1158, 1160, 1162), the clamp arm closure actuator will translate and thereby drive clamp arm (1130) toward and away from ultrasonic blade (1128), based on translation of coupling device (1146, 1156, 1158, 1160, 1162) as driven by trigger (1124). If projection (1150) of shaft assembly (1114) is not fully seated in coupling device (1146, 1156, 1158, 1160, 1162), coupling device (1146, 1156, 1158, 1160, 1162) still translates in response to pivotal movement of trigger (1124). However, the translational movement of the coupling device (1146, 1156, 1158, 1160, 1162) is not be communicated to the clamp arm closure actuator. Thus, clamp arm (1130) does not move at all in response to movement of trigger (1124). Coupling devices (1146, 1156, 1158, 1160, 1162) move proximally to actuate clamp arm (1130).

As will be described below, each coupling device (1156, 1158, 1160, 1162) includes a guide track (1164, 1166, 1168, 1170) configured to engage with projection (1150) shown in FIG. 33 of shaft assembly (1114). Guide tracks (1154, 1164, 1166, 1168, 1170) of respective coupling devices (1146, 1156, 1158, 1160, 1162) are configured to translate and rotate shaft assembly (1114) using the interaction between projection (1150) and guide track (1154, 1164, 1166, 1168, 1170) from the locked configuration when shaft assembly (1114) is partially coupled with handle assembly (1112) to the unlocked configuration when shaft assembly (1114) is completely coupled with handle assembly (1112).

Figure 34A:
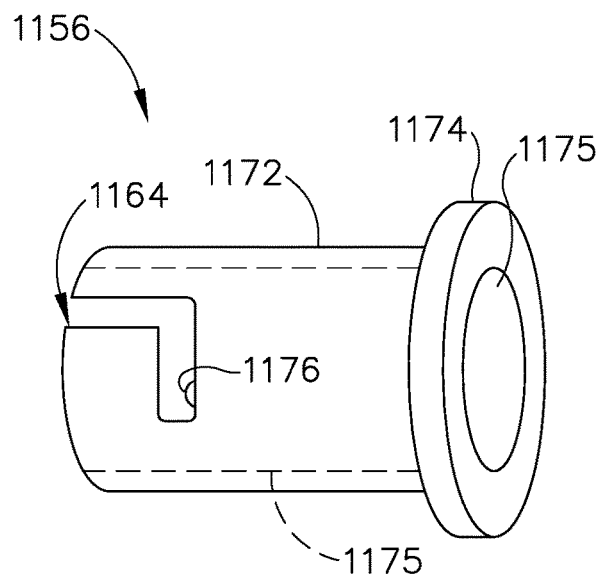
FIG. 34A depicts a schematic perspective view of a first alternative embodiment of a coupling device configured to be used with the instrument of FIG. 32.

FIG. 34A shows a coupling device (1156) with a guide track (1164) disposed within a body portion (1172) and a head portion (1174) that is configured to be retained by retention member (1148), and an aperture (1175) extending therethrough. Coupling device (1156) is similar to coupling device (1146) shown in FIG. 33, however, coupling device (1156) additionally includes a detent (1176) to guide track (1164) to ensure that trigger (1124) and clamp arm (1130) are non-responsive until projection (1150) is fully seated and fully rotated. If projection (1150) is captured by detent (1176), then the translation of coupling device (1156) will be communicated to the clamp arm actuator of shaft assembly (1114), such that the clamp arm (1130) will close in response to pivoting of trigger (1124). Detent (1176) provides tactile feedback to the operator indicating to the operator that shaft assembly (1114) is fully coupled; and to prevent inadvertent decoupling of the shaft assembly (1114) after shaft assembly (1114) is fully coupled.

Figure 34B:
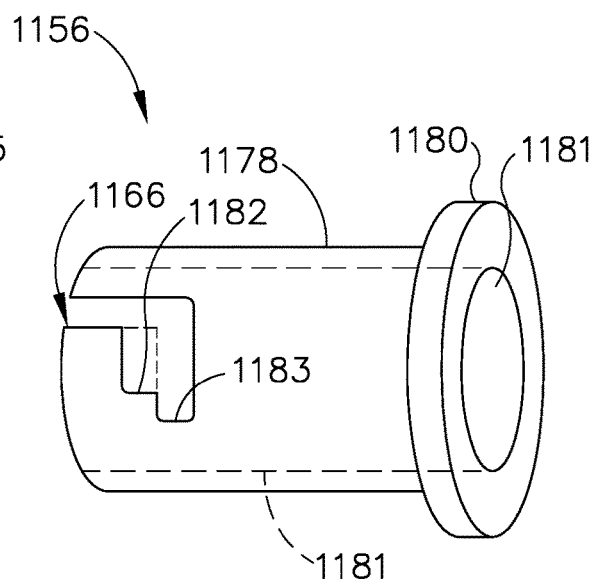
FIG. 34B depicts a schematic perspective view of a second alternative embodiment of a coupling device configured to be used with the instrument of FIG. 32.
Figure 34C:
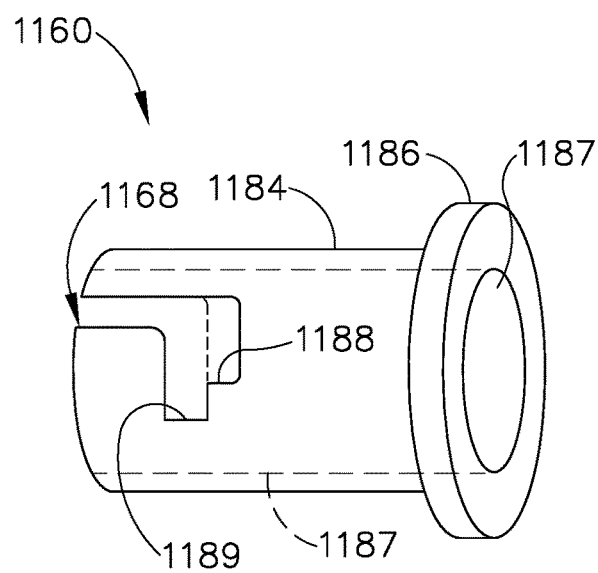
FIG. 34C depicts a schematic perspective view of a third alternative embodiment of a coupling device configured to be used with the instrument of FIG. 32.
Figure 34D:
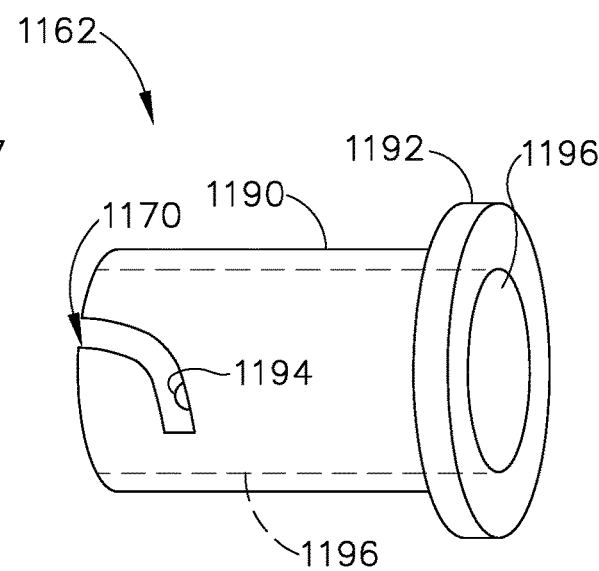
FIG. 34D depicts a schematic perspective view of a fourth alternative embodiment of a coupling device configured to be used with the instrument of FIG. 32.
Figure 35:
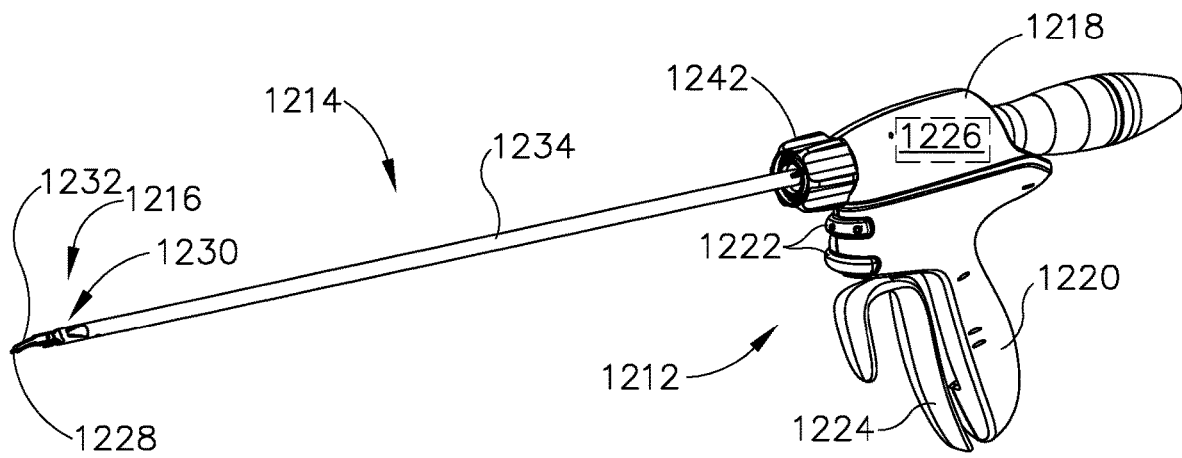
FIG. 35 depicts a schematic perspective view of a thirteenth exemplary ultrasonic surgical instrument.

FIGS. 34B-34D show three exemplary embodiments of track patterns (1166, 1168, 1170) that result in various changes to the opening/closing of clamp arm (1130) during operation when shaft assembly (1114) is not completely coupled with handle assembly (1112). FIG. 34B shows a coupling device (1158) as including a guide track (1166) disposed within a body portion (1178) and a head portion (1180) that is configured to be retained by retention member (1148), and an aperture (1181) extending therethrough. FIG. 34B shows coupling device (1158) as including an extra relief portion (1182) prior to seating position, which allows clamp arm (1130) to open but not to close, thereby alerting the operator of a potential misalignment. As shown, extra relief portion (1180) is longer than the length of travel.

With continued reference to FIG. 34B, if shaft assembly (1114) is not fully coupled, projection (1150) of shaft assembly (1114) will be in relief portion (1182). If projection (1150) of shaft assembly (1114) is in relief portion (1182), then translation of coupling device (1158) will not be communicated to the clamp arm actuator of shaft assembly (1114), such that clamp arm (1130) will not close in response to pivoting of trigger (1124). If shaft assembly (1114) is fully coupled, projection (1150) will be seated in seat (1183). If projection (1150) captured by seat (1183), then the translation of coupling device (1158) will be communicated to the clamp arm actuator of shaft assembly (1114), such that clamp arm (1130) will open, but not close, in response to pivoting of trigger (1124). Proximal movement of the clamp arm actuator of shaft assembly (1114) provides pivotal movement of clamp arm (1130) toward ultrasonic blade (1128).

FIG. 34C shows a coupling device (1160) with a guide track (1168) disposed within a body portion (1184) and head portion (1186) that is configured to be retained by retention member (1148), and an aperture (1187) extending therethrough. FIG. 34B shows coupling device (1158) as including an extra relief portion (1188) positioned beyond the normal seating position allowing clamp arm (1130) to close if not fully rotated, but not allowing clamp arm (1130) to return back, thereby alerting the operator of a potential misalignment. As shown, extra relief portion (1180) is longer than the length of travel. Distal movement of the clamp arm actuator of shaft assembly (1114) provides pivotal movement of clamp arm (1130) toward ultrasonic blade (1128).

With continued reference to FIG. 34C, if shaft assembly (1114) is not fully coupled, projection (1150) of shaft assembly (1114) will be in relief portion (1188). If projection (1150) of shaft assembly (1114) is in relief portion (1188), the translation of coupling device (1160) will not be communicated to the clamp arm actuator of shaft assembly (1114), such that clamp arm (1130) will not open in response to pivoting of trigger (1124). If shaft assembly (1114) is fully coupled, projection (1150) will be seated in seat (1189). If projection (1150) is captured by seat (1189), then the translation of coupling device (1160) will be communicated to the clamp arm actuator of shaft assembly (1114), such that clamp arm (1130) will close, but not open, in response to pivoting of trigger (1124). Proximal movement of the clamp arm actuator of shaft assembly (1114) provides pivotal movement of clamp arm (1130) toward ultrasonic blade (1128).

FIG. 34D shows a coupling device (1162) as including a guide track (1170) disposed within a body portion (1190) and head portion (1192) that is configured to be retained by retention member (1148), and an aperture (1196) extending therethrough. FIG. 34D shows guide track (1170) as being angled, so as to rotate while advancing. To be fully seated, projection (1150) of shaft coupler (1143) is fully rotated on coupling device (1162). Coupling device (1162) may additionally include a stop member (1194) in guide track (1170) to ensure that trigger (1124) and clamp arm (1130) are non-responsive until projection (1150) is fully seated and fully rotated, such that instrument (1110) is switched from the locked configuration to the unlocked configuration. Similar to detent (1176) shown in FIG. 34A, detent (1194) provides tactile feedback to the operator and prevents inadvertent decoupling. Unlike the FIG. 34A the curved configuration of guide track (1170) causes the coupling device to release projection (1150) if the operator actuates trigger (1124), thereby translating coupling device (1162) if projection (1150) is not fully seated behind detent (1194). Coupling device (1162) moves proximally to actuate clamp arm (1130).

Instrument (1110) prevents outer shaft (1134) from moving forwards/backwards, thereby preventing closing of clamp arm (1130) when shaft assembly (1114) is not fully rotated into position. Mechanical lockout assembly (1144) and its various coupling devices (1146, 1156, 1158, 1160, 1162) prevent responsiveness of clamp arm (1130) to movement of trigger until shaft assembly (1114) is fully seated. Mechanical lockout assembly (1144) using a shaft coupler (1143) with projection (1150) couples with guide tracks (1154, 1164, 1166, 1168, 1170) of respective coupling devices (1146, 1156, 1158, 1160, 1162) providing immediate and clear feedback to the operator of a misalignment between shaft assembly (1114) and handle assembly (1112).

M. Thirteenth Exemplary Ultrasonic Surgical Instrument Having a Thirteenth Example of a Mechanical Lockout Assembly FIGS. 35-41 show a thirteenth exemplary ultrasonic surgical instrument (1210) including a thirteenth mechanical lockout assembly (1244). Instrument (1210) of the present example comprises a first modular assembly shown as a handle assembly (1212), a second modular assembly shown as a shaft assembly (1214), an end effector (1216), a body (1218), a pistol grip (1220), energy control buttons (1222), a trigger (1224), an ultrasonic transducer (1226), an ultrasonic blade (1228), a clamp arm (1230), a clamp pad (1232), an outer tube (1234), an inner tube (1236), and a rotation knob (1242).

Figure 36:
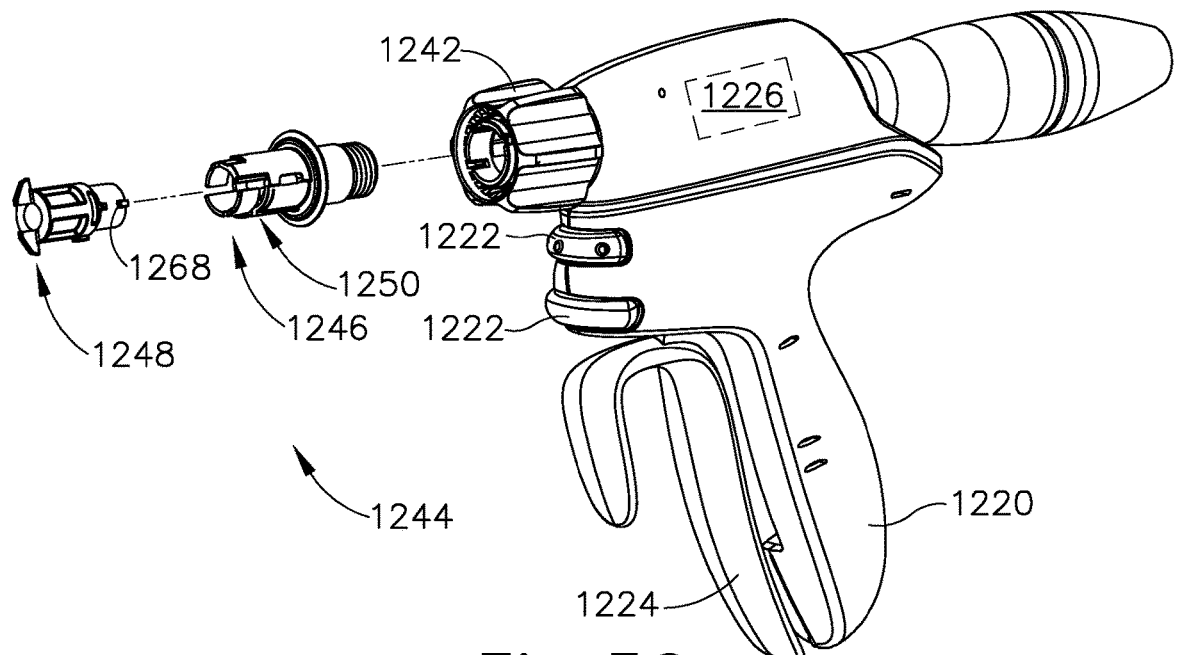
FIG. 36 depicts a schematic partially exploded perspective of the instrument of FIG. 35 including a thirteenth exemplary mechanical lockout assembly.

FIG. 36 shows instrument (1210) as including a mechanical lockout assembly (1244). As shown, mechanical lockout assembly (1244) includes an outer tube collar (1246) and a bayonet collar (1248), and a rotation collar (1249) (see FIG. 41). Outer tube collar (1246) is integrated into handle assembly (1212). Outer tube collar (1246) may rotate within handle assembly (1212), and may also translate within handle assembly (1212). Outer tube collar (1246) is part of a clamp arm drive assembly that couples trigger (1224) of handle assembly (1212) with outer tube (1234) of shaft assembly (1214). When trigger (1224) is actuated, outer tube collar (1246) translates longitudinally. When outer tube collar (1246) translates, the translation of outer tube collar (1246) is communicated to outer tube (1234) of shaft assembly (1214). When outer tube (1234) of shaft assembly (1214) translates, clamp arm (1230) pivots toward and away from ultrasonic blade (1228). Bayonet collar (1248) may be removably coupled with shaft assembly (1214), and is fixedly secured to the proximal end of outer tube (1234) of shaft assembly (1214). Rotation collar (1249) (see FIG. 41) is integrated into handle assembly (1212) as part of rotation knob (1242) that rotates entire shaft assembly (1214) relative to handle assembly (1212). Rotation collar (1249) rotates relative to handle assembly (1212), but does not translate relative to handle assembly (1212).

Figure 37:
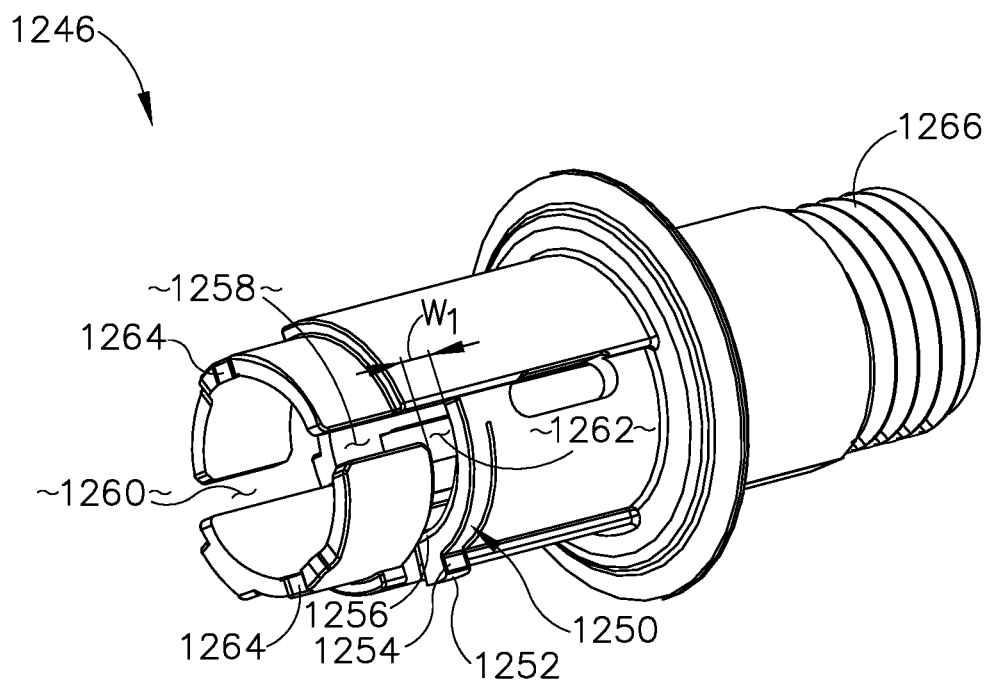
FIG. 37 depicts a schematic enlarged perspective view of an outer tube collar of the mechanical lockout assembly of FIG. 36.

FIG. 37 shows outer tube collar (1246) as including a spring leg (1250) that includes a distal end (1252). Distal end (1252) of spring leg (1250) includes a resilient interference tab (1254) with a contact surface (1255). Spring leg (1250) also includes a cam surface (1256) that acts as a ramp, which will be discussed in greater detail below with reference to FIGS. 39A-40C. Outer tube collar (1246) also includes first and second passageways (1258, 1260), which extend in a generally longitudinal direction relative to outer tube collar (1246), and a third passageway (1262) having a width of W1 that extends generally transverse to the longitudinal direction of outer tube collar (1246). A fourth passageway, similar to third passageway (1262), is hidden from view. Outer tube collar (1246) also includes cutouts (1264) as will be discussed with reference to FIG. 39B. Outer tube collar (1246) may be threadably coupled to a portion of clamp arm drivetrain using threaded portion (1266). Thus, outer tube collar (1246) translates with clamp arm drivetrain.

Figure 38:
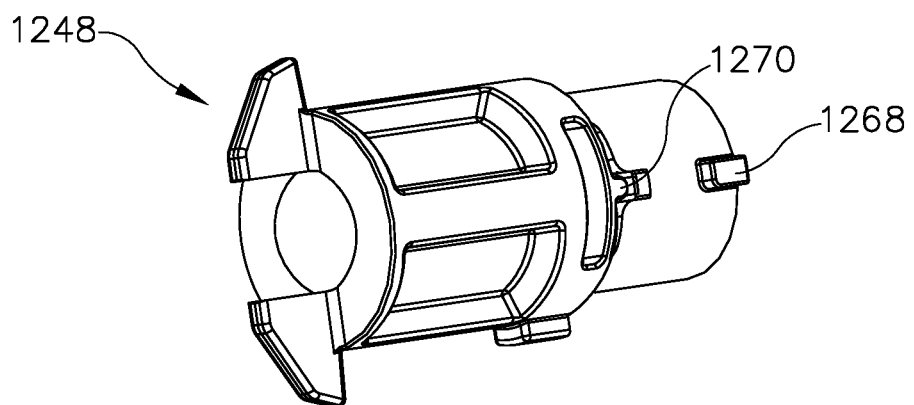
FIG. 38 depicts a schematic enlarged perspective view of a bayonet collar of the mechanical lockout assembly of FIG. 36.
Figure 39C:
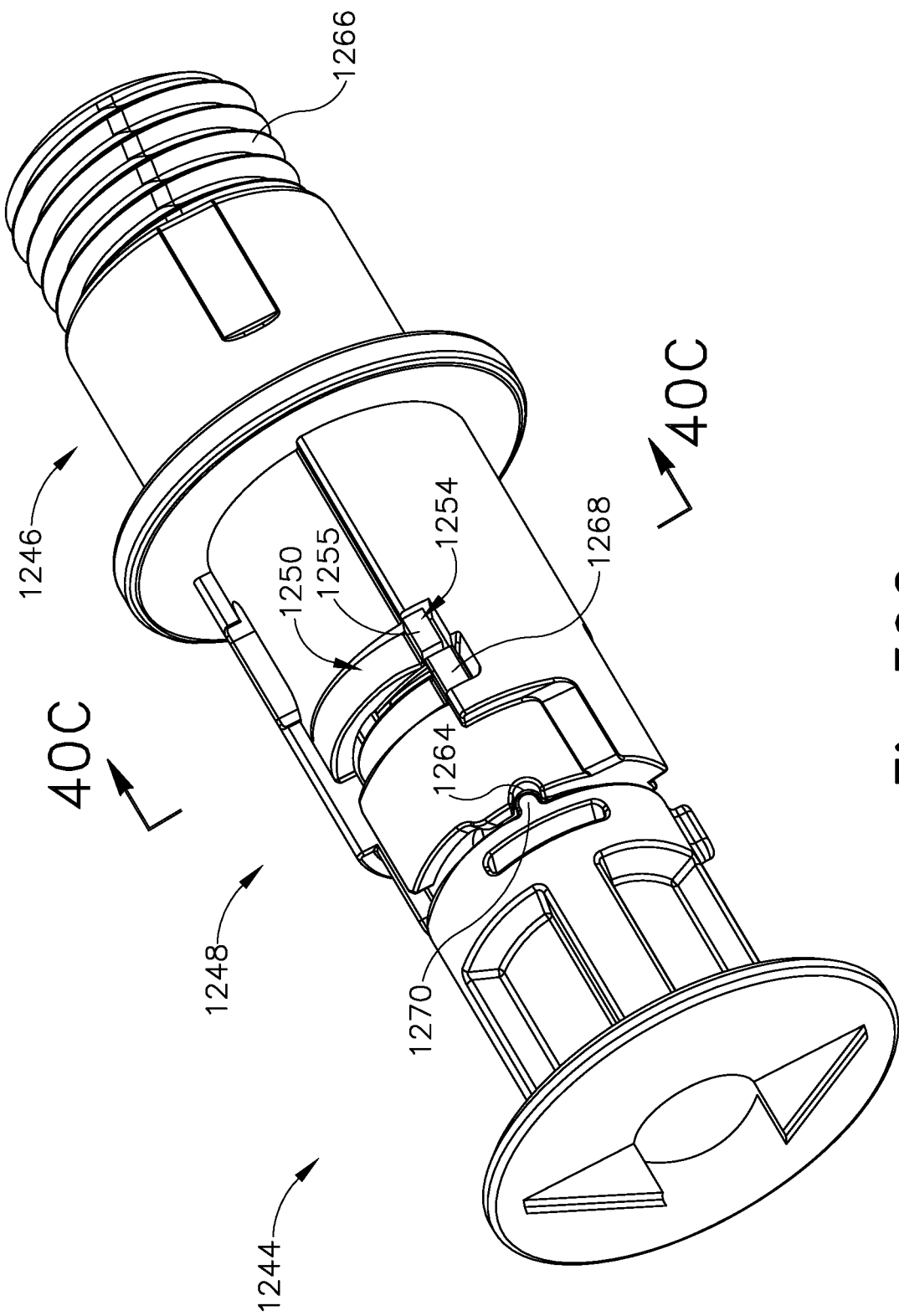
FIG. 39C depicts the schematic perspective view of the mechanical lockout assembly similar to FIG. 39B, but in the unlocked configuration.
Figure 40A:
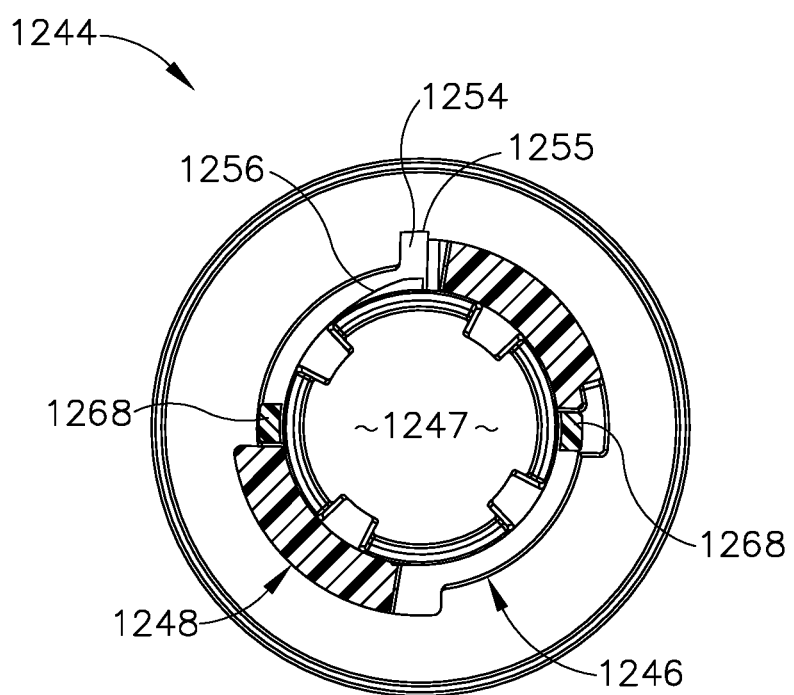
FIG. 40A depicts a schematic enlarged cross-sectional view of FIG. 39A taken along section line 40A-40A of FIG. 39A.
Figure 40B:
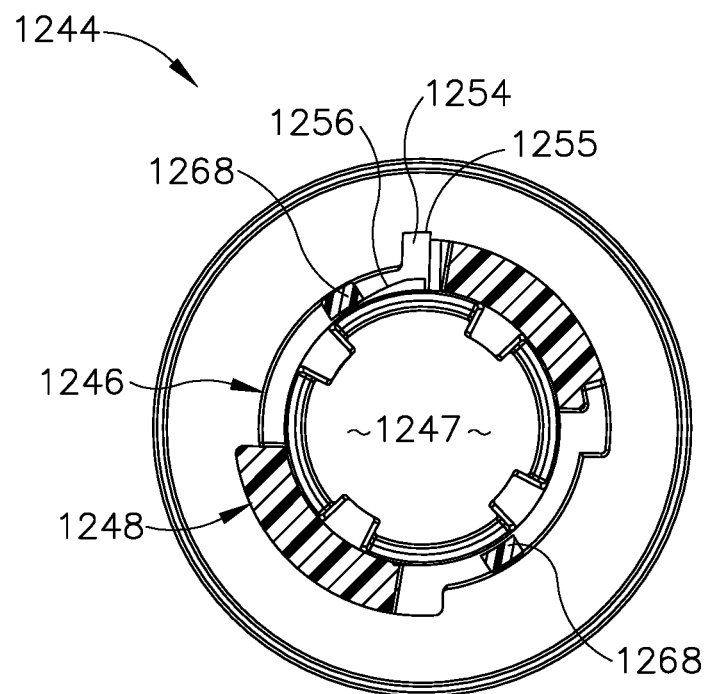
FIG. 40B depicts a schematic enlarged cross-sectional view of FIG. 39B taken along section line 40B-40B of FIG. 39B.
Figure 40C:
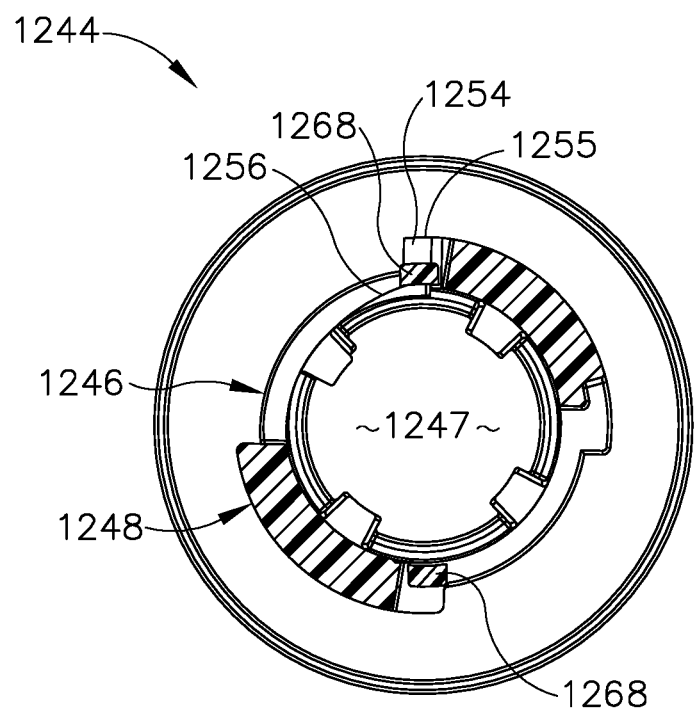
FIG. 40C depicts a schematic enlarged cross-sectional view of FIG. 39C taken along section line 40C-40C of FIG. 39C.

FIG. 38 shows bayonet collar (1248) as including at least one bayonet projection (1268), with two being shown in FIGS. 40A-40C, configured to contact cam surface (1256) of spring leg (1250) as bayonet collar (1248) is rotated relative to outer tube collar (1246) from a locked configuration to an unlocked configuration. Bayonet collar (1248) also includes protrusions (1270) that are configured to be received in cutouts (1264) as shown in FIG. 39C, to provide a detent coupling. Bayonet projection (1268) serves two purposes. First, bayonet projection (1268) pulls down interference tab (1254) to disengage interference tab (1254) from a lateral aperture (1276) in rotation collar (1249) shown in FIG. 41, thereby allowing the clamp arm drivetrain to translate longitudinally. Second, bayonet projection (1268) provides a coupling between bayonet collar (1248) and outer tube collar (1246), such that longitudinal motion of outer tube collar (1246) is communicated to bayonet collar (1248). When interference tab (1254) is disengaged from lateral aperture (1276) of rotation collar (1249) (see FIG. 41), movement of the clamp arm actuation assembly components within handle assembly (1212) is communicated to outer tube (1234) of shaft assembly (1214) via the engagement between outer tube and bayonet collars (1246, 1248), as provided by interference tab (1254).

Figure 39A:
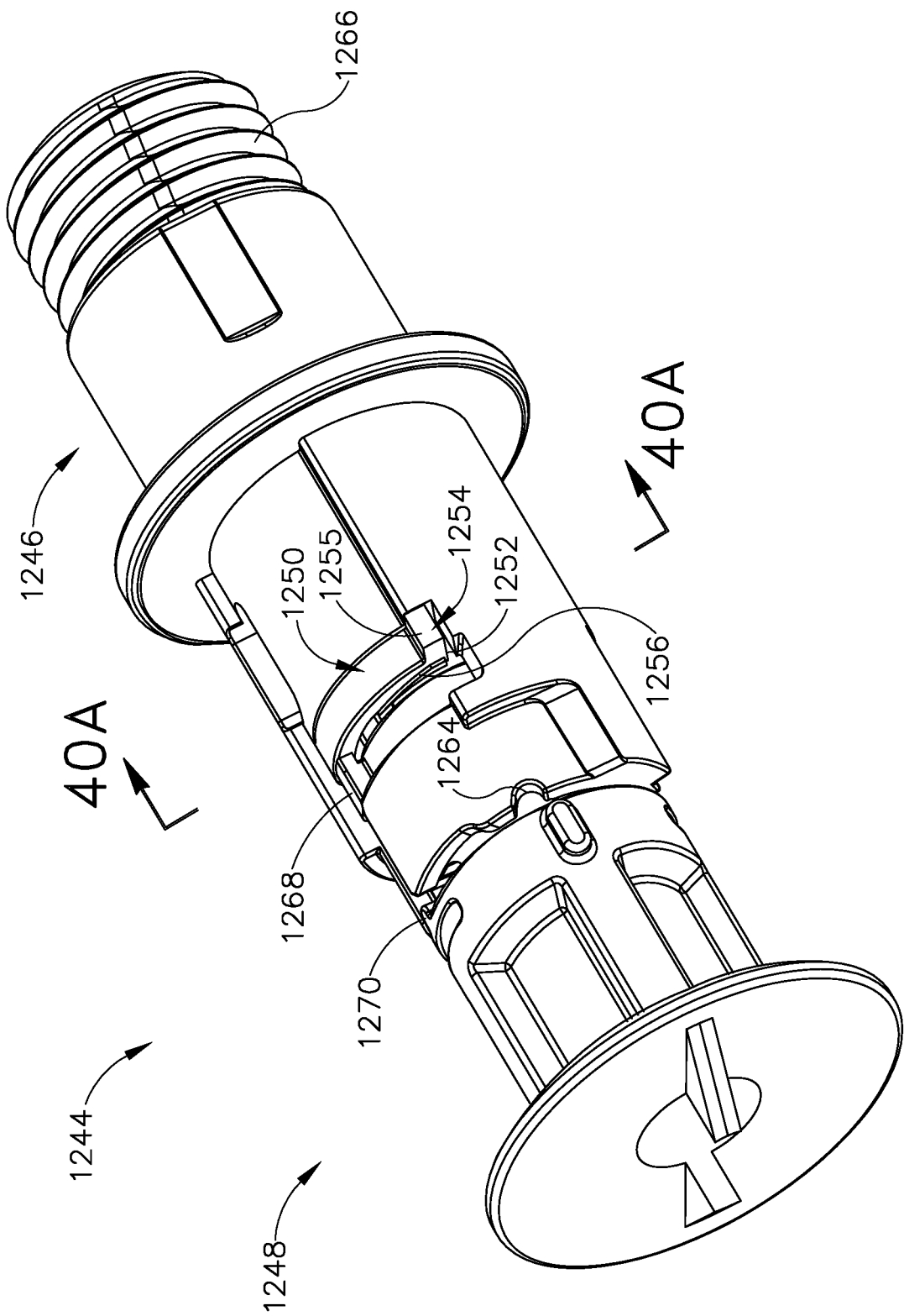
FIG. 39A depicts a schematic perspective view of the mechanical lockout assembly of FIG. 36 including the outer tube collar coupled with the bayonet collar in a locked configuration.
Figure 41:
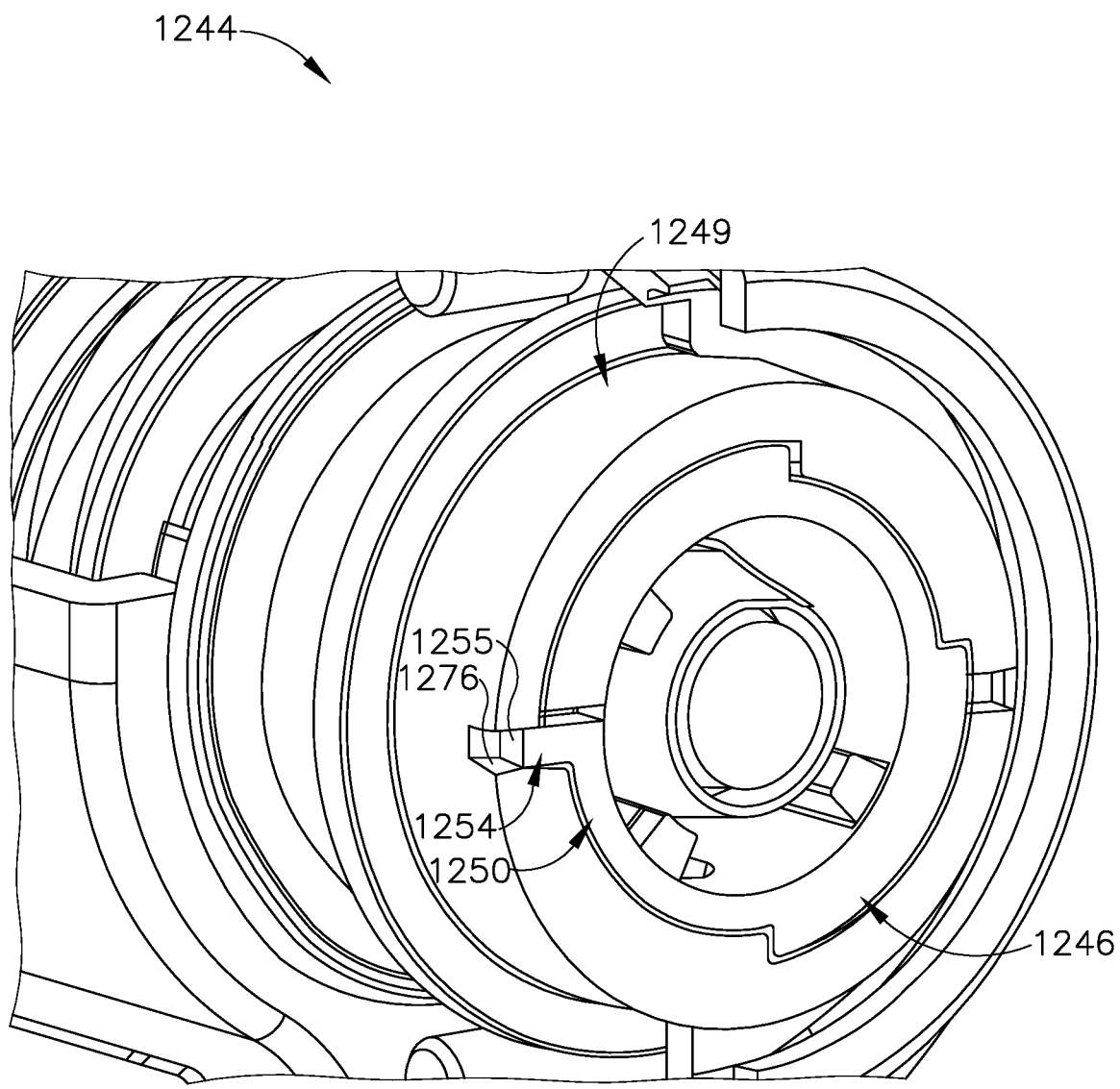
FIG. 41 depicts a schematic sectional view of the outer tube collar coupled with the rotation collar in the locked configuration.

FIGS. 39A, 40A, and 41 show instrument (1210) in the locked configuration, where handle assembly (1212) and shaft assembly (1214) are not fully coupled together. Rotation collar (1249) (see FIG. 41), includes a lateral aperture (1276) that receives interference tab (1254) to provide the locked configuration. In the locked configurations shown in FIGS. 39A, 40A, and 41, when interference tab (1254) of outer tube collar (1246) is positioned in lateral aperture (1276) of rotation collar (1249), outer tube collar (1246) is unable to translate. When outer tube collar (1246) is prevented from translating, trigger (1224) cannot be pivoted, and clamp arm (1230) cannot be pivoted toward ultrasonic blade (1228). At this stage, shaft assembly (1214) has been fully inserted longitudinally into handle assembly (1212), shown by bayonet collar (1248) contacting outer tube collar (1246). However, shaft assembly (1212) has not yet been rotated relative to handle assembly (1212) to fully seat shaft assembly (1214). More specifically, in the locked configuration, resilient interference tab (1254) of outer tube collar (1246) is not deflected inwardly, but instead is captured in lateral aperture (1276) of rotation collar (1249) shown in FIG. 41. As a result, mechanical lockout assembly (1244) prevents the operator from activating instrument (1210) using clamp arm closure trigger (1224). As shown in FIG. 40A, a central aperture (1247) extends through both outer tube collar (1246) and bayonet collar (1248) to receive an ultrasonic waveguide (not shown).

Figure 39B:
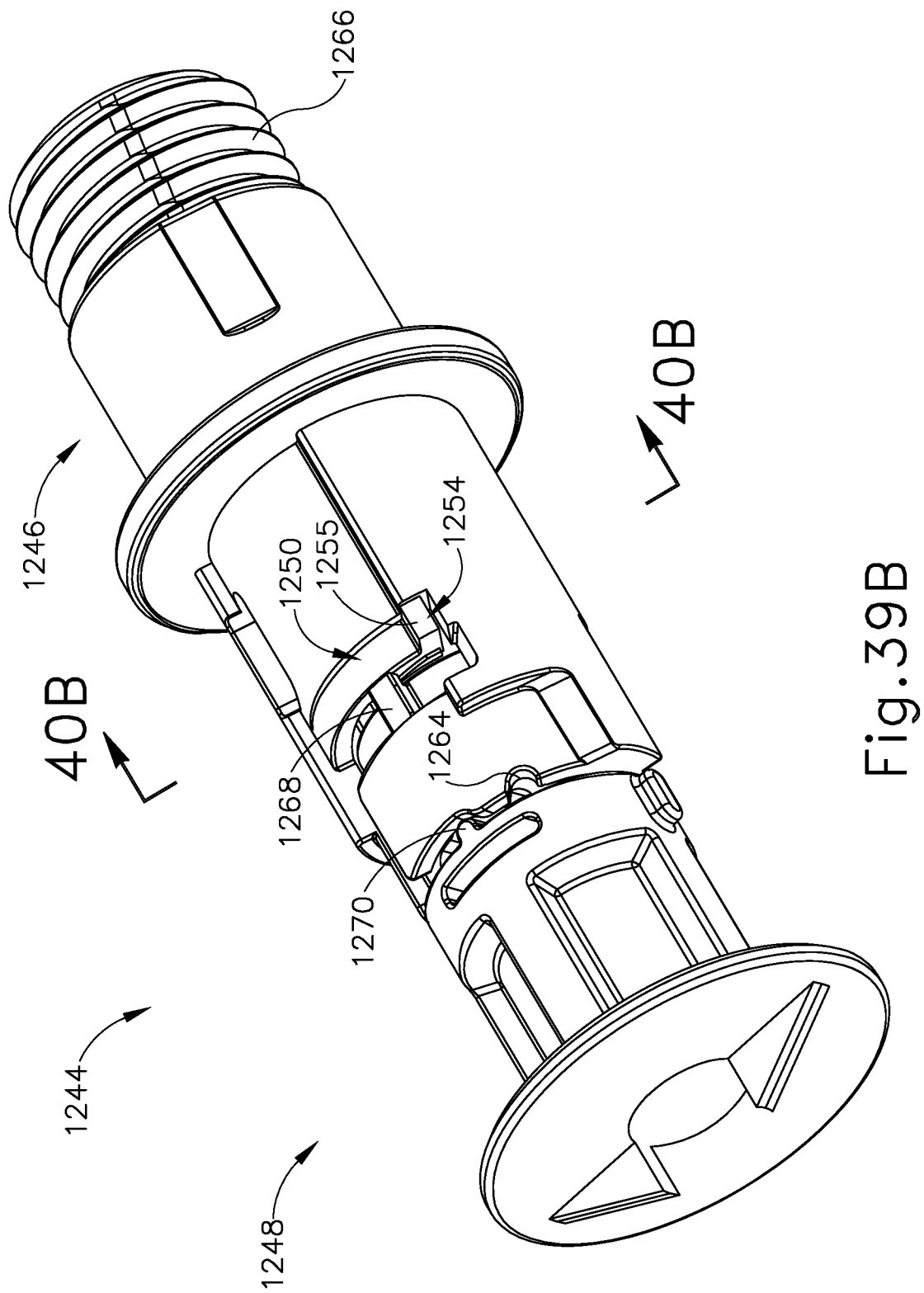
FIG. 39B depicts the schematic perspective view of the mechanical lockout assembly similar to FIG. 39A, moving from the locked configuration towards an unlocked configuration.

FIGS. 39B and 40B show instrument (1210) transitioning between the locked configuration and the unlocked configurations, with the operator still being prohibited from actuating trigger (1224). As shown, resilient interference tab (1254) is being pulled inward and outward of lateral aperture (1276) in rotation collar (1249) when bayonet collar (1248) is rotated. Bayonet projection (1268) rides along cam surface (1256) as bayonet collar (1248) is rotated, which pulls cam surface (1256) and the rest of resilient interference tab (1254) inward. As shown, cam surface (1256) is integrally formed as a unitary piece together with resilient interference tab (1254). More specifically, bayonet projection (1268) includes a radially extending component which travels through passageways (1258, 1262) and a proximally extending component which pulls down the spring leg (1250) supporting resilient interference tab (1254).

FIGS. 39C and 40C show instrument (1210) in the unlocked configuration, where handle assembly (1212) and shaft assembly (1214) are completely coupled together, such that the operator is able to activate instrument (1210) using trigger (1222). When interference tab (1254) is pulled out of lateral aperture (1276) of rotation collar (1249), outer tube collar (1246) is then free to translate, thereby enabling pivotal movement of trigger (1224), thereby enabling closure of clamp arm (1230) toward ultrasonic blade (1228). In the unlocked configuration, bayonet projections (1268) on bayonet collar (1248) push resilient interference tab (1254) inwards towards a center of outer tube collar (1246), enabling the shaft assembly (1214) including clamp arm (1230) to function. Outer tube (1234) translates relative to the rest of shaft assembly (1214) to provide pivotal movement of clamp arm (1230) toward/away from ultrasonic blade (1228). When the operator rotates shaft assembly (1214) to fully assemble instrument (1210), the operator would want to grasp rotation knob (1242) and hold it stationary.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a first modular assembly including at least one operator input feature; (b) an ultrasonic transducer supported by the first modular assembly; (c) a second modular assembly configured to be removably coupled with the first modular assembly, wherein the second modular assembly further includes at least a portion of an end effector extending distally from a distal end portion of the second modular assembly, and (d) a mechanical lockout assembly configured to switch between at least an unlocked configuration and a locked configuration, wherein in the locked configuration, the first modular assembly and the second modular assembly are partially coupled together such that the operator is physically prevented from activating the instrument using the operator input feature, and wherein in the unlocked configuration, the first modular assembly and the second modular assembly are completely coupled together and the operator is able to activate the instrument using the operator input feature.

Example 2

The ultrasonic surgical instrument of claim 1, wherein the first modular assembly further includes a handle assembly, a proximal outer sheath, and an ultrasonic blade, wherein the second modular assembly further includes a clamp arm assembly and a distal outer sheath, wherein the mechanical lockout assembly further includes at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm assembly relative to the ultrasonic blade, and wherein in the unlocked configuration, the proximal outer sheath is configured to couple with the distal outer sheath allowing closure of the clamp arm assembly relative to the ultrasonic blade.

Example 3

The ultrasonic surgical instrument of any one or more of Examples 1 through 2, wherein in the locked configuration, the lockout member prevents actuation of the clamp arm assembly due to an interference with both the clamp arm assembly and the distal outer sheath.

Example 4

The ultrasonic surgical instrument of any one or more of Examples 1 through 3, wherein the mechanical lockout assembly further includes a pin that pivotably couples the distal outer sheath with both the clamp arm assembly and the lockout member.

Example 5

The ultrasonic surgical instrument of any one or more of Examples 1 through 4, wherein the lockout member uses the same rotation point as the clamp arm assembly.

Example 6

The ultrasonic surgical instrument of any one or more of Examples 1 through 5, wherein the clamp arm assembly further includes at least one cutout portion, and wherein the lockout member is configured to move from the locked configuration to the unlocked configuration while being at least partially disposed within the cutout portion.

Example 7

The ultrasonic surgical instrument of any one or more of Examples 1 through 6, wherein the cutout portion includes a protrusion to inhibit translation of the lockout member while in the locked configuration.

Example 8

The ultrasonic surgical instrument of any one or more of Examples 1 through 7, wherein the lockout member moves distally away from the protrusion when moving from the locked configuration to the unlocked configuration.

Example 9

The ultrasonic surgical instrument of any one or more of Examples 1 through 8, wherein the proximal outer sheath includes a projection that displaces the lockout member distally when coupling the proximal outer sheath with the distal outer sheath.

Example 10

The ultrasonic surgical instrument of any one or more of Examples 1 through 9, wherein in the unlocked configuration, the clamp arm assembly freely rotates relative to the lockout member.

Example 11

The ultrasonic surgical instrument of any one or more of Examples 1 through 10, wherein the first modular assembly includes a handle assembly that includes a proximal outer sheath, and an ultrasonic blade, wherein the second modular assembly includes a clamp arm assembly and a distal outer sheath, wherein the mechanical lockout assembly further includes at least one projection operatively coupled with a clamp arm assembly, wherein in the locked configuration the projection is not received by a corresponding recess in the distal outer sheath, the locked configuration configured to prevent an operator from rotating the clamp arm assembly relative to the ultrasonic blade, and wherein in the unlocked configuration where the proximal outer sheath is coupled with the distal outer sheath, the projection is received by the corresponding recess in the distal outer sheath enabling the operator from rotating the clamp arm assembly relative to the ultrasonic blade.

Example 12

The ultrasonic surgical instrument of any one or more of Examples 1 through 11, wherein the first modular assembly further includes a handle assembly that includes the operator input feature, wherein the operator input feature includes at least one energy control button separated by a passageway from a switch, and wherein the mechanical lockout assembly further includes a barrier that includes a body portion and at least one aperture that translates between the locked configuration and the unlocked configuration within the passageway, wherein in the locked configuration, the body portion is disposed within the passageway between the energy control button and the switch preventing the switch from activating the instrument, and wherein in the unlocked configuration, the aperture is disposed within the passageway between the energy control button and the switch enabling the switch to activate the instrument.

Example 13

The ultrasonic surgical instrument any one or more of Examples 1 through 12, wherein the barrier includes a flexible member that is operatively coupled with the shaft assembly, wherein the flexible element is pushed into the passageway such that in the locked configuration the flexible member extends between the energy control button and the switch.

Example 14

The ultrasonic surgical instrument of any one or more of Examples 1 through 13, wherein in the unlocked configuration, at least one of the energy control button or the switch extends at least partially through the aperture of the barrier and makes direct physical contact with the other of the energy control button or the switch through the aperture.

Example 15

The ultrasonic surgical instrument of Examples 1 through 14, wherein the second modular assembly further includes a shaft assembly, wherein the mechanical lockout assembly further includes an angled slide that is configured to be contacted by a projection of the shaft assembly, wherein the angled slide is configured to contact the barrier causing the mechanical lockout assembly to transition from the locked configuration to the unlocked configuration, and wherein in the locked configuration, the body portion of the barrier is disposed within the passageway between the energy control button and the switch preventing the switch from activating the instrument.

Example 16

The ultrasonic surgical instrument of any one or more of Examples 1 through 15, wherein the first modular assembly includes the operator input feature, wherein the operator input feature includes at least one switch and a first portion of an energy control button, wherein the second modular assembly further includes a shaft assembly and a handle assembly that includes a second portion of the energy control button, and wherein in the locked configuration when the shaft assembly is partially coupled with the handle assembly, misalignment of the first and second portions of the energy control button prevents the switch from activating the instrument, and wherein in the unlocked configuration when the shaft assembly is completely coupled with the handle assembly, alignment of the first and second portions of the energy control button enables the switch to activate the instrument.

Example 17

The ultrasonic surgical instrument of any one or more of Examples 1 through 16, wherein the first modular assembly further includes a handle assembly that includes a trigger, wherein the second modular assembly further includes a shaft assembly, wherein the mechanical lockout assembly further includes a closure lever link operatively coupled with the trigger, wherein in the locked configuration when the shaft assembly is partially coupled with the handle assembly, the closure lever link is pulled over center in a first direction, preventing the closure lever link from being rotated closed which prevents the trigger from being actuated, and wherein in the unlocked configuration when the shaft assembly is completely coupled with the handle assembly, insertion of the shaft assembly causes the closure lever link to rotate in a second direction that is opposite the first direction allowing the trigger to be actuated.

Example 18

The ultrasonic surgical instrument of any one or more of Examples 1 through 17, wherein the mechanical lockout assembly further includes a one-way door that is configured to be opened by coupling a handle assembly of the first modular assembly with a shaft assembly of the second modular assembly, wherein in the locked configuration when the shaft assembly is partially coupled with the handle assembly, the one-way door blocks access of the handle assembly from the shaft assembly, wherein in moving from the locked configuration to the unlocked configuration, as an outer sheath is rotated, a translatable jacket threadably coupled with the outer sheath translates longitudinally relative to the one-way door pivoting the one-way door to an open position allowing for coupling of the shaft assembly with the handle assembly, and wherein in the unlocked configuration when the shaft assembly is completely coupled with the handle assembly allowing actuation of the instrument using the operator input feature.

Example 19

The ultrasonic surgical instrument of any one or more of Example 1 through 18, wherein a proximal portion of a shaft assembly of the second modular assembly includes a projection, wherein the mechanical lockout assembly includes a coupling device operatively coupled to a handle assembly of the first modular assembly, and wherein the coupling device includes a guide track that is configured to translate and rotate the shaft assembly using the interaction between the projection of the shaft assembly and the guide track of the coupling device from the locked configuration when the shaft assembly is partially coupled with the handle assembly to the unlocked configuration when the shaft assembly is completely coupled with the handle assembly.

Example 20

The ultrasonic surgical instrument of any one or more of Examples 1 through 19, wherein the mechanical lockout assembly includes: (i) an outer tube collar coupled with a handle assembly of the first modular assembly, wherein the outer tube collar includes a spring leg that includes a distal end, wherein the distal end of the spring leg includes a resilient interference tab, and (ii) a bayonet collar coupled with the shaft assembly, wherein the bayonet collar includes a bayonet projection that is configured to contact a cam surface of the spring leg as the bayonet collar is rotated relative to the outer tube collar from the locked configuration to the unlocked configuration, (iii) a rotation collar that includes an aperture, wherein in the locked configuration when the shaft assembly is partially coupled with the handle assembly, the interference tab of the outer tube collar deflects outwardly into an aperture of the rotation collar preventing activation of the instrument, and wherein in the unlocked configuration when the shaft assembly is completely coupled with the handle assembly, the bayonet projection contacts the cam surface of the interference tab to deflect the interference tab inwardly, enabling activation of the instrument.

Example 21

An ultrasonic surgical instrument, comprising: (a) a handle assembly including at least one operator input feature; (b) an ultrasonic transducer supported by the handle assembly; (c) a shaft assembly configured to removably couple with the handle assembly, wherein the shaft assembly includes a distal end portion, wherein the shaft assembly further includes: (i) an end effector extending distally from the distal end portion, and (ii) a waveguide acoustically coupled with the ultrasonic transducer; and (d) a mechanical lockout assembly configured to move between at least an unlocked configuration and a locked configuration, wherein in the locked configuration, the handle assembly and the shaft assembly are partially coupled together such that the operator is physically prevented from activating the instrument using the operator input feature, and wherein in the unlocked configuration, the handle assembly and shaft assembly are completely coupled together and the operator is able to activate the instrument using the operator input feature.

Example 22

The ultrasonic surgical instrument of any one or more of Examples 1 through 21, wherein the operator input feature further includes at least one energy control button that is separated by a passageway within the handle assembly from a switch within the handle assembly, wherein the mechanical lockout assembly further includes a barrier that includes a body portion and at least one aperture extending at least partially through the body portion, wherein the barrier translates within the passageway between the locked configuration and the unlocked configuration, wherein in the locked configuration, the body portion is disposed within the passageway between the energy control button and the switch preventing the switch from activating the instrument, and wherein in the unlocked configuration, the aperture is disposed within the passageway between the energy control button and the switch enabling the switch to activate the instrument.

Example 23

The ultrasonic surgical instrument of any one or more of Examples 1 through 22, wherein the mechanical lockout assembly further includes a one-way door that is configured to be opened by coupling the handle assembly with the shaft assembly, wherein in the locked configuration when the shaft assembly is partially coupled with the handle assembly, the one-way door blocks access of the handle assembly from the shaft assembly, and wherein in moving from the locked configuration to the unlocked configuration, as an outer sheath is rotated, a translatable jacket threadably coupled with the outer sheath longitudinally translates relative to the one-way door pivoting the one-way door to an open position allowing for coupling of the shaft assembly with the handle assembly, and wherein in the unlocked configuration when the shaft assembly is completely coupled with the handle assembly allowing actuation of the instrument using the operator input feature.

Example 24

A method of operating an ultrasonic surgical instrument, wherein the ultrasonic surgical instrument comprises: (a) a first modular assembly including at least one operator input feature; (b) an ultrasonic transducer supported by the first modular assembly; (c) a second modular assembly configured to removably couple with the first modular assembly, wherein the second modular assembly further includes at least a portion of an end effector extending distally from a distal end portion of the second modular assembly; and (d) a mechanical lockout assembly configured to switch between at least an unlocked configuration and a locked configuration, wherein the method comprises: (a) inhibiting the operator input feature from activating the instrument while in the locked configuration when the first modular assembly and the second modular assembly are only partially coupled together which provides instant feedback to an operator; (b) coupling the handle assembly and the shaft assembly completely together to disarm the mechanical lockout assembly; and (c) activating the instrument using the operator input feature when in the unlocked configuration.

Example 25

The method of Example 24, wherein the first modular assembly further includes a handle assembly that includes the at least operator input feature, wherein the operator input feature includes the energy control button separated by a passageway from a switch, wherein the mechanical lockout assembly further includes a barrier that includes a body portion and at least one aperture extending at least partially through the body portion, wherein the inhibiting activation further includes inhibiting activation of the instrument when the body portion of the barrier is disposed within the passageway between the energy control button and the switch, and wherein the coupling further includes translating the body portion of the barrier, so that the aperture of the body portion is disposed within the passageway between the energy control button and the switch enabling the switch to activate the instrument.

Example 26

An ultrasonic surgical instrument, comprising: (a) a handle assembly including at least one operator input feature; (b) an ultrasonic transducer supported by the handle assembly; (c) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (d) a mechanical lockout assembly configured to move between at least an unlocked configuration and a locked configuration, wherein in the locked configuration, the handle assembly and the shaft assembly are only partially coupled together physically preventing the operator from activating the instrument using the operator input feature, and wherein in the unlocked configuration, the handle assembly and shaft assembly are completely coupled together enabling the operator to activate the instrument using the operator input feature.

Example 27

The ultrasonic surgical instrument of Example 26, wherein in the locked configuration, the mechanical lockout assembly prevents the operator input feature of activating a trigger of the handle assembly that is operatively coupled with the end effector, wherein preventing activation of the trigger prevents the operator from clamping on tissue with the end effector.

Example 28

The ultrasonic surgical instrument of any one or more of Examples 26 through 27, wherein in the locked configuration, the mechanical lockout assembly prevents the operator input feature of activating at least one energy control button disposed on the handle assembly preventing the operator from activating the ultrasonic blade.

Example 29

The ultrasonic surgical instrument of any one or more of Examples 26 through 28, wherein a spring pushes the mechanical lockout assembly from the locked configuration to the unlocked configuration when the shaft assembly is removed from the handle assembly.

Example 30

The ultrasonic surgical instrument of any one or more of Examples 26 through 29, wherein the operator input feature includes at least one energy control button separated by a passageway from a switch within the handle assembly, wherein the mechanical lockout assembly further includes a barrier that includes a body portion and at least one aperture that translates within the passageway between the locked configuration and the unlocked configuration, wherein in the locked configuration when the shaft assembly is not completely coupled with the handle assembly, the body portion is disposed within the passageway between the energy control button and the switch preventing the switch from activating the instrument, and wherein in the unlocked configuration when the shaft assembly is completely coupled with the handle assembly, the aperture is disposed within the passageway between the energy control button and the switch enabling the switch to activate the instrument.

Example 31

The ultrasonic surgical instrument of any one or more of Examples 26 through 30, wherein the barrier includes a flexible member that is operatively coupled with the shaft assembly, wherein the flexible element is pushed into the passageway such that in the locked configuration the flexible member extends between the energy control button and the switch.

Example 32

The ultrasonic surgical instrument of any one or more of Examples 26 through 31, wherein in the unlocked configuration, at least one of the energy control button or the switch extends at least partially through the aperture of the barrier and makes direct physical contact with the other of the energy control button or the switch through the aperture.

Example 33

The ultrasonic surgical instrument of any one or more of Examples 26 through 32, wherein the mechanical lockout assembly further includes an angled slide that is configured to be contacted by a projection of the shaft assembly, wherein the angled slide is configured to contact the barrier causing the mechanical lockout assembly to transition from the locked configuration to the unlocked configuration, and wherein in the locked configuration, the body portion of the barrier is disposed within the passageway between the energy control button and the switch preventing the switch from activating the instrument.

Example 34

The ultrasonic surgical instrument of any one or more of Examples 26 through 33, wherein the shaft assembly includes a projection that contacts the angled slide causing an angled proximal end of angled slide to push the barrier further into the passageway using a camming action.

Example 35

The ultrasonic surgical instrument of any one or more of Examples 26 through 34, wherein the handle assembly includes the operator input feature that includes at least one switch and a first portion of an energy control button, wherein the shaft assembly includes a second portion of an energy control button, and wherein in the locked configuration when the shaft assembly is partially coupled with the handle assembly, misalignment of the first and second portions of the energy control button prevents the switch from activating the instrument, and wherein in the unlocked configuration when the shaft assembly is completely coupled with the handle assembly, alignment of the first and second portions of the energy control button enables the switch to activate the instrument.

Example 36

The ultrasonic surgical instrument of any one or more of Examples 26 through 35, wherein the handle assembly includes the operator input feature, wherein the operator input feature includes a trigger, wherein the mechanical lockout assembly further includes a closure lever link operatively coupled with the trigger, wherein in the locked configuration when the shaft assembly is partially coupled with the handle assembly, the closure lever link is pulled over center in a first direction, preventing the closure lever link from being rotated closed which prevents the trigger from being actuated which prevents the end effector from closing, and wherein in the unlocked configuration when the shaft assembly is completely coupled with the handle assembly, insertion of the shaft assembly causes the closure lever link to rotate in a second direction that is opposite the first direction allowing the trigger to be actuated enabling the end effector to close.

Example 37

The ultrasonic surgical instrument of any one or more of Examples 26 through 36, wherein the mechanical lockout assembly further includes a one-way door that is configured to be opened by coupling the shaft assembly with the handle assembly, wherein in the locked configuration when the shaft assembly is partially coupled with the handle assembly, the one-way door prevents a connecting portion of the ultrasonic transducer from reaching a connecting portion of a proximal end of the ultrasonic waveguide; wherein in moving from the locked configuration to the unlocked configuration, as an outer sheath is rotated, a translatable jacket threadably coupled with the outer sheath translates longitudinally relative to the one-way door pivoting the one-way door to an open position allowing the connecting portions of the ultrasonic transducer and the ultrasonic waveguide to acoustically couple, and wherein in the unlocked configuration when the shaft assembly is completely coupled with the handle assembly allowing end effector to be actuated using the operator input feature.

Example 38

The ultrasonic surgical instrument of any one or more of Examples 26 through 37, wherein a proximal portion of the shaft assembly includes a projection, wherein the mechanical lockout assembly includes a coupling device operatively coupled with the handle assembly, and wherein the coupling device includes a guide track that is configured to translate and rotate the shaft assembly using the interaction between the projection of the shaft assembly and the guide track of the coupling device from the locked configuration when the shaft assembly is partially coupled with the handle assembly to the unlocked configuration when the shaft assembly is completely coupled with the handle assembly.

Example 39

The ultrasonic surgical instrument of any one or more of Examples 26 through 38, wherein the coupling device translates longitudinally in response to pivotal movement of a trigger, and wherein the coupling device operatively couples the trigger with the clamp arm of the shaft assembly.

Example 40

The ultrasonic surgical instrument of any one or more of Examples 26 through 39, wherein the mechanical lockout assembly includes: (i) an outer tube collar coupled with the handle assembly, wherein the outer tube collar includes a spring leg that includes a distal end, wherein the distal end of the spring leg includes a resilient interference tab; and (ii) a bayonet collar coupled with the shaft assembly, wherein the bayonet collar includes a bayonet projection that is configured to contact a cam surface of the spring leg as the bayonet collar is rotated relative to the outer tube collar from the locked configuration to the unlocked configuration; and (iii) a rotation collar that includes an aperture, wherein in the locked configuration when the shaft assembly is partially coupled with the handle assembly, the interference tab of the outer tube collar deflects outwardly into the aperture of the rotation collar preventing activation of the instrument, and wherein in the unlocked configuration when the shaft assembly is completely coupled with the handle assembly, the bayonet projection contacts the cam surface of the interference tab to deflect the interference tab inwardly, enabling activation of the instrument.

Example 41

An ultrasonic surgical instrument, comprising: (a) a handle assembly including at least one energy control button that is separated by a passageway from a switch within the handle assembly; (b) an ultrasonic transducer supported by the handle assembly; (c) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (d) a barrier that includes a body portion and at least one aperture extending at least partially through the body portion, wherein the barrier translates within the passageway between the locked configuration and the unlocked configuration, wherein in the locked configuration, the body portion is disposed within the passageway between the energy control button and the switch preventing the switch from activating the instrument, and wherein in the unlocked configuration, the aperture is disposed within the passageway between the energy control button and the switch, and at least one of the energy control button or the switch extends at least partially through the aperture of the barrier and makes direct physical contact with the other of the energy control button or the switch through the aperture enabling the switch to activate the instrument.

Example 42

A method of operating an ultrasonic surgical instrument, wherein the ultrasonic surgical instrument comprises: (a) a handle assembly including at least one operator input feature and an ultrasonic transducer supported by the handle assembly; (b) a shaft assembly configured to removably couple with the handle assembly, wherein the shaft assembly includes a distal end portion, wherein the shaft assembly further includes: (i) an end effector extending distally from the distal end portion, and (ii) an ultrasonic waveguide configured to be acoustically coupled with the ultrasonic transducer; and (c) a mechanical lockout assembly configured to move between at least an unlocked configuration and a locked configuration, wherein the method comprises: (a) inhibiting the operator input feature from activating the instrument while in the locked configuration when the handle assembly and the shaft assembly are partially coupled together, wherein inhibiting activation of the instrument provides instant feedback to an operator; (b) coupling the handle assembly and the shaft assembly completely together to disarm the locking assembly; and (c) activating the instrument using the operator input feature when in the unlocked configuration.

Example 43

The method of Example 43, wherein the inhibiting activation further includes the mechanical lockout assembly preventing the operator input feature of locking an operator activated trigger of the handle assembly that is operatively coupled with the end effector, thereby preventing the operator from clamping on tissue with the end effector.

Example 44

The method of any one or more of Examples 43 through 44, wherein the inhibiting activation further includes the mechanical lockout assembly preventing the operator input feature of activating at least one energy control button preventing the operator from activating the ultrasonic blade.

Example 45

An ultrasonic surgical instrument, comprising: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) a mechanical lockout assembly configured to switch between at least an unlocked configuration and a locked configuration, wherein in the locked configuration, the handle assembly and the clamp arm assembly are not completely coupled together and the operator is physically prevented from activating the instrument using an operator input feature, and wherein in the unlocked configuration, the clamp arm assembly and the shaft assembly are completely coupled together and the operator is able to activate the instrument using the operator input feature.

Example 46

The ultrasonic surgical instrument of Example 45, wherein in the locked configuration the mechanical lockout assembly prevents the operator input feature of rotating the clamp arm relative to the ultrasonic blade, thereby preventing the operator from clamping onto tissue by rotating the clamp arm relative to the ultrasonic blade Example 47

The ultrasonic surgical instrument of any one or more of Examples 45 through 46, wherein the mechanical lockout assembly prevents the operator input feature of activating at least one energy control button disposed on the handle assembly preventing activation of the ultrasonic blade Example 48

The ultrasonic surgical instrument of any one or more of Examples 45 through 47, wherein the mechanical lockout assembly further includes at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm relative to the ultrasonic blade, and wherein in the unlocked configuration, the lockout feature allows rotation of the clamp arm relative to the ultrasonic blade Example 49

The ultrasonic surgical instrument of any one or more of Examples 45 through 48, wherein the lockout member uses the same rotation point as the clamp arm assembly Example 50

The ultrasonic surgical instrument of any one or more of Examples 45 through 49, wherein the clamp arm assembly further includes at least one cutout portion, and wherein the lockout member is configured to move from the locked configuration to the unlocked configuration while being at least partially disposed within the cutout portion Example 51

The ultrasonic surgical instrument of any one or more of Examples 45 through 50, wherein the cutout portion includes a protrusion to inhibit translation of the lockout member while in the locked configuration Example 52

The ultrasonic surgical instrument of any one or more of Examples 45 through 51, wherein in the unlocked configuration, the clamp arm assembly freely rotates relative to the lockout member

Example 53

The ultrasonic surgical instrument of any one or more of Examples 45 through 52, wherein the clamp arm assembly includes an outer sheath, wherein the mechanical lockout assembly further includes at least one projection operatively coupled with a clamp arm assembly, wherein in the locked configuration the projection is not received by a corresponding recess in the outer sheath, the locked configuration preventing the operator input feature of rotating the clamp arm relative to the ultrasonic blade as the projection provides a hard stop preventing the clamp arm from pivoting toward the ultrasonic blade, and wherein in the unlocked configuration where the proximal outer sheath is coupled with the distal outer sheath, the projection is received by the corresponding recess in the distal outer sheath enabling the operator input feature of rotating the clamp arm assembly relative to the ultrasonic blade

Example 54

The ultrasonic surgical instrument of any one or more of Examples 45 through 53, wherein the projection is a curvilinear projection that in the unlocked configuration is received by a curvilinear recess in the outer sheath

Example 55

The ultrasonic surgical instrument of any one or more of Examples 45 through 54, wherein the handle assembly further includes the operator input feature, wherein the operator input feature includes at least one energy control button separated by a passageway from a switch within the housing, wherein the mechanical lockout assembly further includes a barrier that includes a body portion and at least one aperture that translates between the locked configuration and the unlocked configuration within the passageway, wherein in the locked configuration, the body portion is disposed within the passageway between the energy control button and the switch preventing the switch from activating the instrument, and wherein in the unlocked configuration, the aperture is disposed within the passageway between the energy control button and the switch enabling the switch to activate the instrument

Example 56

The ultrasonic surgical instrument of any one or more of Examples 45 through 55, wherein the barrier includes a flexible member that is operatively coupled with the shaft assembly, and wherein the flexible element is pushed into the passageway such that in the locked configuration the flexible member extends between the energy control button and the switch

Example 57

The ultrasonic surgical instrument of any one or more of Examples 45 through 56, wherein in the unlocked configuration, at least one of the energy control button or the switch extends at least partially through the aperture of the barrier and makes direct physical contact with the other of the energy control button or the switch through the aperture

Example 58

The ultrasonic surgical instrument of any one or more of Examples 45 through 57, wherein a coupling mechanism attaches the barrier to the clamp arm assembly

Example 59

The ultrasonic surgical instrument of any one or more of Examples 45 through 58, wherein a spring pushes the mechanical lockout assembly from the locked configuration to the unlocked configuration when the clamp arm assembly is removed from the handle assembly

Example 60

An ultrasonic surgical instrument, comprising: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm relative to the ultrasonic blade, and wherein in the unlocked configuration, the lockout feature allows rotation of the clamp arm relative to the ultrasonic blade

Example 61

The ultrasonic surgical instrument of any one or more of Examples 45 through 58 and 60, wherein the handle assembly includes a projection that displaces the lockout member distally when coupling the handle assembly with the clamp arm assembly

Example 62

A method of operating an ultrasonic surgical instrument, wherein the ultrasonic surgical instrument comprises: (a) an ultrasonic transducer; (b) a handle assembly supporting the ultrasonic transducer, wherein the handle assembly includes: (i) a housing; and (ii) an ultrasonic blade acoustically coupled with the ultrasonic transducer; (c) a clamp arm assembly including a clamp arm; and (d) a mechanical lockout assembly configured to switch between at least an unlocked configuration and a locked configuration, wherein the method comprises: (a) inhibiting the operator input feature from activating the instrument while in the locked configuration when the handle assembly and the clamp arm assembly are partially coupled together, wherein inhibiting rotation of the clamp arm provides instant feedback to an operator; (b) coupling the handle assembly and the clamp arm assembly completely together to disarm the locking assembly; and (c) activating the instrument using the operator input feature when in the unlocked configuration

Example 63

The method of Example 62, wherein the inhibiting the operator input feature further includes the mechanical lockout assembly preventing the operator input feature of rotating the clamp arm relative to the ultrasonic blade that prevents the operator from clamping onto tissue

Example 64

The method of any one or more of Examples 62 through 63, wherein the inhibiting the operator input feature further includes the mechanical lockout assembly preventing the operator input feature of activating at least one energy control button disposed on the handle assembly preventing the operator from activating the ultrasonic blade.

V. Miscellaneous

It should be understood that the various teachings herein may be readily combined with the various teachings of U.S. Pub. No. 2017/0105754, entitled "Surgical Instrument with Dual Mode End Effector and Side-Loaded Clamp Arm Assembly," published on April 2017, the disclosure of which is incorporated by reference herein. Various suitable ways in which the teachings herein may be combined with the teachings of U.S. Pub. No. 2017/0105754 will be apparent to those of ordinary skill in the art.

It should be understood that the various teachings herein may be readily combined with the various teachings of U.S. Pub. No. 2017/0105755, entitled "Surgical Instrument with Dual Mode End Effector and Compound Lever with Detents," published on Apr. 20, 2017, the disclosure of which is incorporated by reference herein. Various suitable ways in which the teachings herein may be combined with the teachings of U.S. Pub. No. 2017/0105755 will be apparent to those of ordinary skill in the art.

It should be understood that the various teachings herein may be readily combined with the various teachings of U.S. Pub. No. 2017/0105788, entitled "Surgical Instrument with Dual Mode End Effector and Modular Clamp Arm Assembly," filed on Apr. 20, 2017, the disclosure of which is incorporated by reference herein. Various suitable ways in which the teachings herein may be combined with the teachings of U.S. Pub. No. 2017/0105788 will be apparent to those of ordinary skill in the art.

The various instruments described above may be used in a variety of kinds of surgical procedures. By way of example only, the instruments described above may be used to perform liver resection, colorectal surgical procedures, gynecological surgical procedures, and/or various other kinds of surgical procedures. Various other kinds of procedures and ways in which the instruments described above may be used will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
    (a) a first modular assembly including at least one operator input feature;
    (b) an ultrasonic transducer supported by the first modular assembly and operatively connected to the at least one operator input feature;

(c) a second modular assembly configured to be removably coupled with the first modular assembly, wherein the second modular assembly further includes at least a portion of an end effector extending distally from a distal end portion of the second modular assembly; and (d) a mechanical lockout assembly configured to switch between at least an unlocked configuration and a locked configuration, wherein in the locked configuration, the first modular assembly and the second modular assembly are partially coupled together such that the operator is physically prevented from activating the ultrasonic transducer using the at least one operator input feature, and wherein in the unlocked configuration, the first modular assembly and the second modular assembly are completely coupled together and the operator is able to activate the ultrasonic transducer using the at least one operator input feature.

2. The ultrasonic surgical instrument of claim 1, wherein the first modular assembly further includes a handle assembly, a proximal outer sheath, and an ultrasonic blade, wherein the second modular assembly further includes a clamp arm assembly and a distal outer sheath, wherein the mechanical lockout assembly further includes at least one lockout member having a body that includes a lockout feature, wherein the lockout feature includes at least one of a curve, a change in angle, a slot, or a proximal extrusion from the body, wherein in the locked configuration, the lockout feature prevents rotation of the clamp arm assembly relative to the ultrasonic blade, and wherein in the unlocked configuration, the proximal outer sheath is configured to couple with the distal outer sheath allowing closure of the clamp arm assembly relative to the ultrasonic blade.

3. The ultrasonic surgical instrument of claim 2, wherein in the locked configuration, the lockout member prevents actuation of the clamp arm assembly due to an interference with both the clamp arm assembly and the distal outer sheath.

4. The ultrasonic surgical instrument of claim 2, wherein the mechanical lockout assembly further includes a pin that pivotably couples the distal outer sheath with both the clamp arm assembly and the lockout member.

5. The ultrasonic surgical instrument of claim 2, wherein the proximal outer sheath includes a projection that displaces the lockout member distally when coupling the proximal outer sheath with the distal outer sheath.

6. The ultrasonic surgical instrument of claim 1, wherein the first modular assembly includes a handle assembly that includes a proximal outer sheath, and an ultrasonic blade, wherein the second modular assembly includes a clamp arm assembly and a distal outer sheath, wherein the mechanical lockout assembly further includes at least one projection operatively coupled with a clamp arm assembly, wherein in the locked configuration the projection is not received by a corresponding recess in the distal outer sheath, the locked configuration configured to prevent an operator from rotating the clamp arm assembly relative to the ultrasonic blade, and wherein in the unlocked configuration where the proximal outer sheath is coupled with the distal outer sheath, the projection is received by the corresponding recess in the distal outer sheath enabling the operator from rotating the clamp arm assembly relative to the ultrasonic blade.

7. The ultrasonic surgical instrument of claim 1, wherein the first modular assembly further includes a handle assembly that includes the at least one operator input feature, wherein the at least one operator input feature includes at least one energy control button separated by a passageway from a switch, wherein the mechanical lockout assembly further includes a barrier that includes a body portion and at least one aperture that translates between the locked configuration and the unlocked configuration within the passageway, wherein in the locked configuration, the body portion is disposed within the passageway between the at least one energy control button and the switch preventing the switch from activating the instrument, and wherein in the unlocked configuration, the at least one aperture is disposed within the passageway between the at least one energy control button and the switch enabling the switch to activate the instrument.

8. The ultrasonic surgical instrument of claim 7, wherein the barrier includes a flexible member that is operatively coupled with a shaft assembly of the second modular assembly, wherein the flexible element is pushed into the passageway such that in the locked configuration the flexible member extends between the at least one energy control button and the switch.

9. The ultrasonic surgical instrument of claim 7, wherein in the unlocked configuration, at least one of the at least one energy control button or the switch extends at least partially through the at least one aperture of the barrier and makes direct physical contact with the other of the at least one energy control button or the switch through the at least one aperture.

10. The ultrasonic surgical instrument of claim 7, wherein the second modular assembly further includes a shaft assembly, wherein the mechanical lockout assembly further includes an angled slide that is configured to be contacted by a projection of the shaft assembly, wherein the angled slide is configured to contact the barrier causing the mechanical lockout assembly to transition from the locked configuration to the unlocked configuration, and wherein in the locked configuration, the body portion of the barrier is disposed within the passageway between the at least one energy control button and the switch preventing the switch from activating the ultrasonic transducer.

11. The ultrasonic surgical instrument of claim 1, wherein the first modular assembly includes the at least one operator input feature, wherein the at least one operator input feature includes at least one switch and a first portion of an energy control button, wherein the second modular assembly further includes a shaft assembly and a handle assembly that includes a second portion of the at least one energy control button, wherein in the locked configuration when the shaft assembly is partially coupled with the handle assembly, misalignment of the first and second portions of the at least one energy control button prevents the at least one switch from activating the ultrasonic transducer, and wherein in the unlocked configuration when the shaft assembly is completely coupled with the handle assembly, alignment of the first and second portions of the at least one energy control button enables the at least one switch to activate the ultrasonic transducer.

12. The ultrasonic surgical instrument of claim 1, wherein the first modular assembly further includes a handle assembly that includes a trigger, wherein the second modular assembly further includes a shaft assembly, wherein the mechanical lockout assembly further includes a closure lever link operatively coupled with the trigger, wherein in the locked configuration when the shaft assembly is partially coupled with the handle assembly, the closure lever link is pulled over center in a first direction, preventing the closure lever link from being rotated closed which prevents the trigger from being actuated, and wherein in the unlocked configuration when the shaft assembly is completely coupled with the handle assembly, insertion of the shaft assembly causes the closure lever link to rotate in a second direction that is opposite the first direction allowing the trigger to be actuated.

13. The ultrasonic surgical instrument of claim 1, wherein the mechanical lockout assembly further includes a one-way door that is configured to be opened by coupling a handle assembly of the first modular assembly with a shaft assembly of the second modular assembly, wherein in the locked configuration when the shaft assembly is partially coupled with the handle assembly, the one-way door blocks access of the handle assembly from the shaft assembly, wherein in moving from the locked configuration to the unlocked configuration, as an outer sheath is rotated, a translatable jacket threadably coupled with the outer sheath translates longitudinally relative to the one-way door pivoting the one-way door to an open position allowing for coupling of the shaft assembly with the handle assembly, and wherein in the unlocked configuration when the shaft assembly is completely coupled with the handle assembly allowing actuation of the ultrasonic transducer using the at least one operator input feature.

14. The ultrasonic surgical instrument of claim 1, wherein a proximal portion of a shaft assembly of the second modular assembly includes a projection, wherein the mechanical lockout assembly includes a coupling device operatively coupled to a handle assembly of the first modular assembly, and wherein the coupling device includes a guide track that is configured to translate and rotate the shaft assembly using the interaction between the projection of the shaft assembly and the guide track of the coupling device from the locked configuration when the shaft assembly is partially coupled with the handle assembly to the unlocked configuration when the shaft assembly is completely coupled with the handle assembly.

15. The ultrasonic surgical instrument of claim 1, wherein the mechanical lockout assembly includes:
 i. an outer tube collar coupled with a handle assembly of the first modular assembly, wherein the outer tube collar includes a spring leg that includes a distal end, wherein the distal end of the spring leg includes a resilient interference tab; and
 ii. a bayonet collar coupled with a shaft assembly of the second modular assembly, wherein the bayonet collar includes a bayonet projection that is configured to contact a cam surface of the spring leg as the bayonet collar is rotated relative to the outer tube collar from the locked configuration to the unlocked configuration;
 iii. a rotation collar that includes an aperture,
 wherein in the locked configuration when the shaft assembly is partially coupled with the handle assembly, the interference tab of the outer tube collar deflects outwardly into the aperture of the rotation collar preventing activation of the ultrasonic transducer, and
 wherein in the unlocked configuration when the shaft assembly is completely coupled with the handle assembly, the bayonet projection contacts the cam surface of the spring leg to deflect the interference tab inwardly, enabling activation of the ultrasonic transducer.

16. An ultrasonic surgical instrument, comprising:
 (a) a handle assembly including at least one operator input feature;
 (b) an ultrasonic transducer supported by the handle assembly and operatively connected to the at least one operator input feature;
 (c) a shaft assembly configured to removably couple with the handle assembly, wherein the shaft assembly includes a distal end portion, wherein the shaft assembly further includes:
  (i) an end effector extending distally from the distal end portion; and
  (ii) a waveguide acoustically coupled with the ultrasonic transducer; and
 (d) a mechanical lockout assembly configured to move between at least an unlocked configuration and a locked configuration,
 wherein in the locked configuration, the handle assembly and the shaft assembly are partially coupled together such that the operator is physically prevented from activating the ultrasonic transducer using the at least one operator input feature, and
 wherein in the unlocked configuration, the handle assembly and shaft assembly are completely coupled together and the operator is able to activate the ultrasonic transducer using the at least one operator input feature.

17. The ultrasonic surgical instrument of claim 16, wherein the at least one operator input feature further includes at least one energy control button that is separated by a passageway within the handle assembly from a switch within the handle assembly, wherein the mechanical lockout assembly further includes a barrier that includes a body portion and at least one aperture extending at least partially through the body portion, wherein the barrier translates within the passageway between the locked configuration and the unlocked configuration, wherein in the locked configuration, the body portion is disposed within the passageway between the at least one energy control button and the switch preventing the switch from activating the ultrasonic transducer, and wherein in the unlocked configuration, the at least one aperture is disposed within the passageway between the energy control button and the switch enabling the switch to activate the ultrasonic transducer.

18. The ultrasonic surgical instrument of claim 16, wherein the mechanical lockout assembly further includes a one-way door that is configured to be opened by coupling the handle assembly with the shaft assembly, wherein in the locked configuration when the shaft assembly is partially coupled with the handle assembly, the one-way door blocks access of the handle assembly from the shaft assembly, wherein in moving from the locked configuration to the unlocked configuration, as an outer sheath is rotated, a translatable jacket threadably coupled with the outer sheath longitudinally translates relative to the one-way door pivoting the one-way door to an open position allowing for coupling of the shaft assembly with the handle assembly, and wherein in the unlocked configuration when the shaft assembly is completely coupled with the handle assembly allowing actuation of the ultrasonic transducer using the at least one operator input feature.

19. A method of operating an ultrasonic surgical instrument, wherein the ultrasonic surgical instrument includes: (a) a first modular assembly including at least one operator input feature; (b) an ultrasonic transducer supported by the first modular assembly; (c) a second modular assembly configured to removably couple with the first modular assembly, wherein the second modular assembly further includes at least a portion of an end effector extending distally from a distal end portion of the second modular assembly; and (d) a mechanical lockout assembly configured to switch between at least an unlocked configuration and a locked configuration, the method comprising:

(a) inhibiting the at least one operator input feature from activating the ultrasonic transducer while in the locked configuration when the first modular assembly and the second modular assembly are only partially coupled together which provides instant feedback to an operator;

(b) coupling the first modular assembly and the second modular assembly completely together to disarm the mechanical lockout assembly; and (c) activating the ultrasonic transducer using the at least one operator input feature when in the unlocked configuration.

20. The method of claim 19, wherein the first modular assembly further includes a handle assembly that includes the at least one operator input feature, wherein the at least one operator input feature includes a energy control button separated by a passageway from a switch, wherein the mechanical lockout assembly further includes a barrier that includes a body portion and at least one aperture extending at least partially through the body portion, wherein the inhibiting activation further includes inhibiting activation of the ultrasonic transducer when the body portion of the barrier is disposed within the passageway between the energy control button and the switch, and wherein the coupling further includes translating the body portion of the barrier, so that the at least one aperture of the body portion is disposed within the passageway between the energy control button and the switch enabling the switch to activate the ultrasonic transducer.

* * * * *